(12) United States Patent
Arimura et al.

(10) Patent No.: US 7,008,954 B1
(45) Date of Patent: Mar. 7, 2006

(54) TH2 DIFFERENTIATION INHIBITORS

(75) Inventors: Akinori Arimura, Toyonaka (JP); Kenji Kawada, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 91 days.

(21) Appl. No.: 09/980,475

(22) PCT Filed: Jul. 14, 2000

(86) PCT No.: PCT/JP00/04725

§ 371 (c)(1),
(2), (4) Date: Dec. 3, 2001

(87) PCT Pub. No.: WO01/07032

PCT Pub. Date: Feb. 1, 2001

(30) Foreign Application Priority Data

Jul. 23, 1999 (JP) ................................. 11-209298

(51) Int. Cl.
*A61K 31/09* (2006.01)
*A61K 31/136* (2006.01)
*A61K 31/15* (2006.01)

(52) U.S. Cl. ...................................... 514/351; 546/300
(58) Field of Classification Search ................ 546/300; 514/351
See application file for complete search history.

(56) References Cited

U.S. PATENT DOCUMENTS 5,693,611 A * 12/1997 Henle et al. ..................... 514/9
6,087,540 A    7/2000 Kamigauchi et al. ........ 568/643
6,562,817 B1 * 5/2003 Tanimoto et al. ......... 514/233.8

FOREIGN PATENT DOCUMENTS

| EP | 0 933 346 A1 | 8/1999 |
| EP | 0 993 346 A1 | 8/1999 |
| EP | 1 052 238 A1 | 11/2000 |
| WO | 97/39999 A1 | 10/1997 |
| WO | 98/04508 A1 | 2/1998 |
| WO | WO 98/24766 * | 6/1998 |
| WO | 99/38829 A1 | 8/1999 |

OTHER PUBLICATIONS

Woodfolk et al., PubMed Abstract (Int Arch Allergy Immunol 129(4):277-85), Dec. 2002.*
Elias, Airway Remodeling in Asthma, Am. J. Respir. Crit. Care Med. vol. 161, pp. S168-171, 2000.*
Jaffar et al., PubMed Abstract (J. Immunol. 169(10):5997-6004), Nov. 2002.*
Ji et al., PubMed Abstract (Am J Trop Med Hyg 66(4):338-45), Apr. 2002.*
Nikkei Bio Tech., "Nikkei Bio saishin Yougo Jiten; 4$^{th}$ printing", Nikkei BP K.K. (Jun. 30, 1995), p. 644, "Helper T cell; Th".
Tomio Tada et al., "Menekigaku Yougo Jiten; 3th printing", Saishin Igakusha (Dec. 1, 1995), p. 374, "*Lupus nephritis*" p. 414, "*Myasthenia gravis*" p. 587, "*Ulcerative colitis*".
Kamigauchi T. et al. "Terprenins, Novel Immunosuppressants Produced by *Aspergillus candidus*", The Journal of Antibiotics, vol. 51, No. 4, pp. 445-450, Apr. 1998.
Kamugauchi et al., "Terprenins, Novel Immunosuppressants Produced by Aspergillus candidus", The Journal of Antibiotics, vol. 51, No. 4, pp. 445-450 (1998).

* cited by examiner

*Primary Examiner*—Deepak Rao
(74) *Attorney, Agent, or Firm*—Birch, Stewart, Kolasch & Birch, LLP

(57) ABSTRACT

The present invention provides a pharmaceutical composition for use as a Th2 differentiation inhibitor comprising a compound represented by Formula (I):

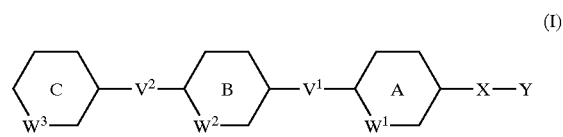

wherein each of ring A, ring B and ring C is an aromatic carbocyclic ring, a heterocyclic ring and the like, X is a single bond, —O—, —CH$_2$—, —NH—, —SO— and the like, Y is hydrogen, optionally substituted lower alkyl, optionally substituted lower alkenyl and the like, each of V$^1$ and V$^2$ is a single bond, —O—, —NH—, —OCH$_2$— and the like, a prodrug, pharmaceutically acceptable salt or solvate thereof.

16 Claims, No Drawings

TH2 DIFFERENTIATION INHIBITORS

This application is the national phase under 35 U.S.C. § 371 of PCT International Application No. PCT/JP00/04725 which has an International filing date of Jul. 14, 2000, which designated the United States of America.

TECHNICAL FIELD

The present invention relates to agents for inhibiting the differentiation from Th0 cells to Th2 cells which comprises a tricyclic compound.

BACKGROUND ART

CD4* helper T cells (hereinafter referred to as Th cells) involved in the onset of allergic diseases or autoimmune diseases are classified based on the type of the cytokines they produce into two types, namely, type I helper T cells (hereinafter referred to as Th1 cells) and type II helper T cells (hereinafter referred to as Th2 cells). Th1 cells produce IL-2, IFN-γ, TNF-β and the like, whereby inducing a cellular immunity. On the other hand, Th2 cells produce IL-4, IL-5, IL-6, IL-10, IL-13 and the like, whereby inducing a humoral immunity.

Th0 cells which are common precursors for Th1 cells and Th2 cells are differentiated into either Th1 cells or Th2 cells in response to an antigenic stimulation and then becomes mature. For example, a bacterium such as *Bacillus* tuberculosis and a virus such as an influenza virus are known to induce the differentiation to Th1 cells, while allergens such as a mite and a pollen are known to induce the differentiation to Th2 cells.

Recently, it has been reported that a polarized existence of Th1 cells and Th2 cells in a body is involved greatly in a prevention of infection and induction of allergic diseases or autoimmune diseases, and it is expected that inhibiting an excessive differentiation to Th2 cells serve to give a therapeutic effect against allergic diseases or autoimmune diseases induced by Th2 cells.

A compound having a backbone analogous to that of the present invention and having an immunosuppressive effect or an antiallergic effect is disclosed for example in WO94/27980, WO95/13067, WO96/15123, WO95/15318, WO96/40659, WO96/40143, WO96/38412, WO96/10012, WO97/24356, WO97/27181, WO97/24324, WO97/39999, WO97/44333, WO97/46524, WO98/04508, WO98/24766, WO98/24782, WO98/56785, FR2301250, U.S. Pat. No. 5,593,991, JP 47-7368 B, JP 51-91259 A, JP8-3163 A, JP 9-124571 A, JP 9-71564 A, JP9-124571 A, JP11-79993 A, Bioorganic & Medicinal Chemistry Letters, Vol. 5, No. 18, p2143-2146 (1995), J. Med. Chem., 1974, Vol. 17 and No. 11, 1177–1181.

DISCLOSURE OF INVENTION

An objective of the invention is to provide excellent Th2 differentiation inhibitors.

The present invention provides

[1] A pharmaceutical composition for use as a Th2 differentiation inhibitor comprising a compound represented by Formula (1):

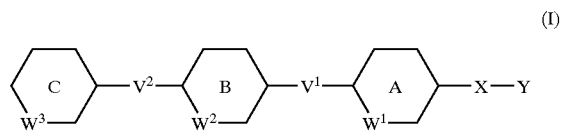

wherein each of ring A, ring B and ring C is independently an optionally substituted aromatic carbocyclic ring or an optionally substituted 5- or 6-membered heterocyclic ring which may be fused with a benzene ring, and when ring A, ring B and/or ring C is an optionally substituted 5-membered heterocyclic ring, $W^1$, $W^2$ and/or $W^3$ is a bond;

X is a single bond, —O—, —$CH_2$—, —NR'— (wherein $R^1$ is hydrogen, optionally substituted lower alkyl, lower alkenyl or lower alkylcarbonyl) or —S(O)-p- wherein p is an integer of 0 to 2;

Y is hydrogen, optionally substituted lower alkyl, optionally substituted lower alkoxy, optionally substituted lower alkenyl, optionally substituted lower alkynyl, optionally substituted acyl, optionally substituted cycloalkyl, optionally substituted cycloalkenyl, optionally substituted lower alkoxycarbonyl, optionally substituted sulfamoyl, optionally substituted amino, optionally substituted aryl or optionally substituted 5- or 6-membered heterocyclyl; $R^1$ and Y taken together may form —$(CH_2)m$-, —$(CH_2)_2$—T—$(CH_2)_2$— wherein T is O, S or NR', —CR'=CH—CH=CR'—, —CH=N—CH=CH—, —N=CH—N=CH—, —C(=O)—O—$(CH_2)_r$—, —C(=O)—NR'—$(CH_2)_r$— or —C(=O)—NR'—N=CH— wherein m is 4 or 5, r is 2 or 3 and R' is hydrogen, lower alkyl or lower alkenyl;

Y may be halogen when X is —$CH_2$— or —NR'— and

Y may be optionally substituted lower alkylsulfonyl or optionally substituted arylsulfonyl when X is —O— or —$NR^1$—;

one of $V^1$ and $V^2$ is a single bond and the other is —O—, —NH—, —$OCH_2$—, —$CH_2O$—, —CH=CH—, —C≡C—, —$CH(OR^2)$— wherein $R^2$ is hydrogen or lower alkyl, —CO—, —$NHCHR^3$— or —$CHR^3NH$— wherein $R^3$ is hydrogen or hydroxy, or a prodrug, pharmaceutically acceptable salt or solvate thereof,

[2] The pharmaceutical composition for use as a Th2 differentiation inhibitor as described in [1] wherein X is —O— or —NR'— wherein $R^1$ is hydrogen, lower alkyl or lower alkenyl,

[3] The pharmaceutical composition for use as a Th2 differentiation inhibitor as described in [1] wherein Y is optionally substituted lower alkyl or optionally substituted lower alkenyl,

[4] The pharmaceutical composition for use as a Th2 differentiation inhibitor as described in [1] wherein both of $V^1$ and $V^2$ are single bonds,

[5] A pharmaceutical composition for use as a Th2 differentiation inhibitor comprising a compound represented by Formula (Ia):

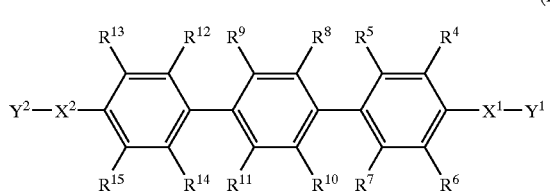

wherein each of $R^4$, $R^5$, $R^6$, $R^7$, $R^8$, $R^9$, $R^{10}$, $R^{11}$, $R^{12}$, $R^{13}$, $R^{14}$ and $R^{15}$ is independently hydrogen, halogen, hydroxy optionally substituted lower alkyl, optionally substituted lower alkoxy, carboxy or lower alkoxycarbonyl;

each of $X^1$ and $X^2$ is independently —O—, —$CH_2$— or —NH—;

each of $Y^1$ and $Y^2$ is independently optionally substituted lower alkyl, optionally substituted arylalkyl or optionally substituted lower alkenyl, or a prodrug, pharmaceutically acceptable salt or solvate thereof,

[6] A pharmaceutical composition for use as a Th2 differentiation inhibitor comprising a compound represented by Formula (Ib):

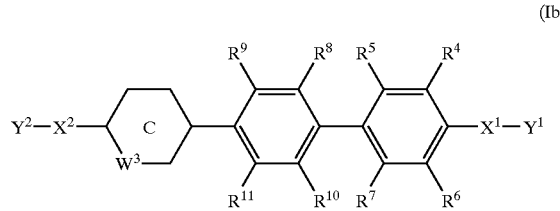

wherein ring C is an optionally substituted 5- or 6-membered heterocyclic ring containing 1 or 2 hetero atoms, and when ring C is a 5-membered heterocyclic ring, $W^3$ is a bond and other symbols have the meanings defined in [5], or a prodrug, pharmaceutically acceptable salt or solvate thereof,

[7] A pharmaceutical composition for use as a Th2 differentiation inhibitor comprising a compound represented by Formula (Ic):

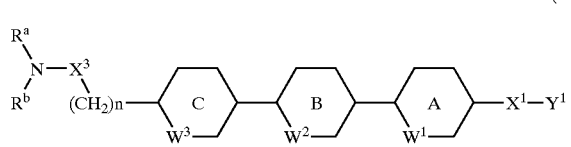

wherein each of ring A, ring B and ring C is independently an optionally substituted benzene ring or an optionally substituted 5- or 6-membered heterocyclic ring containing 1 or 2 heteroatoms, and when ring A, ring B and/or ring C is an optionally substituted 5-membered heterocyclic ring, $W^1$, $W^2$ and/or $W^3$ is a bond;

$X^1$ and $Y^1$ have the meanings defined in [5];

$X^3$ is —O— or —NH—;

each of $R^a$ and $R^b$ is independently hydrogen, optionally substituted lower alkyl, optionally substituted lower alkenyl, optionally substituted aryl, optionally substituted cycloalkyl, optionally substituted acyl, optionally substituted lower alkoxycarbonyl or optionally substituted lower alkylsulfonyl, or they are taken together to form $R^c R^d C=$ or —$(CR^e R^f)s$—;

each of $R^c$ and $R_d$ is independently hydrogen, optionally substituted lower alkyl, optionally substituted lower alkenyl, optionally substituted lower alkynyl, optionally substituted lower alkoxy, optionally substituted lower alkylthio, optionally substituted lower alkenyl oxy, optionally substituted lower alkynyloxy, optionally substituted cycloalkyl, optionally substituted aryl or optionally substituted 5- or 6-membered heterocyclyl or they are taken together with a carbon atom to which they are attached to form optionally substituted cycloalkylidene;

each $R^e$ is independently hydrogen, lower alkyl, lower alkoxy or amino, and each $R^f$ is independently hydrogen, lower alkyl, lower alkoxy or amino;

n is an integer of 0 to 2 and s is an integer of 2 to 6, or a prodrug, pharmaceutically acceptable salt or solvate thereof,

[8] The pharmaceutical composition for use as a Th2 differentiation inhibitor as described in [1], [2], [3], [4] or [7] wherein ring A is an optionally substituted benzene ring,

[9] The pharmaceutical composition for use as a Th2 differentiation inhibitor as described in [1], [2], [3], [4] or [7] wherein ring B is an optionally substituted benzene ring,

[10] The pharmaceutical composition for use as a Th2 differentiation inhibitor as described in [1], [2], [3], [4], [6] or [7] wherein ring C is an optionally substituted benzene ring, an optionally substituted pyridine ring, an optionally substituted pyrimidine ring, an optionally substituted pyridazine ring or an optionally substituted pyrazine ring,

[11] The pharmaceutical composition for use as a Th2 differentiation inhibitor as described in [5] or [6] wherein one of $R^4$ and $R^5$ is hydrogen, hydroxy or lower alkyl and the other is hydrogen or halogen, and both of $R^6$ and $R^7$ are hydrogens,

[11-2] The pharmaceutical composition for use as a Th2 differentiation inhibitor as described in [5] or [6] wherein one of $R^4$ and $R^5$ is hydrogen and the other is halogen, and both of $R^6$ and $R^7$ are hydrogens,

[12] The pharmaceutical composition for use as a Th2 differentiation inhibitor as described in [5] or [6] wherein each of $R^8$ and $R^{11}$ is independently hydrogen, hydroxy, lower alkyl or lower alkoxycarbonyl, and each of $R^9$ and $R^{10}$ is independently hydroxy, lower alkyl, lower alkoxy or lower alkoxycarbonyl,

[13] The pharmaceutical composition for use as a Th2 differentiation inhibitor as described in [5] wherein each of $R^{12}$, $R^{13}$, $R^{14}$ and $R^{15}$ is independently hydrogen or halogen,

[14] The pharmaceutical composition for use as a Th2 differentiation inhibitor as described in [5] or [6] wherein one of $X^1$ and $X^2$ is —O— and the other is —NH—,

[15] The pharmaceutical composition for use as a Th2 differentiation inhibitor as described in [5] or [6] wherein each of $Y^1$ and $Y^2$ is independently optionally halogen-substituted lower alkyl or optionally halogen-substituted lower alkenyl,

[16] The pharmaceutical composition for use as a Th2 differentiation inhibitor as described in [5] or [6] wherein one of —$X^1$—$Y^1$ and —$X^2$—$Y^2$ is prenylamino and the other is prenyloxy,

[17] The pharmaceutical composition for use as a Th2 differentiation inhibitor as described in [6] or [7] which is a therapeutic and/or prophylactic agent against an autoimmune disease,

[18] The pharmaceutical composition for use as a Th2 differentiation inhibitor as described in any of [1] to [16] which is a therapeutic and/or prophylactic agent against ulcerative colitis, myasthenia gravis or lupus nephritis,

[19] A method for treating and/or preventing a disease caused by Th2 cells or cytokines produced by Th2 cells comprising administering the compound represented by Formula (I) according to [1] or a prodrug, pharmaceutically acceptable salt or solvate thereof,

[20] A method for inhibiting the differentiation from Th0 cells to Th2 cells comprising administering the compound represented by Formula (I) according to [1] or a prodrug, pharmaceutically acceptable salt or solvate thereof,

[21] Use of the compound represented by Formula (I) according to [1] or a prodrug, pharmaceutically acceptable salt or solvate thereof for producing a medicament for treating and/or preventing a disease caused by Th2 cells or cytokines produced by Th2 cells, and

[22] Use of the compound represented by Formula (I) according to [1] or a prodrug, pharmaceutically acceptable salt or solvate thereof for producing a medicament for inhibiting the differentiation from Th0 cells to Th2 cells.

BEST MODE FOR CARRYING OUT THE INVENTION

In the specification, the term "halogen" includes fluorine, chlorine, bromine and iodine. Those preferred especially are fluorine and chlorine.

The term "lower alkyl" includes a straight or branched alkyl having 1 to 10, preferably 1 to 8, more preferably 1 to 6 and most preferably 1 to 3 carbon atoms, such as methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl.

A substituent on "optionally substituted lower alkyl" may for example be halogen; hydroxy; lower alkoxy which may be substituted by a lower alkoxy; acyl; acyloxy; carboxy; lower alkoxycarbonyl; mercapto; lower alkylthio; amino which may be substituted by hydroxy, lower alkyl or optionally substituted acyl; imino which may be substituted by hydroxy, lower alkoxy, carboxy-lower alkoxy, aryl-lower alkoxy or 5- or 6-membered heterocyclyl; hydrazono which may be substituted by carbamoyl or lower alkoxycarbonyl; hydrazino which may be substituted by lower alkyl, lower alkenyl, optionally substituted lower alkylidene or cycloalkylidene; aminooxy which may be substituted by lower alkyl, lower alkenyl, optionally substituted lower alkylidene or cycloalkylidene; carbamoyl which may be substituted by lower alkyl or amino; thiocarbamoyl which may be substituted by lower alkyl; cycloalkyl which may be substituted by lower alkyl or lower alkoxy; cycloalkenyl which may be substituted by lower alkyl; cyano; phenyl which may be substituted by one or more substituents selected from a group of hydroxy, lower alkyl, carboxy, lower alkoxycarbonyl or lower alkoxy; 5- or 6-membered heterocyclyl which may be substituted by lower alkyl and which may be fused with a benzene ring. These substituents may substitute at one or more of any possible positions. Those preferred especially are halogen, hydroxy; acyloxy; phenyl which may be substituted by lower alkyl or lower alkoxy; or pyridyl.

An alkyl moiety in "lower alkoxy", "lower alkoxycarbonyl", "lower alkylsulfonyl", "lower alkylsulfonyloxy", "lower alkylthio", "lower alkylamino" and "lower alkylenedioxy" has the meaning similar to the term "lower alkyl" described above.

A substituent on "optionally substituted lower alkoxy", "optionally substituted lower alkoxycarbonyl", "optionally substituted lower alkylsulfonyl" and "optionally substituted lower alkylthio" may for example be a halogen; hydroxy; lower alkoxy which may be substituted by acyloxy; acyl; acyloxy which may be substituted by hydroxy or carboxy; carboxy; lower alkoxycarbonyl; lower alkylthio; amino which may be substituted by lower alkyl; phenyl which may be substituted by lower alkyl or lower alkoxy; heterocyclyl; a heterocyclylcarbonyloxy. These substituents may substitute at one or more of any possible positions.

The term "lower alkylidene" includes a divalent hydrocarbon group having 1 to 10, preferably 1 to 6, more preferably 1 to 3 carbon atoms, and those may typically be exemplified are methylidene, ethylidene, propylidene, isopropylidene, butylidene, pentylidene, hexylidene, heptylidene, octylidene, nonylidene and decylidene.

A substituent on "optionally substituted lower alkylidene" may for example be optionally substituted lower alkenyl, optionally substituted lower alkoxy, optionally substituted lower alkylthio, optionally substituted cycloalkyl, optionally substituted aryl or optionally substituted 5- or 6-membered heterocyclyl. Those preferred are lower alkenyl, lower alkoxy, cycloalkyl, phenyl or 5- or 6-membered heterocyclyl. These substituents may substitute at one or more of any possible positions.

The term "lower alkenyl" includes straight or branched alkenyl having one or more double bonds at any positions and 2 to 10, preferably 2 to 8, more preferably 3 to 6 carbon atoms. Those exemplified typically are vinyl, propenyl (2-propenyl, isopropenyl and the like), butenyl, isobutenyl, prenyl, butadienyl, pentenyl, isopentenyl, pentadienyl, hexenyl, isohexenyl, hexadienyl, heptenyl, octenyl, nonenyl and decenyl.

A substituent on "optionally substituted lower alkenyl" is similar to a substituent on "optionally substituted lower alkoxy" described above. Lower alkenyl may be substituted by these substituents at one or more of any possible positions. Those preferred especially are one substituted by halogen or an unsubstituted group.

A lower alkenyl moiety in "lower alkenyloxy", "lower alkenyloxycarbonyl" and "lower alkenylamino" is similar to that in "lower alkenyl" described above.

A substituent on "optionally substituted lower alkenyloxy", "optionally substituted lower alkenyloxycarbonyl" and "optionally substituted lower alkenylthio" is similar to a substituent on "optionally substituted lower alkoxy" described above. These substituents may substitute at one or more of any possible positions.

The term "lower alkynyl" includes straight or branched alkynyl having 2 to 10, preferably 2 to 8 and more preferably 3 to 6 carbon atoms, and those exemplified typically are ethynyl, propynyl (2-propynyl and the like), butynyl (2-butynyl and the like), pentynyl, hexynyl, heptynyl, octynyl, nonynyl and decynyl. Any of these groups has one or more triple bonds at any positions, optionally with one or more double bonds.

A substituent on "optionally substituted lower alkynyl" is similar to a substituent on "optionally substituted lower alkoxy" described above. These substituents may substitute at one or more of any possible positions.

The term "acyl" includes straight or branched aliphatic acyl having 1 to 20, preferably 1 to 15, more preferably 1 to 8, further preferably 1 to 6 and most preferably 1 to 4 carbon atoms, alicyclic acyl having 4 to 9, preferably 4 to 7 carbon atoms, and aroyl. Those exemplified typically are formyl, acetyl, propionyl, butyryl, isobutyryl, valeryl, pivaloyl, hexanoyl, acryloyl, propyoloyl, methacryloyl, crotonoyl, cyclopropylcarbonyl, cyclohexylcarbonyl, cyclooctylcarbonyl and benzoyl.

The term "aroyl" means aromatic carbocyclic carbonyl and aromatic heterocyclylcarbonyl.

A substituent on "optionally substituted acyl" is similar to a substituent on "optionally substituted lower alkoxy", and alicyclic acyl and aroyl may further contain lower alkyl as their substituent. These substituents may substitute at one or more of any possible positions. An especially preferred substituent is halogen.

An acyl moiety on "acyloxy" is similar to "acyl" described above. A substituent on "optionally substituted acyloxy" is also similar as in the case of "optionally substituted acyl" described above, and these substituents may substitute at one or more of any possible positions.

The term "lower alkylcarbonyl" includes aliphatic acyl having 2 to 4 carbon atoms, such as acetyl, propionyl, butyryl and isobutyryl. Acetyl is preferred especially.

The term "cycloalkyl" includes a carbocyclic group having 3 to 6 carbon atoms, such as cyclopropyl, cyclobutyl, cyclopentyl and cyclohexyl.

A substituent on "optionally substituted cycloalkyl" may for example be lower alkyl, halogen, hydroxy, carboxy, lower alkoxycarbonyl, lower alkoxy, lower alkylenedioxy, imino which may be substituted by lower alkoxy an aryl or 5- or 6-membered heterocyclyl, which may substitute at one or more of any possible positions.

The term "cycloalkenyl" includes a group having one or more double bonds at any positions in a cycloalkyl ring described above, and those exemplified typically are cyclopropenyl, cyclobutenyl, cyclopentenyl, cyclohexenyl and cyclohexadienyl.

A substituent on "optionally substituted cycloalkenyl" is similar to a substituent on "cycloalkyl" described above. These substituents may substitute at one or more of any possible positions.

The term "cycloalkylidene" includes a divalent carbocyclic group having 3 to 6 carbon atoms such as cyclopropylidene, cyclobutylidene, cyclopentylidene and cyclohexylidene.

A substituent on "optionally substituted cycloalkylidene" is similar to a substituent on "cycloalkyl" described above, and such substituents may substitute at one or more of any possible positions. Unsubstituted cycloalkylidene is preferred.

A substituent on "optionally substituted amino" may for example be optionally substituted lower alkyl (a substituent referred here means to be lower alkoxy, cycloalkyl, optionally substituted amino (a substituent is aroyl which may be substituted by an acyloxy-lower alkoxy), optionally substituted aryl (a substituent is lower alkyl, lower alkoxy carboxy, lower alkoxycarbonyl) or heterocyclyl); lower alkenyl; lower alkynyl; cycloalkyl; aryl which may be substituted by lower alkyl, carboxy, acyl or lower alkoxycarbonyl; sulfamoyl which may be substituted by lower alkyl; optionally substituted lower alkoxycarbonyl (a substituent referred here means to be halogen, acyloxy, hydroxy-substituted acyloxy, carboxy-substituted acyloxy or heterocyclylcarbonyloxy); lower alkylsulfonyl and the like. These substituents may substitute at one or more of any possible positions.

The term "optionally substituted carbamoyl" includes carbamoyl which may be substituted by one or more groups selected from lower alkyl, lower alkenyl, lower alkynyl and the like.

The term "optionally substituted sulfamoyl" includes sulfamoyl which may be substituted by one or more groups selected from lower alkyl, lower alkenyl, lower alkynyl and the like.

The term "aromatic carbocyclic ring" is a monocyclic or polycyclic aromatic carbocyclic ring, such as a benzene ring, a naphthalene ring, an anthracene ring and a phenanthrene ring. A benzene ring is preferred especially. An "aromatic carbocyclic ring" may also be fused with one or more other carbocyclic rings, and thus includes an indane ring, an indene ring and a dihydronaphthalene ring.

The term "aryl" is a group formed by deleting one hydrogen from a monocyclic or polycyclic aromatic carbocyclic ring, such as phenyl, naphthyl, anthryl and phenanthryl. One preferred especially is phenyl. "Aryl" may also be fused with one or more other carbocyclic rings, and may have a bond in the carbocyclic ring with which it is fused. For example, indanyl, indenyl and dihydronaphthyl are included.

A substituent on "optionally substituted aromatic carbocyclic ring" and "optionally substituted aryl" may for example be halogen; hydroxy; lower alkyl which may be substituted by halogen or carboxy; lower alkoxy which may be substituted byhalogen, aryl, heteroaryl or lower alkoxy; lower alkenyl; lower alkynyl; cycloalkyl; lower alkenyloxy; lower alkynyloxy; cycloalkoxy; acyl; acyloxy; carboxy; lower alkoxycarbonyl; lower alkenyloxycarbonyl; lower alkylthio; lower alkynylthio; amino which may be substituted by lower alkyl, cycloalkyl-lower alkyl, aryl-lower alkyl, heteroaryl-lower alkyl, lower alkenyl, cycloalkyl, optionally halogen-substituted acyl, lower alkoxycarbonyl or lower alkylsulfonyl; hydrazino which may be substituted by lower alkyl, lower alkenyl, optionally substituted lower alkylidene or cycloalkylidene; aminooxy which may be substituted by lower alkyl, lower alkenyl, optionally substituted lower alkylidene or cycloalkylidene; guanidino; nitro; lower alkylsulfonyl; dihydroxyboryl; lower alkylsulfonyloxy which may be substituted by halogen; arylsulfonyl; arylsulfonyloxy; aryl; or a 5- or 6-membered heterocyclic group. These may substitute at one or more of any possible positions. Those exemplified preferably are halogen; hydroxy; lower alkyl which may be substituted by halogen; lower alkoxy which may substituted by aryl or lower alkoxy; lower alkenyloxy; acyloxy; lower alkylthio; amino which may be substituted by lower alkyl, lower alkenyl, optionally halogen-substituted acyl or lower alkylsulfonyl; nitro; lower alkylsulfonyl; lower alkylsulfonyloxy which may substituted by halogen; or arylsulfonyloxy.

An aryl moiety in "arylsulfonyl" and "arylsulfonyloxy" is similar to "aryl" described above, with phenyl being preferred especially.

A substituent on "optionally substituted arylsulfonyl" is similar to substituent on "optionally substituted aryl" described above, and may substitute at one or more of any possible positions. An unsubstituted group is preferred especially.

A "5- or 6-membered heterocyclic ring" includes a 5- or 6-membered heterocyclic ring having 1 or more heteroatoms selected from O, S and N, and may typically be an aromatic heterocyclic ring such as pyrrole, imidazole, pyrazole, pyridine, pyridazine, pyrimidine, pyrazine, triazole, triazine, isoxazole, oxazole, oxadiazole, isothiazole, thiazole, thiadiazole, furan and thiophene rings as well as a non-aromatic heterocyclic ring such as tetrahydropyran, dihydropyridine, dihydropyridazine, dihydropyrazine, dioxane, oxathiolane, thiane, pyrrolidine, pyrroline, imidazolidine, imidazoline, pyrazolidine, pyrazoline, piperidine, piperazine and morpholine rings.

A "5- or 6-membered heterocyclic ring" represented by ring A, ring B or ring C is preferably a pyridine ring and a pyrimidine ring each having a bond at 2- and 5-positions, respectively.

The term "5- or 6-membered heterocyclic ring having one or two heteroatoms" includes an aromatic heterocyclic ring such as pyrrole, imidazole, pyrazole, pyridine, pyridazine, pyrimidine, pyrazine, isoxazole, oxazole, isothiazole, thiazole, furan and thiophene rings as well as a non-aromatic heterocyclic ring such as dioxane, oxathiolane, thiane, dihydropyridine, pyrrolidine, pyrroline, imidazolidine, imidazolne, pyrazolidine, pyrazoline, piperidine, piperazine and morpholine rings among a "5- or 6-membered heterocyclic ring". An aromatic heterocyclic ring is preferred especially.

A "5- or 6-membered heterocyclic group" represented by Y and Y' is preferably 4-pyridyl, 2-furyl, 3-furyl, 2-thienyl, 3-thienyl, 1,2-dihydropyridin-5-yl, 2,3-dihydropyridazin-6-yl, 1,2-dihydropyrazin-5-yl and the like.

A "5- or 6-membered heterocyclic ring which may be fused with a benzene ring" may for example be indole, isoindole, benzimidazole, indazole, cinnoline, phthalazine, quinazoline, benzisoxazole, benzoxazole, benzoxadiazole, benzothiazole, benzisothiazole, benzofuran, benzothiophene, benzotriazole, isobenzofuran, indoline, isoindoline and chromene rings. Each of these may have a bond in a fusing heterocyclic ring.

A substituent on an "optionally substituted 5- or 6-membered heterocyclic ring" and an "optionally substituted 5- or 6-membered heterocyclic ring which may be fused with a benzene ring" may for example be halogen; hydroxy; lower alkyl which may be substituted by hydroxy or acyloxy; lower alkoxy which may be substituted by halogen, aryl ora 5- or 6-membered heterocyclic group; lower alkenyl; lower alkenyloxy; lower alkynyl; lower alkynyloxy; acyloxy; carboxy; lower alkoxycarbonyl; mercapto; lower alkylthio; lower alkenylthio; amino which may be mono- or di-substituted by halogen, optionally substituted lower alkyl (a substituent is cycloalkyl or a 5- or 6-membered heterocyclic group), optionally halogen-substituted acyl, lower alkenyl, cycloalkyl or lower alkylsulfonyl; imino which may be substituted by lower alkylsulfonyl; hydrazino which may be substituted by lower alkyl, lower alkenyl, optionally substituted lower alkylidene or cycloalkylidene; aminooxy which may be substituted by lower alkyl, lower alkenyl, optionally substituted lower alkylidene or cycloalkylidene; nitro; lower alkylsulfonyl; aryl; a 5- or 6-membered heterocyclic group; oxo; or oxide, each of which may substitute at one or more of any possible positions.

While a substituent on an "optionally substituted 5- or 6-membered heterocyclic ring containing 1 or 2 heteroatoms" is similar to those described above, one which is substituted by lower alkyl or which is unsubstituted is preferred.

The expression "when ring A, ring B and/or ring C is an optionally substituted 5-membered heterocyclic ring, $W^1$, $W^2$ and/or $W^3$ is a bond" means that when ring A is a 5-membered heterocyclic ring, $W^1$ is a bond to give the positions where $V^1$ and X are bound to ring A represented by the formula:

Similarly, when ring B or ring C is a 5-membered heterocyclic ring, $W^2$ or $W^3$ is a bond to give the positions where $V^1$ and $V^2$ are bound represented by the formula:

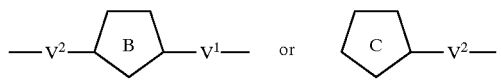

Each of X, $V^1$ and $V^2$ may directly be bound to a heteroatom which is a constituent of ring A, ring B and ring C, respectively.

The expression "$R^a$ and $R^b$ are taken together to form —$(CR^eR^f)s$-" means that $R^a$ and $R^b$ are taken together with nitrogen atom to which they are attached to form optionally substituted nitrogen-containing saturated heterocyclic ring, including, for example, optionally substituted aziridine, optionally substituted azetidine, optionally substituted pyrrolidine, optionally substituted piperidine and optionally substituted perhydroazepine (a substituent here denotes lower alkyl, lower alkoxy or amino). Each of a plural of $R^e$ and $R^f$ is independently hydrogen, lower alkyl, lower alkoxy or amino, typically including —$(CH_2)_2$—, —$(CH_2)_3$—, —$CH(Me)(CH_2)_3$—, —$CH_2CH(OMe)(CH_2)_3$—, —$(CH_2)_3CH(NH_2)(CH_2)_2$— and the like.

Th2 differentiation inhibitors of the invention may include a pharmaceutically acceptable salt of Compound (1). Such pharmaceutically acceptable salt may for example be a salt of a mineral acid such as hydrochloric acid, sulfuric acid, nitric acid, phosphoric acid, hydrofluoric acid and a hydrobromic acid; a salt of an organic acid such as formic acid, acetic acid, tartaric acid, lactic acid, citric acid, fumaric acid, maleic acid and succinic acid; a salt of an organic base such as ammonium, trimethylammonium and triethylammonium; a salt of an alkaline metal such as sodium and potassium as well as a salt of an alkaline earth metal such as calcium and magnesium.

Th2 differentiation inhibitors of the invention include a solvate (preferably a hydrate) of Compound (I). Such solvate may for example be a solvate with an organic solvent and/or water. When a hydrate is formed, a desired number of water molecules may be coordinated.

Th2 differentiation inhibitors of the invention include all stereoisomers (for example an atropic isomer and the like) of Compound (I).

While any Compound (I) has a Th2 differentiation inhibiting effect, those preferred especially are listed below.

Compounds represented by Formula (I) wherein:
1) ring A is an optionally substituted aromatic carbocyclic ring or an optionally substituted 5- or 6-membered heterocyclic ring (hereinafter expressed as "ring A is A-1");
ring A is an optionally substituted benzene ring or an optionally substituted 6-membered heterocyclic ring (hereinafter expressed as "ring A is A-2");
ring A is an optionally substituted benzene ring (hereinafter expressed as "ring A is A-3");
ring A is a benzene ring which may have a substituent (halogen, hydroxy, lower alkyl, lower alkoxy, carboxy or lower alkoxycarbonyl) (hereinafter expressed as "ring A is A-4");

ring A is a benzene ring which may have a substituent (halogen, hydroxy or lower alkoxy) (hereinafter expressed as "ring A is A-5");

ring A is a benzene ring which may be substituted with halogen (hereinafter expressed as "ring A is A-6");

2) ring B is an optionally substituted aromatic carbocyclic ring or an optionally substituted 5- or 6-membered heterocyclic ring (hereinafter expressed as "ring B is B-1");

ring B is an optionally substituted benzene ring or an optionally substituted 6-membered heterocyclic ring (hereinafter expressed as "ring B is B-2");

ring B is an optionally substituted benzene ring (hereinafter expressed as "ring B is B-3");

ring A is a benzene ring which may have a substituent (halogen, hydroxy, optionally substituted lower alkyl, optionally substituted lower alkoxy or optionally substituted lower alkoxycarbonyl) (hereinafter expressed as "ring B is B-4");

ring B is a benzene ring which may have a substituent (hydroxy, lower alkyl, lower alkoxy or lower alkoxycarbonyl) (hereinafter expressed as "ring B is B-5"); ring B is a group selected from:

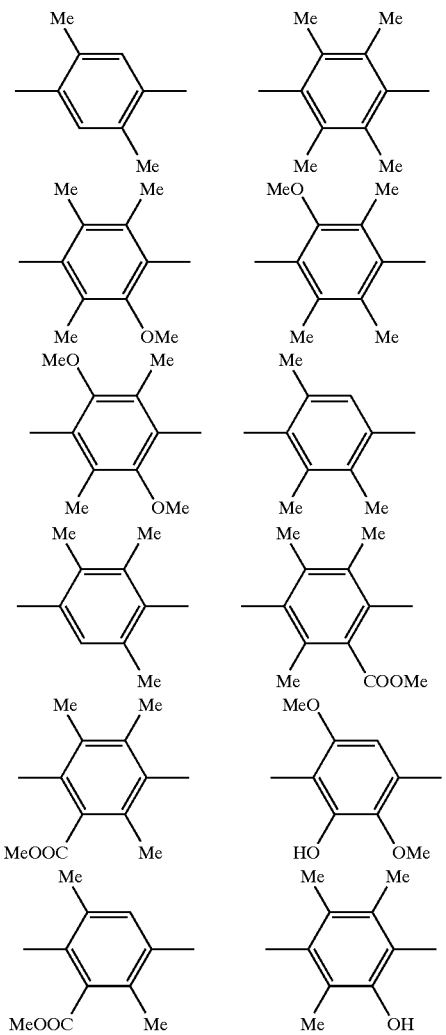

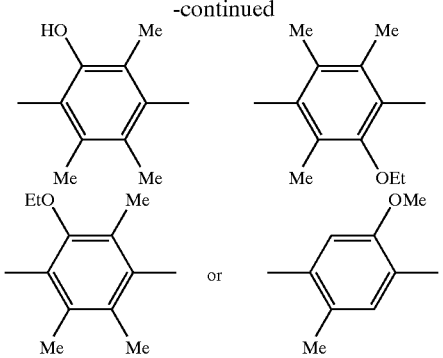

(hereinafter expressed as ring "B is B-6");

3) ring C is an optionally substituted aromatic carbocyclic ring or an optionally substituted 5- or 6-membered heterocyclic ring (hereinafter expressed as "ring C is C-1");

ring C is an optionally substituted benzene ring or an optionally substituted 6-membered heterocyclic ring containing 1 or 2 heteroatoms (hereinafter expressed as "ring C is C-2");

ring C is an optionally substituted benzene ring, an optionally substituted pyridine ring, an optionally substituted pyrimidine ring, an optionally substituted pyridazine ring or an optionally substituted pyrazine ring (hereinafter expressed as "ring C is C-3");

ring C is a benzene ring, a pyridine ring, a pyrimidine ring, a pyridazine ring or a pyrazine ring (which may be substituted by halogen, lower alkyl lower alkoxy; lower alkenyloxy or lower alkenylamino) (hereinafter expressed as "ring C is C-4");

ring C is a benzene ring or a pyridine ring (which may be substituted by halogen, lower alkyl, lower alkoxy, lower alkenyloxy or lower alkenylamino) (hereinafter expressed as "ring C is C-5");

4) X is —O—, —CH$_2$— or —NR$^1$—wherein R$^1$ is hydrogen or optionally substituted lower alkyl (hereinafter expressed as "X is X-1");

X is —O—, —CH$_2$—or —NH— hereinafter expressed as "X is X-2");

X is —O— or —NH— (hereinafter expressed as "X is X-3") or

X is —NH— (hereinafter expressed as "X is X-4");

5) Y is hydrogen, optionally substituted lower alkyl, optionally substituted lower alkenyl or optionally substituted cycloalkyl (hereinafter expressed as "Y is Y-1");

Y is hydrogen, lower alkyl, arylalkyl, lower alkenyl or cycloalkyl (hereinafter expressed as "Y is Y-2");

Y is lower alkyl, benzyl or lower alkenyl (hereinafter expressed as "Y is Y-3");

Y is prenyl (hereinafter expressed as "Y is Y-4");

6) both of V$^1$ and V$^2$ are single bonds;

7) ring A, ring B, ring C, X and Y are in any of the combinations shown below and both of V$^1$ and V$^2$ are single bonds.

(A-3, B-3, C-2, X-2, Y-1), (A-3, B-3, C-2, X-2, Y-3), (A-3, B-3, C-2, X-2, Y-4), (A-3, B-3, C-2, X-3, Y-1), (A-3, B-3, C-2, X-3, Y-3), (A-3, B-3, C-2, X-3, Y-4), (A-3, B-3, C-4, X-2, Y-1), (A-3, B-3, C-4, X-2, Y-3), (A-3, B-3, C-4, X-2, Y-4), (A-3, B-3, C-4, X-3, Y-1), (A-3, B-3, C-4, X-3, Y-3), (A-3, B-3, C-4, X-3, Y-4), (A-3, B-3, C-5, X-2, Y-1), (A-3, B-3, C-5, X-2, Y-3), (A-3, B-3, C-5, X-2, Y-4), (A-3, B-3, C-5, X-3, Y-1), (A-3, B-3, C-5, X-3, Y-3), (A-3, B-3, C-5,

13

X-3, Y-4), (A-3, B-4, C-2, X-2, Y-1), (A-3, B-4, C-2, X-2, Y-3), (A-3, B-4, C-2, X-2, Y-4), (A-3, B-4, C-2, X-3, Y-1), (A-3, B-4, C-2, X-3, Y-3), (A-3, B-4, C-2, X-3, Y-4), (A-3, B-4, C-4, X-2, Y-1), (A-3, B-4, C-4, X-2, Y-3), (A-3, B-4, C-4, X-2, Y-4), (A-3, B-4, C-4, X-3, Y-1), (A-3, B-4, C-4, X-3, Y-3), (A-3, B-4, C-4, X-3, Y-4), (A-3, B-4, C-5, X-2, Y-1), (A-3, B-4, C-5, X-2, Y-3), (A-3, B-4, C-5, X-2, Y-4), (A-3, B-4, C-5, X-3, Y-1), (A-3, B-4, C-5, X-3, Y-3), (A-3, B-4, C-5, X-3, Y-4), (A-3, B-6, C-2, X-2, Y-1), (A-3, B-6, C-2, X-2, Y-3), (A-3, B-6, C-2, X-2, Y-4), (A-3, B-6, C-2, X-3, Y-1), (A-3, B-6, C-2, X-3, Y-3), (A-3, B-6, C-2, X-3, Y-4), (A-3, B-6, C-4, X-2, Y-1), (A-3, B-6, C-4, X-2, Y-3), (A-3, B-6, C-4, X-2, Y-4), (A-3, B-6, C-4, X-3, Y-1), (A-3, B-6, C-4, X-3, Y-3), (A-3, B-6, C-4, X-3, Y-4), (A-3, B-6, C-5, X-2, Y-1), (A-3, B-6, C-5, X-2, Y-3), (A-3, B-6, C-5, X-2, Y-4), (A-3, B-6, C-5, X-3, Y-1), (A-3, B-6, C-5, X-3, Y-3), (A-3, B-6, C-5, X-3, Y-4), (A-4, B-3, C-2, X-2, Y-1), (A-4, B-3, C-2, X-2, Y-3), (A-4, B-3, C-2, X-2, Y-4), (A-4, B-3, C-2, X-3, Y-1), (A-4, B-3, C-2, X-3, Y-3), (A-4, B-3, C-2, X-3, Y-4), (A-4, B-3, C-4, X-2, Y-1), (A-4, B-3, C-4, X-2, Y-3), (A-4, B-3, C-4, X-2, Y-4), (A-4, B-3, C-4, X-3, Y-1), (A-4, B-3, C-4, X-3, Y-3), (A-4, B-3, C-4, X-3, Y-4), (A-4, B-3, C-5, X-2, Y-1), (A-4, B-3, C-5, X-2, Y-3), (A-4, B-3, C-5, X-2, Y-4), (A-4, B-3, C-5, X-3, Y-1), (A-4, B-3, C-5, X-3, Y-3), (A-4, B-3, C-5, X-3, Y-4), (A-4, B-4, C-2, X-2, Y-1), (A-4, B-4, C-2, X-2, Y-3), (A-4, B-4, C-2, X-2, Y-4), (A-4, B-4, C-2, X-3, Y-1); (A-4, B-4, C-2, X-3, Y-3), (A-4, B-4, C-2, X-3, Y-4), (A-4, B-4, C-4, X-2, Y-1), (A-4, B-4, C-4, X-2, Y-3), (A-4, B-4, C-4, X-2, Y-4), (A-4, B-4, C-4, X-3, Y-1), (A-4, B-4, C-4, X-3, Y-3), (A-4, B-4, C-4, X-3, Y-4), (A-4, B-4, C-5, X-2, Y-1), (A-4, B-4, C-5, X-2, Y-1), (A-4, B-4, C-5, X-2, Y-4), (A-4, B-4, C-5, X-2, Y-1), (A-4, B-4, C-5, X-3, Y-3), (A-4, B-4, C-5, X-3, Y-4), (A-4, B-6, C-2, X-2, Y-1), (A-4, B-6, C-2, X-2, Y-3), (A-4, B-6, C-2, X-2, Y-4), (A-4, B-6, C-2, X-3, Y-1), (A-4, B-6, C-2, X-3, Y-3), (A-4, B-6, C-2, X-3, Y-4), (A-4, B-6, C-4, X-2, Y-1), (A-4, B-6, C-4, X-2, Y-3), (A-4, B-6, C-4, X-2, Y-4), (A-4, B-6, C-4, X-3, Y-1), (A-4, B-6, C-4, X-3, Y-3), (A-4, B-6, C-4, X-3, Y-4), (A-4, B-6, C-5, X-2, Y-4), (A-4, B-6, C-5, X-2, Y-3), (A-4, B-6, C-5, X-2, Y-4), (A-4, B-6, C-5, X-2, Y-1), (A-4, B-6, C-5, X-3, Y-3), (A-4, B-6, C-5, X-3, Y-4), (A-6, B-3, C-2, X-2, Y-1), (A-6, B-3, C-2, X-2, Y-3), (A-6, B-3, C-2, X-2, Y-4), (A-6, B-3, C-2, X-3, Y-1), (A-6, B-3, C-2, X-3, Y-3), (A-6, B-3, C-2, X-3, Y-4), (A-6, B-3, C-4, X-2, Y-1), (A-6, B-3, C-4, X-2, Y-3), (A-6, B-3, C-4, X-2, Y-4), (A-6, B-3, C-4, X-3, Y-1), (A-6, B-3, C-4, X-3, Y-3), (A-6, B-3, C-4, X-3, Y-4), (A-6, B-3, C-5, X-2, Y-1), (A-6, B-3, C-5, X-2, Y-3), (A-6, B-3, C-5, X-2, Y-4), (A-6, B-3, C-5, X-3, Y-1), (A-6, B-3, C-5, X-3, Y-3), (A-6, B-3, C-5, X-3, Y-4), (A-6, B-4, C-2, X-2, Y-1), (A-6, B-4, C-2, X-2, Y-3), (A-6, B-4, C-2, X-2, Y-4), (A-6, B-4, C-2, X-3, Y-1), (A-6, B-4, C-2, X-3, Y-3), (A-6, B-4, C-2, X-3, Y-4), (A-6, B-4, C-4, X-2, Y-1), (A-6, B-4, C-4, X-2, Y-3), (A-6, B-4, C-4, X-2, Y-4), (A-6, B-4, C-4, X-3, Y-1), (A-6, B-4, C-4, X-3, Y-3), (A-6, B-4, C-4, X-3, Y-4), (A-6, B-4, C-5, X-2, Y-1), (A-6, B-4, C-5, X-2, Y-3), (A-6, B-4, C-5, X-2, Y-4), (A-6, B-4, C-5, X-3, Y-1), (A-6, B-4, C-5, X-3, Y-3), (A-6, B-4, C-5, X-3, Y-4), (A-6, B-6, C-2, X-2, Y-1), (A-6, B-6, C-2, X-2, Y-3), (A-6, B-6, C-2, X-2, Y-4), (A-6, B-6, C-2, X-3, Y-1), (A-6, B-6, C-2, X-3, Y-3, (A-6, B-6, C-2, X-3, Y-4), (A-6, B-6, C-4, X-2, Y-1), (A-6, B-6, C-4, X-2, Y-3), (A-6, B-6, C-4, X-2, Y-4), (A-6, B-6, C-4, X-3, Y-1), (A-6, B-6, C-4, X-3, Y-3), (A-6, B-6, C-4, X-3, Y-4), (A-6, B-6, C-5, X-2, Y-1), (A-6, B-6, C-5, X-2, Y-3), (A-6, B-6, C-5, X-2, Y-4), (A-6, B-6, C-5, X-3, Y-1), (A-6, B-6, C-5, X-3, Y-3), (A-6, B-6, C-5, X-3, Y-4).

14

Compounds represented by Formula (Ia) wherein:
1) a compound wherein each of $R^4$, $R^5$, $R^6$ and $R^7$ is independently hydrogen, halogen, hydroxy, lower alkyl, lower alkoxy, carboxy or lower alkoxycarbonyl (hereinafter expressed as "$R^4$ to $R^7$ are R47-1");
a compound wherein each of $R^4$, $R^5$, $R^6$ and $R^7$ is independently hydrogen or halogen (hereinafter expressed as "$R^4$ to $R^7$ are R47-2");
a compound wherein one of $R^4$ and $R^5$ is hydrogen and the other is halogen, and both of $R^6$ and $R^7$ are hydrogens (hereinafter expressed as "$R^4$ to $R^7$ are R47-3");
2) a compound wherein each of $R^8$, $R^9$, $R^{10}$ and $R^{11}$ is independently hydrogen, halogen, hydroxy, optionally substituted lower alkyl, optionally substituted lower alkoxy, carboxy or optionally substituted lower alkoxycarbonyl (hereinafter expressed as "$R^8$ to $R^{11}$ are R811-1");
a compound wherein each of $R^8$, $R^9$, $R^{10}$ and $R^{11}$ is independently hydrogen, hydroxy, lower alkyl, lower alkoxy or lower alkoxycarbonyl (hereinafter expressed as "$R^8$ to $R^{11}$ are R811-2");
a compound wherein each of $R^8$ and $R^{11}$ is independently hydrogen, hydroxy, lower alkyl or lower alkoxycarbonyl, and each of $R^9$ and $R^{10}$ is independently hydroxy, lower alkyl, lower alkoxy or lower alkoxycarbonyl (hereinafter expressed as "$R^8$ to $R^{11}$ are R811-3"); a compound wherein $R^8$ is hydrogen or lower alkyl, $R^9$ is hydroxy, lower alkyl or lower alkoxy, $R^{10}$ is hydroxy, lower alkyl, lower alkoxy or lower alkoxycarbonyl and $R^{11}$ is hydrogen, hydroxy, lower alkyl or lower alkoxycarbonyl (hereinafter expressed as "$R^8$ to $R^{11}$ are R811-4");
a compound wherein the combination of $R^8$, $R^9$, $R^{10}$ and $R^{11}$ is similar to that in B-6 described above (hereinafter expressed as "$R^8$ to $R^{11}$ are R811-5");
3) a compound wherein each of $R^{12}$, $R^{13}$, $R^{14}$ and $R^{15}$ is independently hydrogen, halogen, hydroxy, lower alkyl, lower alkoxy, carboxy or lower alkoxycarbonyl (hereinafter expressed as "$R^{12}$ to $R^{15}$ are R1215-1");
a compound wherein each of $R^{12}$, $R^{13}$, $R^{14}$ and $R^{15}$ is independently hydrogen or halogen (hereinafter expressed as "$R^{12}$ to $R^{15}$ are R1215-2");
a compound wherein all of $R^{12}$, $R^{13}$, $R^{14}$ and $R^{15}$ are hydrogens (hereinafter expressed as "$R^{12}$ to $R^{15}$ are R1215-3");
4) a compound wherein each of $X^1$ and $X^2$ is independently —O— or —NH— (hereinafter expressed as "$X^1$ and $X^2$ are X12-1");
a compound wherein one of $X^1$ and $X^2$ is —O— and the other is —NH— or both are —NH— (hereinafter expressed as "$X^1$ and $X^2$ are X12-2");
5) a compound wherein each of $Y^1$ and $Y^2$ is independently hydrogen, optionally substituted lower alkyl, optionally substituted lower alkenyl or optionally substituted cycloalkyl (hereinafter expressed as "$Y^1$ and $Y^2$ are Y12-1");
a compound wherein each of $Y^1$ and $Y^2$ is independently hydrogen, optionally halogen-substituted lower alkyl, aryl alkyl, lower alkenyl or cycloalkyl (hereinafter expressed as "$Y^1$ and $Y^2$ are Y12-2");
a compound wherein each of $Y^1$ and $Y^2$ is independently optionally halogen-substituted lower alkyl or optionally halogen-substituted lower alkenyl (hereinafter expressed as "$Y^1$ and $Y^2$ are Y12-3");
a compound wherein one of $Y^1$ and $Y^2$ is prenyl and the other is optionally halogen-substituted lower alkyl or optionally halogen-substituted lower alkenyl (hereinafter expressed as "$Y^1$ and $Y^2$ are Y12-4");

15 a compound wherein both of $Y^1$ and $Y^2$ are prenyls (hereinafter expressed as "$Y^1$ and $Y^2$ are Y12-5");

6) a compound wherein $R^4$ to $R^7$, $R^8$ to $R^{11}$, $R^{12}$ to $R^{15}$, $X^1$ and $X^2$ and $Y^1$ and $Y^2$ are in any of the combinations shown below;

(R47-1, R811-4, R1215-1, X12-1, Y12-5),
(R47-2, R811-4, R1215-2, X12-1, Y12-3), (R47-2, R811-4, R1215-2, X12-1, Y12-5), (R47-2, R811-4, R1215-2, X12-2, Y12-3), (R47-2, R811-4, R1215-2, X12-2, Y12-5), (R47-2, R811-4, R1215-3, X12-1, Y12-3), (R47-2, R811-4, R1215-3, X12-1, Y12-5), (R47-2, R811-4, R1215-3, X12-2, Y12-3), (R47-2, R811-4, R1215-3, X12-2, Y12-5), (R47-2, R811-5, R1215-2, X12-1, Y12-3), (R47-2, R811-5, R1215-2, X12-1, Y12-5), (R47-2, R811-5, R1215-2, X12-2, Y12-3), (R47-2, R811-5, R1215-2, X12-2, Y12-5), (R47-2, R811-5, R1215-3, X12-1, Y12-3), (R47-2, R811-5, R1215-3, X12-1, Y12-5), (R47-2, R811-5, R1215-3, X12-2, Y12-3), (R47-2, R811-5, R1215-3, X12-2, Y12-5), (R47-3, R811-4, R1215-2, X12-1, Y12-3), (R47-3, R811-4, R1215-2, X12-1, Y12-5), (R47-3, R811-4, R1215-21×12-2, Y12-3), (R47-3, R811-4, R1215-2, X12-2, Y12-5), (R47-3, R811-4, R1215-3, X12-1, Y12-3), R47-3, R811-4, R1215-3, X12-1, Y12-5), (R47-3, R811-4, R1215-3, X12-2, Y12-3), (R47-3, R811-4, R1215-3, X12-2, Y12-5), (R47-3, R811-5, R1215-2, X12-1, Y12-3), (R47-3, R811-5, R1215-2, X12-1, Y12-5), (R47-3, R811-5, R1215-2, X12-2, Y12-3), (R47-3, R811-5, R1215-2, X12-2, Y12-5), (R47-3, R811-5, R1215-3, X12-1, Y12-3), (R47-3, R811-5, R1215-3, X12-1, Y12-5), (R47-3, R811-5, R1215-3, X12-2, Y12-3), (R47-3, R811-5, R1215-3, X12-2, Y12-5).

Compounds represented by Formula (Ib) wherein:

1) a compound wherein each of $R^4$, $R^5$, $R^6$ and $R^7$ is R47-1, a compound wherein each of $R^4$, $R^5$, $R^6$ and $R^7$ is R47-2, a compound wherein each of $R^4$, $R_5$, $R^6$ and $R^7$ is R47-3, 2) a compound wherein each of $R^8$, $R^9$, $R^{10}$ and $R^1$ is R811-1,
a compound wherein each of $R^8$, $R^9$, $R^{10}$ and $R^{11}$ is R811-2,
a compound wherein each of $R^8$, $R^9$, $R^{10}$ and $R^{11}$ is R811-3,
a compound wherein each of $R^8$, $R^9$, $R^{10}$ and $R^{11}$ is R811-4,
a compound wherein each of $R^8$, $R^9$, $R^{10}$ and $R^{11}$ is R811-5, 3) a compound wherein ring C is C-1,
a compound wherein ring C is C-2,
a compound wherein ring C is C-3,
a compound wherein ring C is benzene, pyridine, pyrimidine, pyridazine or pyrazine (which may be substituted by halogen, lower alkyl or lower alkoxy (hereinafter expressed as "ring C is a compound wherein ring C is benzene or pyridine (which may be substituted by halogen, lower alkyl or lower alkoxy) (hereinafter expressed as "ring C is C-4"), 4) a compound wherein $X^1$ and $X^2$ are X12-1,
a compound wherein $X^1$ and $X^2$ are X12-2, 5) a compound wherein $Y^1$ and $Y^2$ are Y12-1,
a compound wherein $Y^1$ and $Y^2$ are Y12-2,
a compound wherein $Y^1$ and $Y^2$ are Y12-3,
a compound wherein $Y^1$ and $Y^2$ are Y12-4,
a compound wherein $Y^1$ and $Y^2$ are Y12-5, 6) a compound wherein $R^4$ to $R^7$, $R^8$ to $R^{11}$, ring C, $X^1$ and $X^2$ and $Y^1$ and $Y^2$ are in any of the combinations shown below;

(R47-2, R811-4, C-2, X12-1, Y12-3), (R47-2, R811-4, C-2, X12-1, Y12-5), (R47-2, R811-4, C-2, X12-2, Y12-3), R47-2, R811-4, C-2, X12-2, Y12-5), (R47-2, R811-4, C-4', X12-1, Y12-3), (R47-2, R811-4, C-4', X12-1, Y12-5), (R47-2, R811-4, C-4', X12-2, Y12-3), (R47-2, R811-4,

16

C-4', X12-2, Y12-5), (R47-2, R811-4, C-5', X12-1, Y12-3), (R47-2, R811-4, C-5', X12-1, Y12-5), (R47-2, R811-4, C-5', X12-2, Y12-0.3), (R47-2, R811-4, C-5', X12-2, Y12-5), (R47-2, R811-5, C-2, X12-1, Y12-3), (R47-2, R811-5, C-2, X12-1, Y12-5), (R47-2, R811-5, C-2, X12-2, Y12-3), (R47-2, R811-5, C-2, X12-2, Y12-5), (R47-2, R811-5, C-4', X12-1, Y12-3), (R47-2, R811-5, C-4', X12-1, Y12-5), (R47-2, R811-5, C-4', X12-2, Y12-3), (R47-2, R811-5, C-4', X12-2, Y12-5), (R47-2, R811-5, C-5', X12-1, Y12-3), (R47-2, R811-5, C-5', X12-1, Y12-5), (R47-2, R811-5, C-5', X12-2, Y12-3), (47-2, R811-5, C-5', X12-2, Y12-5), (R47-3, R811-4, C-2, X12-1, Y12-3), (R47-3, R811-4, C-2, X12-1, Y12-5), (R47-3, R811-4, C-2, X12-2, Y12-3), (R47-3, R811-4, C-2, X12-2, Y12-5), (R47-3, R811-4, C-4', X12-1, Y12-3), (R47-3, R811-4, C-4', X12-1, Y12-5), (R47-3, R811-4, C-4', X12-2, Y12-3), (R47-3, R811-4, C-4', X12-2, Y12-5), (R47-3, R811-4, C-5', X12-1, Y12-3), (R47-3, R811-4, C-5', X12-1, Y12-5), (R47-3, R811-4, C-5', X12-2, Y12-3), (R47-3, R811-4, C-5', X12-2, Y12-5), (R47-3, R8115, C-2, X12-1, Y12-3), (R47-3, R811-5, C-2, X12-1, Y12-5), (R47-3, R811-5, C-2, X12-2, Y12-3), (R47-3, R811-5, C-2, X12-2, Y12-5), (R47-3, R811-5, C-4', X12-1, Y12-3), R47-3, R811-5, C-4', X12-1, Y12-5), (R47-3, R811-5, C-4', X12-2, Y12-3), (R47-3, R811-5, C-4', X12-2, Y12-5), (R47-3, R811-5, C-5', X12-1, Y12-3), (R47-3, R811-5, C-5', X12-1, Y12-5), (R47-3, R811-5, C-5', X12-2, Y12-3), (R47-3, R811-5, C-5', X12-2, Y12-5).

Compounds represented by Formula (Ic) wherein:

1) a compound wherein ring A is A-1, a compound wherein ring A is A-2, a compound wherein ring A is A-3, a compound wherein ring A is A-4, a compound wherein ring A is A-5, a compound wherein ring A is A-6, 2) a compound wherein ring B is B-1, a compound wherein ring B is B-2, a compound wherein ring B is B-3, a compound wherein ring B is B-4, a compound wherein ring B is B-5, 3) a compound wherein ring C is C-1, a compound wherein ring C is C-2, a compound wherein ring C is C-3, a compound wherein ring C is C-4, a compound wherein ring C is C-5, 4) a compound wherein $X^1$ is —O— or —NH— (hereinafter expressed as "$X^1$ is X-1"), a compound wherein $X^1$ is —NH— (hereinafter expressed as "$X^1$ is X-2"), 5) a compound wherein $Y^1$ is Y-1, a compound wherein $Y^1$ is Y-2, a compound wherein $Y^1$ is Y-3, a compound wherein $Y^1$ is Y-4, 6) a compound wherein each of $R^a$ and $R^b$ is independently hydrogen, lower alkyl, lower alkenyl, lower alkoxycarbonyl or lower alkylsulfonyl, or they are taken together to form $R^c R^d C=$ or $—(CR^e R^f)s-$, each of $R^c$ and $R^d$ is independently hydrogen, lower alkyl, lower alkenyl, lower alkoxy, aryl or a heterocyclic group or they are taken together with a carbon atom to which they are attached to form cycloalkylidene, each $R^e$ is independently hydrogen, lower alkyl, lower alkoxy or amino, and each $R^f$ is independently hydrogen, lower alkyl, lower alkoxy or amino, and s is an integer of 2 to 6 (hereinafter expressed as "$R^a$ and $R^b$ are Rab-1");

a compound wherein each of $R^a$ and $R^b$ is independently hydrogen, alkyl having 1 to 6 carbon atoms, alkenyl having 2 to 6 carbon atoms, alkoxycarbonyl having 1 to 6 carbon atoms or alkylsulfonyl having 1 to 6 carbon atoms, or they are taken together to form $R^c R^d C=$ or $—(CR^e R^f)s-$, each of $R^c$ and $R^d$ is independently hydrogen, alkyl having 1 to 6 carbon atoms, alkenyl having 2 to 6 carbon atoms, alkoxy having 1 to 6 carbon atoms, phenyl or a 5- or 6-membered aromatic heterocyclic group or they are taken together with a carbon atom to which they are attached to form cycloalkylidene having 5 to 6 carbon atoms, each $R^e$ is independently hydrogen, alkyl having 1 to 6 carbon atoms, alkoxy having 1 to 6 carbon atoms or amino, and each $R^f$ is independently hydrogen, alkyl having 1 to 6 carbon atoms, alkoxy having 1 to 6 carbon atoms or amino, and s is an integer of 4 or 5 (hereinafter expressed as "$R^a$ and $R^b$ are Rab-2");

a compound wherein each of $R^a$ and $R^b$ is independently hydrogen, alkyl having 1 to 3 carbon atoms or alkoxycarbonyl having 1 to 4 carbon atoms, or they are taken together to form $R^cR^dC=$ or $-(CR^eR^f)s-$, each of $R^c$ and $R^d$ is independently hydrogen, alkyl having 1 to 3 carbon atoms, alkenyl having 2 to 4 carbon atoms or alkoxy having 1 to 3 carbon atoms, each $R^e$ is independently hydrogen or alkyl having 1 to 3 carbon atoms, and each $R^f$ is independently hydrogen or alkyl having 1 to 3 carbon atoms (hereinafter expressed as "$R^a$ and $R^b$ are Rab-3");

a compound wherein each of $R^a$ and $R^b$ is independently hydrogen, alkyl having 1 to 3 carbon atoms or alkoxycarbonyl having 1 to 4 carbon atoms, or they are taken together to form $R^cR_dC=$, one of $R^c$ and $R^d$ is alkyl having 1 to 3 carbon atoms and the other is hydrogen, alkyl having 1 to 3 carbon atoms or lower alkoxy having 1 to 3 carbon atoms (hereinafter expressed as "$R^a$ and $R^b$ are Rab-4");

a compound wherein $R^a$ and $R^b$ are taken together to form $R^cR^dC=$, one of $R^c$ and $R^d$ is alkyl having 1 to 3 carbon atoms and the other is alkyl having 1 to 3 carbon atoms or lower alkoxy having 1 to 3 carbon atoms (hereinafter expressed as "$R^a$ and $R^b$ are Rab-5");

7) a compound wherein n is 0 or 1 (hereinafter expressed as "n is n1");

a compound wherein n is 1 (hereinafter expressed as "n is n2");

8) a compound wherein ring A, ring B, ring C, $X^1$, $Y^1$ and $R^a$ and $R^b$ are in any of the combinations shown below and n is 0 or 1.

(A-4, B-4, C-4, X-1, Y-3, Rab-2), (A-4, B-4, C-4, X-1, Y-3, Rab-3), (A-4, B-4, C-4, X-1, Y-4, Rab-2), (A-4, B-4, C-4, X-1, Y-4, Rab-3), (A-4, B-4, C-4, X-2, Y-3, Rab-2), (A-4, B-4, C-4, X-2, Y-3, Rab-3), (A-4, B-4, C-4, X-2, Y-4, Rab-2), (A-4, B-4, C-4, X-2, Y-4, Rab-3), (A-4, B-4, C-5, X-1, Y-3, Rab-2), (A-4, B-4, C-5, X-1, Y-3, Rab-3), (A-4, B-4, C-5, X-1, Y-4, Rab-2), (A-4, B-4, C-5, X-1, Y-4, Rab-3), (A-4, B-4, C-5, X-2, Y-3, Rab-2), (A-4, B-4, C-5, X-2, Y-3, Rab-3), (A-4, B-4, C-5, X-2, Y-4, Rab-2), (A-4, B-4, C-5, X-2, Y-4, Rab-3), (A-4,1-6, C-4, X-1, Y-3, Rab-2), (A-4, B-6, C-4, X-1, Y-3, Rab-3), (A-4, B-6, C-4, X-1, Y-4, Rab-2), (A-4, B-6, C-4, X-1, Y-4, Rab-3), (A-4, B-6, C-4, X-2, Y-3, Rab-2), (A-4, B-6, C-4, X-2, Y-3, Rab-3), (A-4, B-6, C-4, X-2, Y-4, Rab-2), (A-4, B-6, C-4, X-2, Y-4, Rab-3), (A-4, B-6, C-4, X-1, Y-3, Rab-2), (A-4, B-6, C-4, X-1, Y-3, Rab-3), (A-4, B-6, C-4, X-1, Y-4, Rab-2), (A-4, B-6, C-5, X-1, Y-4, Rab-3), (A-4, B-6, C-5, X-2, Y-3, Rab-2), (A-4, B-6, C-5, X-2, Y-3, Rab-3), (A-4, B-6, C-5, X-2, Y-4, Rab-2), (A-4, B-6, C-5, X-2, Y-4, Rab-3), (A-6, B-4, C-4, X-1, Y-3, Rab-2), (A-6, B-4, C-4, X-1, Y-3, Rab-3), (A-6, B-4, C-4, X-1, Y-4, Rab-2), (A-6, B-4, C-4, X-1, Y-4, Rab-3), (A-6, B-4, C-4, X-2, Y-3, Rab-2), (A-6, B-4, C-4, X-2, Y-3, Rab-3), (A-6, B-4, C-4, X-2, Y-4, Rab-2), (A-6, B-4, C-4, X-2, Y-4, Rab-3), (A-6,1-4, C-5, X-1, Y-3, Rab-2), (A-6,1-4, C-5, X-1, Y-3, Rab-3), (A-6, B-4, C-5, X-1, Y-4, Rab-2), (A-6, B-4, C-5, X-1, Y-4, Rab-3), (A-6, B-4, C-5, X-2, Y-3, Rab-2), (A-6, B-4, C-5, X-2, Y-3, Rab-3), (A-6, B-4, C-5, X-2, Y-4, Rab-2), (A-6, B-4, C-5, X-2, Y-4, Rab-3), (A-6, B-6, C-4, X-1, Y-3, Rab-2), (A-6, B-6, C-4, X-1, Y-3, Rab-3), (A-6, B-6, C-4, X-1, Y-4, Rab-2), (A-6, B-6, C-4, X-1, Y-4, Rab-3), (A-6, B-6, C-4, X-2, Y-3, Rab-2), (A-6, B-6, C-4, X-2, Y-3, Rab-3), (A-6, B-6, C-4, X-2, Y-4, Rab-2), (A-6, B-6, C-4, X-2, Y-4, Rab-3), (A-6, B-6, C-5, X-1, Y-3, Rab-2), (A-6, B-6, C-5, X-1, Y-3, Rab-3), (A-6, B-6, C-5, X-1, Y-4, Rab-2), (A-6, B-6, C-5, X-1, Y-4, Rab-0.3), (A-6, B-6, C-5, X-2, Y-3, Rab-2), (A-6, B-6, C-5, X-2, Y-3, Rab-3), (A-6, B-6, C-5, X-2, Y-4, Rab-2), (A-6, B-6, C-5, X-2, Y-4, Rab-3).

More typically, the compounds described in WO98/04508 or the following compounds are preferred (Tables 1 to 3 show the structures of the moieties represented by the symbols A1, A2, ..., B1, B2, ..., C1, C2, ... employed in Table 4 or later. In the tables, cHex represents cyclohexyl, cPr represent cyclopropyl).

TABLE 1

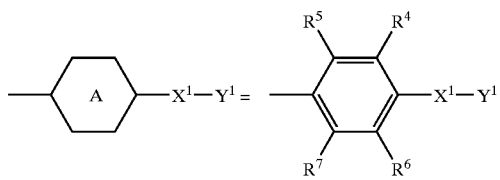

| | $R^4$ | $R^5$ | $R^6$ | $R^7$ | X | Y |
|---|---|---|---|---|---|---|
| A1 | H | H | H | H | O | $CH_2CH=CMe_2$ |
| A2 | F | H | H | H | O | $CH_2CH=CMe_2$ |
| A3 | H | F | H | H | O | $CH_2CH=CMe_2$ |
| A4 | H | H | H | H | NH | $CH_2CH=CMe_2$ |
| A5 | F | H | H | H | NH | $CH_2CH=CMe_2$ |
| A6 | H | F | H | H | NH | $CH_2CH=CMe_2$ |
| A7 | H | F | H | H | NH | H |
| A8 | H | F | H | H | NH | cHex |
| A9 | H | F | H | H | NH | $CH_2C_6H_5$ |
| A10 | H | Me | H | H | NH | $CH_2CH=CMe_2$ |
| A11 | H | H | H | H | NH | iPr |

TABLE 2

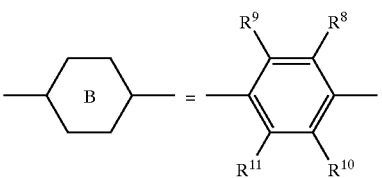

| | $R^8$ | $R^9$ | $R^{10}$ | $R^{11}$ |
|---|---|---|---|---|
| B1 | H | OMe | OMe | H |
| B2 | OH | OMe | OMe | H |
| B3 | OMs | OMe | OMe | H |
| B4 | H | Me | Me | H |
| B5 | OH | Me | Me | H |
| B6 | OMs | Me | Me | H |
| B7 | Me | Me | Me | Me |
| B8 | Me | Me | OMe | Me |
| B9 | Me | Me | OH | Me |
| B10 | Me | OMe | Me | Me |
| B11 | Me | OH | Me | Me |
| B12 | Me | OMe | OMe | Me |
| B13 | Me | Me | Me | Me |
| B14 | H | Me | Me | Me |
| B15 | F | Me | Me | H |
| B16 | H | Me | Me | F |
| B17 | H | Me | OMe | H |

TABLE 2-continued
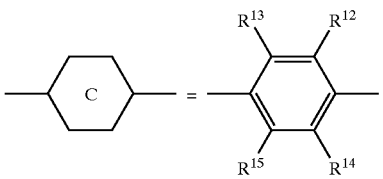
| | R⁸ | R⁹ | R¹⁰ | R¹¹ |
|---|---|---|---|---|
| B18 | H | OMe | Me | H |
| B19 | H | Cl | Cl | H |
| B20 | H | OEt | OEt | H |
| B21 | H | OiPr | OiPr | H |
| B22 | H | OcPr | OcPr | H |
| B23 | Me | COOMe | OMe | Me |
| B24 | Me | COOMe | Me | Me |
| B25 | H | SMe | SMe | H |
| B26 | H | SEt | SEt | H |
| B27 | Me | OMe | COOMe | Me |
| B28 | Me | Cl | Me | Me |
| B29 | H | Me | Me | OMe |
| B30 | Me | Me | COOMe | Me |
| B31 | Me | Me | Cl | Me |
| B32 | Me | Cl | H | Me |
| B33 | Cl | Me | Me | H |
| B34 | Cl | H | H | Me |
| B35 | H | Cl | Me | H |
| B36 | H | H | Me | Me |
| B37 | H | Me | H | Me |
| B38 | Me | H | Me | H |
| B39 | H | H | OMe | OMe |
| B40 | H | OMe | H | OMe |
| B41 | OMe | H | OMe | H |
| B42 | H | OMe | H | Me |
| B43 | Me | H | OMe | H |
| B44 | H | OMe | OMe | OMOM |
| B45 | H | OMe | OMe | OH |
| B46 | H | Me | Me | COOMe |
TABLE 3
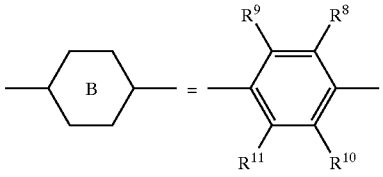

TABLE 4

| | A | B | C | —X²—Y² |
|---|---|---|---|---|
| I-1 | A1 | B4 | C1 | OCH$_2$CH=CMe$_2$ |
| I-2 | A2 | B4 | C1 | NHCH$_2$CH=CMe$_2$ |
| I-3 | A3 | B4 | C1 | OCH$_2$C$_6$H$_5$ |
| I-4 | A4 | B4 | C1 | NHCH$_2$CH=CMe$_2$ |
| I-5 | A5 | B4 | C1 | OCH$_2$CH=CMe$_2$ |
| I-6 | A6 | B4 | C1 | OCH$_2$CH=CMe$_2$ |
| I-7 | A7 | B4 | C1 | NHCH$_2$CH=CMe$_2$ |
| I-8 | A8 | B4 | C1 | OCH$_2$CH=CMe$_2$ |
| I-9 | A9 | B4 | C1 | NHiPr |
| I-10 | A6 | B1 | C1 | OCH$_2$CH=CMe$_2$ |
| I-11 | A6 | B2 | C1 | NHCH$_2$CH=CMe$_2$ |
| I-12 | A6 | B3 | C1 | OCH$_2$CF$_3$ |
| I-13 | A6 | B4 | C1 | NHCH$_2$CH=CMe$_2$ |
| I-14 | A6 | B5 | C1 | OCH$_2$CH=CMe$_2$ |
| I-15 | A6 | B6 | C1 | NHCH$_2$CH=CMe$_2$ |
| I-16 | A6 | B7 | C1 | OCH$_2$C$_6$H$_5$ |
| I-17 | A6 | B8 | C1 | NHCH$_2$CH=CMe$_2$ |
| I-18 | A6 | B9 | C1 | OCH$_2$CH=CMe$_2$ |
| I-19 | A6 | B10 | C1 | NHCH$_2$CH=CMe$_2$ |
| I-20 | A6 | B11 | C1 | OCH$_2$CH=CMe$_2$ |
| I-21 | A6 | B12 | C1 | NHCH$_2$CH=CMe$_2$ |
| I-22 | A6 | B13 | C1 | OCH$_2$CH=CMe$_2$ |
| I-23 | A6 | B14 | C1 | NHiPr |
| I-24 | A6 | B15 | C1 | OCH$_2$CH=CMe$_2$ |
| I-25 | A6 | B16 | C1 | NHCH$_2$CH=CMe$_2$ |
| I-26 | A6 | B17 | C1 | OCH$_2$CF$_3$ |
| I-27 | A6 | B18 | C1 | NHCH$_2$CH=CMe$_2$ |
| I-28 | A6 | B19 | C1 | OCH$_2$CH=CMe$_2$ |
| I-29 | A6 | B20 | C1 | NHCH$_2$CH=CMe$_2$ |
| I-30 | A6 | B21 | C1 | OCH$_2$CH=CMe$_2$ |
| I-31 | A6 | B22 | C1 | NHCH$_2$CH=CMe$_2$ |
| I-32 | A6 | B23 | C1 | OCH$_2$C$_6$H$_5$ |
| I-33 | A6 | B24 | C1 | NHCH$_2$CH=CMe$_2$ |

TABLE 5

| | A | B | C | —X²—Y² |
|---|---|---|---|---|
| I-34 | A6 | B25 | C1 | OCH$_2$CH=CMe$_2$ |
| I-35 | A6 | B26 | C1 | NHCH$_2$CH=CMe$_2$ |
| I-36 | A6 | B27 | C1 | OCH$_2$CH=CMe$_2$ |
| I-37 | A6 | B28 | C1 | NHCH$_2$CH=CMe$_2$ |
| I-38 | A6 | B29 | C1 | OCH$_2$CH=CMe$_2$ |
| I-39 | A6 | B30 | C1 | NHCH$_2$CH=CMe$_2$ |
| I-40 | A6 | B31 | C1 | OCH$_2$CH=CMe$_2$ |
| I-41 | A6 | B32 | C1 | NHCH$_2$CH=CMe$_2$ |
| I-42 | A6 | B33 | C1 | OCH$_2$CH=CMe$_2$ |
| I-43 | A6 | B34 | C1 | NHCH$_2$CH=CMe$_2$ |
| I-44 | A6 | B35 | C1 | OCH$_2$CH=CMe$_2$ |
| I-45 | A6 | B36 | C1 | NHCH$_2$CH=CMe$_2$ |
| I-46 | A6 | B37 | C1 | OCH$_2$CH=CMe$_2$ |
| I-47 | A6 | B38 | C1 | NHiPr |
| I-48 | A6 | B39 | C1 | OCH$_2$CH=CMe$_2$ |
| I-49 | A6 | B40 | C1 | NHCH$_2$CH=CMe$_2$ |
| I-50 | A6 | B41 | C1 | OCH$_2$CF$_3$ |
| I-51 | A6 | B42 | C1 | NHCH$_2$CH=CMe$_2$ |
| I-52 | A6 | B43 | C1 | OCH$_2$C$_6$H$_5$ |
| I-53 | A6 | B44 | C1 | NHCH$_2$CH=CMe$_2$ |

TABLE 5-continued

| | | | | $-X^2-Y^2$ |
|---|---|---|---|---|
| I-54 | A6 | B45 | C1 | OCH$_2$CH=CMe$_2$ |
| I-55 | A6 | B4 | C2 | OCH$_2$CH=CMe$_2$ |
| I-56 | A6 | B4 | C3 | NHCH$_2$CH=CMe$_2$ |
| I-57 | A6 | B4 | C4 | OCH$_2$CH=CMe$_2$ |
| I-58 | A6 | B4 | C5 | NHCH$_2$CH=CMe$_2$ |
| I-59 | A6 | B4 | C6 | OCH$_2$CH=CMe$_2$ |
| I-60 | A6 | B4 | C7 | NHCH$_2$CH=CMe$_2$ |
| I-61 | A6 | B4 | C8 | OCH$_2$CF$_3$ |
| I-62 | A6 | B4 | C9 | NHCH$_2$CH=CMe$_2$ |
| I-63 | A2 | B4 | C3 | OCH$_2$CH=CMe$_2$ |
| I-64 | A2 | B4 | C6 | NHCH$_2$CH=CMe$_2$ |
| I-65 | A4 | B4 | C3 | OCH$_2$CH=CMe$_2$ |
| I-66 | A4 | B4 | C6 | NHiPr |
| I-67 | A5 | B4 | C3 | OCH$_2$CH=CMe$_2$ |
| I-68 | A5 | B4 | C6 | NHCH$_2$CH=CMe$_2$ |

TABLE 6

| | | | | $-X^2-Y^2$ |
|---|---|---|---|---|
| I-69 | A2 | B7 | C1 | OCH$_2$CH=CMe$_2$ |
| I-70 | A2 | B7 | C3 | NHCH$_2$CH=CMe$_2$ |
| I-71 | A2 | B7 | C6 | OCH$_2$CH=CMe$_2$ |
| I-72 | A4 | B7 | C1 | NHCH$_2$CH=CMe$_2$ |
| I-73 | A4 | B7 | C3 | OCH$_2$CH=CMe$_2$ |
| I-74 | A4 | B7 | C6 | NHCH$_2$CH=CMe$_2$ |
| I-75 | A5 | B7 | C1 | OCH$_2$CH=CMe$_2$ |
| I-76 | A5 | B7 | C3 | NHCH$_2$CH=CMe$_2$ |
| I-77 | A5 | B7 | C6 | OCH$_2$CH=CMe$_2$ |
| I-78 | A2 | B8 | C1 | NHCH$_2$CH=CMe$_2$ |
| I-79 | A2 | B8 | C3 | OCH$_2$CH=CMe$_2$ |
| I-80 | A2 | B8 | C6 | NHCH$_2$CH=CMe$_2$ |
| I-81 | A4 | B8 | C1 | OCH$_2$CH=CMe$_2$ |
| I-82 | A4 | B8 | C3 | NHCH$_2$CH=CMe$_2$ |
| I-83 | A4 | B8 | C6 | OCH$_2$CH=CMe$_2$ |
| I-84 | A5 | B8 | C1 | NHCH$_2$CH=CMe$_2$ |
| I-85 | A5 | B8 | C3 | OCH$_2$CH=CMe$_2$ |
| I-86 | A5 | B8 | C6 | NHCH$_2$CH=CMe$_2$ |
| I-87 | A2 | B10 | C1 | OCH$_2$CH=CMe$_2$ |
| I-88 | A2 | B10 | C3 | NHCH$_2$CH=CMe$_2$ |
| I-89 | A2 | B10 | C6 | NHCH$_2$CH=CMe$_2$ |
| I-90 | A4 | B10 | C1 | OCH$_2$CF$_3$ |
| I-91 | A4 | B10 | C3 | OCH$_2$CF$_3$ |
| I-92 | A4 | B10 | C6 | NHCH$_2$CH=CMe$_2$ |
| I-93 | A5 | B10 | C1 | OCH$_2$CH=CMe$_2$ |
| I-94 | A5 | B10 | C3 | NHiPr |
| I-95 | A5 | B10 | C6 | OCH$_2$CH=CMe$_2$ |
| I-96 | A2 | B12 | C1 | NHCH$_2$CH=CMe$_2$ |
| I-97 | A2 | B12 | C3 | OCH$_2$CH=CMe$_2$ |
| I-98 | A2 | B12 | C6 | NHCH$_2$CH=CMe$_2$ |
| I-99 | A4 | B12 | C1 | OCH$_2$C$_6$H$_5$ |
| I-100 | A4 | B12 | C3 | NHCH$_2$CH=CMe$_2$ |
| I-101 | A4 | B12 | C6 | OCH$_2$CH=CMe$_2$ |
| I-102 | A5 | B12 | C1 | NHCH$_2$CH=CMe$_2$ |
| I-103 | A5 | B12 | C3 | OCH$_2$CH=CMe$_2$ |
| I-104 | A5 | B12 | C6 | NHCH$_2$CH=CMe$_2$ |

TABLE 7

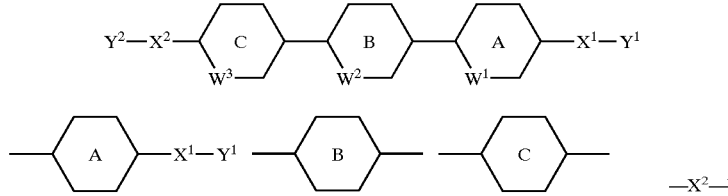

| | A | B | C | —X²—Y² |
|---|---|---|---|---|
| I-105 | A2 | B13 | C1 | OCH$_2$CF$_3$ |
| I-106 | A2 | B13 | C3 | NHCH$_2$CH=CMe$_2$ |
| I-107 | A2 | B13 | C6 | OCH$_2$C$_6$H$_5$ |
| I-108 | A4 | B13 | C1 | OCH$_2$CH=CMe$_2$ |
| I-109 | A4 | B13 | C3 | NHCH$_2$CH=CMe$_2$ |
| I-110 | A4 | B13 | C6 | OCH$_2$CH=CMe$_2$ |
| I-111 | A5 | B13 | C1 | NHCH$_2$CH=CMe$_2$ |
| I-112 | A5 | B13 | C3 | OCH$_2$CH=CMe$_2$ |
| I-113 | A5 | B13 | C6 | NHiPr |
| I-114 | A10 | B4 | C10 | NHCH$_2$CH=CMe$_2$ |
| I-115 | A10 | B7 | C10 | NHCH$_2$CH=CMe$_2$ |
| I-116 | A10 | B8 | C10 | NHCH$_2$CH=CMe$_2$ |
| I-117 | A10 | B10 | C10 | NHCH$_2$CH=CMe$_2$ |
| I-118 | A10 | B12 | C10 | NHCH$_2$CH=CMe$_2$ |
| I-119 | A10 | B13 | C10 | NHCH$_2$CH=CMe$_2$ |
| I-120 | A11 | B4 | C6 | NHiPr |
| I-121 | A11 | B7 | C6 | NHiPr |
| I-122 | A11 | B8 | C6 | NHiPr |
| I-123 | A11 | B10 | C6 | NHiPr |
| I-124 | A11 | B12 | C6 | NHiPr |
| I-125 | A11 | B13 | C6 | NHiPr |
| I-126 | A6 | B4 | C11 | NHCH$_2$CH=CMe$_2$ |
| I-127 | A6 | B7 | C11 | NHCH$_2$CH=CMe$_2$ |
| I-128 | A6 | B8 | C11 | NHCH$_2$CH=CMe$_2$ |
| I-129 | A6 | B10 | C11 | NHCH$_2$CH=CMe$_2$ |
| I-130 | A6 | B12 | C11 | NHCH$_2$CH=CMe$_2$ |
| I-131 | A6 | B13 | C11 | NHCH$_2$CH=CMe$_2$ |
| I-132 | A10 | B4 | C2 | OCH$_2$CH=CMe$_2$ |
| I-133 | A4 | B8 | C12 | OCH$_2$CHMe$_2$ |

TABLE 8

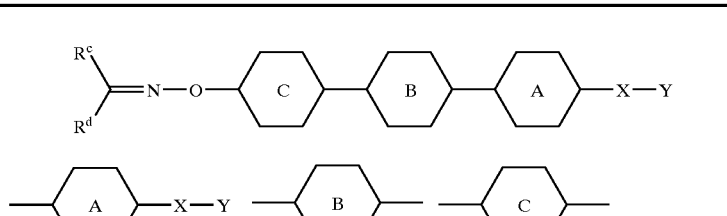

(Ic-1)

| | A | B | C | R$^c$ | R$^d$ |
|---|---|---|---|---|---|
| I-134 | A6 | B4 | C1 | Me | Me |
| I-135 | A6 | B4 | C1 | Et | Me |
| I-136 | A6 | B4 | C1 | Et | Et |
| I-137 | A6 | B4 | C1 | Et | H |
| I-138 | A6 | B4 | C1 | i-Pr | H |
| I-139 | A6 | B4 | C1 | CH=CMe$_2$ | H |
| I-140 | A6 | B4 | C1 | Me | OEt |
| I-141 | A6 | B4 | C1 | —(CH$_2$)$_4$— | |
| I-142 | A6 | B4 | C1 | —(CH$_2$)$_5$— | |
| I-143 | A6 | B4 | C1 | Ph | Me |
| I-144 | A6 | B4 | C1 | Ph | H |
| I-145 | A6 | B4 | C1 | 2-thienyl | H |
| I-146 | A6 | B4 | C1 | 2-thienyl | Me |
| I-147 | A6 | B4 | C2 | Me | Me |
| I-148 | A6 | B4 | C3 | Me | Me |
| I-149 | A6 | B4 | C4 | Me | Me |
| I-150 | A6 | B4 | C5 | Me | Me |
| I-151 | A6 | B4 | C6 | Me | Me |
| I-152 | A6 | B4 | C7 | Me | Me |
| I-153 | A6 | B4 | C8 | Me | Me |
| I-154 | A6 | B4 | C9 | Me | Me |
| I-155 | A6 | B7 | C1 | Me | Me |

TABLE 8-continued

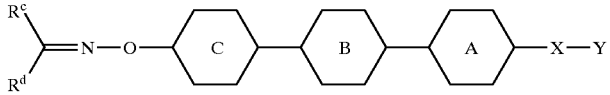

(Ic-1)

| | A | B | C | R^c | R^d |
|---|---|---|---|---|---|
| I-156 | A6 | B8 | C1 | Et | H |
| I-157 | A6 | B9 | C1 | i-Pr | H |
| I-158 | A6 | B10 | C1 | Me | OEt |
| I-159 | A6 | B11 | C1 | —(CH$_2$)$_4$— | |
| I-160 | A6 | B12 | C1 | —(CH$_2$)$_5$— | |
| I-161 | A6 | B14 | C1 | Ph | Me |
| I-162 | A6 | B30 | C1 | CH=CMe$_2$ | H |
| I-163 | A6 | B45 | C1 | 2-thienyl | H |
| I-164 | A6 | B46 | C1 | 2-furyl | Me |

TABLE 9

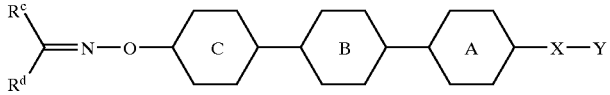

(Ic-1)

| | A | B | C | R^c | R^d |
|---|---|---|---|---|---|
| I-165 | A1 | B4 | C1 | —(CH$_2$)$_5$— | |
| I-166 | A2 | B4 | C1 | Ph | Me |
| I-167 | A3 | B4 | C1 | Et | H |
| I-168 | A4 | B4 | C1 | CH=CMe$_2$ | H |
| I-169 | A5 | B4 | C1 | —(CH$_2$)$_4$— | |
| I-170 | A7 | B4 | C1 | Me | Me |
| I-171 | A8 | B4 | C1 | Me | Me |
| I-172 | A9 | B4 | C1 | 2-thienyl | H |
| I-173 | A9 | B4 | C1 | Me | Me |
| I-174 | A4 | B7 | C1 | Me | Me |
| I-175 | A4 | B7 | C1 | Ph | Me |
| I-176 | A4 | B7 | C1 | Me | OEt |
| I-177 | A4 | B7 | C7 | iPr | H |
| I-178 | A4 | B7 | C7 | Et | Et |
| I-179 | A4 | B7 | C7 | Me | Me |
| I-180 | A4 | B7 | C9 | Me | Me |
| I-181 | A4 | B4 | C1 | i-Pr | H |
| I-182 | A4 | B8 | C1 | Me | Me |
| I-183 | A4 | B12 | C1 | Me | Me |
| I-184 | A4 | B30 | C1 | Me | Me |
| I-185 | A4 | B44 | C1 | Me | Me |
| I-186 | A4 | B45 | C1 | Me | Me |
| I-187 | A4 | B30 | C7 | Me | Me |
| I-188 | A2 | B7 | C1 | Me | Me |

TABLE 10

(Ic-2)

Structure: R^c R^d C=N-O-CH2-[C]-[B]-[A]-X-Y

-[A]-X-Y   -[B]-   -[C]-

| | A | B | C | R^c | R^d |
|---|---|---|---|---|---|
| I-189 | A4 | B7 | C6 | Me | Me |
| I-190 | A4 | B8 | C6 | Me | Me |
| I-191 | A4 | B9 | C6 | Me | Me |
| I-192 | A4 | B11 | C6 | Me | Me |
| I-193 | A4 | B45 | C6 | Me | Me |
| I-194 | A4 | B46 | C6 | 2-thienyl | H |
| I-195 | A4 | B4 | C1 | Me | Me |
| I-196 | A6 | B4 | C1 | Me | Me |
| I-197 | A6 | B4 | C1 | i-Pr | H |
| I-198 | A6 | B4 | C1 | Me | OEt |
| I-199 | A6 | B4 | C1 | —(CH$_2$)$_4$— | |
| I-200 | A6 | B4 | C1 | Ph | Me |
| I-201 | A6 | B4 | C1 | 2-thienyl | Me |
| I-202 | A6 | B4 | C2 | Me | Me |
| I-203 | A6 | B4 | C3 | i-Pr | H |
| I-204 | A6 | B4 | C4 | Et | OMe |
| I-205 | A6 | B4 | C5 | Et | Me |
| I-206 | A6 | B4 | C6 | Ph | Me |
| I-207 | A6 | B4 | C7 | —(CH$_2$)$_5$— | |
| I-208 | A6 | B4 | C8 | CH=CMe$_2$ | H |
| I-209 | A6 | B4 | C9 | 2-furyl | H |
| I-210 | A6 | B7 | C1 | Me | Me |
| I-211 | A6 | B8 | C1 | Et | H |
| I-212 | A6 | B9 | C1 | i-Pr | H |
| I-213 | A6 | B10 | C1 | Me | OEt |
| I-214 | A6 | B11 | C1 | —(CH$_2$)$_4$— | |
| I-215 | A6 | B12 | C1 | —(CH$_2$)$_5$— | |
| I-216 | A6 | B14 | C1 | Ph | Me |
| I-217 | A6 | B30 | C1 | Ph | H |
| I-218 | A6 | B45 | C1 | 2-thienyl | H |
| I-219 | A6 | B46 | C1 | 2-furyl | Me |
| I-220 | A1 | B4 | C1 | —(CH$_2$)$_5$— | |
| I-221 | A2 | B4 | C1 | Ph | Me |
| I-222 | A3 | B4 | C1 | Et | H |
| I-223 | A4 | B4 | C1 | i-Pr | H |
| I-224 | A5 | B4 | C1 | —(CH$_2$)$_4$— | |
| I-225 | A7 | B4 | C1 | Me | Me |
| I-226 | A8 | B4 | C1 | CH=CMe$_2$ | H |
| I-227 | A9 | B4 | C1 | 2-thienyl | H |

TABLE 11

(Ic-3)

Structure: R^c R^d C=N-NH-[C]-[B]-[A]-X-Y

-[A]-X-Y   -[B]-   -[C]-

| | A | B | C | R^c | R^d |
|---|---|---|---|---|---|
| I-228 | A6 | B4 | C1 | Et | Me |
| I-229 | A6 | B4 | C1 | Et | Et |
| I-230 | A6 | B4 | C1 | Et | H |
| I-231 | A6 | B4 | C1 | Pr | H |
| I-232 | A6 | B4 | C1 | Me | OEt |
| I-233 | A6 | B4 | C1 | —(CH$_2$)$_4$— | |
| I-234 | A6 | B4 | C1 | —(CH$_2$)$_5$— | |
| I-235 | A6 | B4 | C1 | Me | Me |
| I-236 | A6 | B4 | C1 | Ph | Me |

TABLE 11-continued (Ic-3)

Structure: R^c R^d C=N-NH-[C]-[B]-[A]-X-Y

Ring definitions:
- -[A]-X-Y
- -[B]-
- -[C]-

| | A | B | C | R^c | R^d |
|---|---|---|---|---|---|
| I-237 | A6 | B4 | C1 | Ph | H |
| I-238 | A6 | B4 | C1 | 2-furyl | H |
| I-239 | A6 | B4 | C1 | i-Pr | H |
| I-240 | A6 | B4 | C1 | CH=CMe₂ | H |
| I-241 | A6 | B4 | C1 | 2-thienyl | Me |
| I-242 | A6 | B4 | C2 | Me | Me |
| I-243 | A6 | B4 | C3 | Et | Me |
| I-244 | A6 | B4 | C4 | Pr | H |
| I-245 | A6 | B4 | C5 | Me | OEt |
| I-246 | A6 | B4 | C6 | Ph | Me |
| I-247 | A6 | B4 | C7 | Ph | H |
| I-248 | A6 | B4 | C8 | 2-thienyl | Me |
| I-249 | A6 | B4 | C9 | —(CH₂)₄— | |
| I-250 | A6 | B7 | C1 | Me | Me |
| I-251 | A6 | B8 | C1 | Et | H |
| I-252 | A6 | B9 | C1 | i-Pr | H |
| I-253 | A6 | B10 | C1 | Me | OEt |
| I-254 | A6 | B11 | C1 | CH=CMe₂ | H |
| I-255 | A6 | B12 | C1 | —(CH₂)₅— | |
| I-256 | A6 | B14 | C1 | Ph | Me |
| I-257 | A6 | B30 | C1 | Ph | H |
| I-258 | A6 | B45 | C1 | 2-thienyl | H |
| I-259 | A6 | B46 | C1 | 2-furyl | Me |
| I-260 | A1 | B4 | C1 | —(CH₂)₅— | |
| I-261 | A2 | B4 | C1 | Ph | Me |
| I-262 | A3 | B4 | C1 | Et | H |
| I-263 | A4 | B4 | C1 | i-Pr | H |
| I-264 | A5 | B4 | C1 | —(CH₂)₄— | |
| I-265 | A7 | B4 | C1 | Me | H |
| I-266 | A8 | B4 | C1 | CH=CMe₂ | H |
| I-267 | A9 | B4 | C1 | 2-thienyl | Me |

TABLE 12

(Ic-4)

Structure: R^a R^b N-NH-[C]-[B]-[A]-X-Y

Ring definitions:
- -[A]-X-Y
- -[B]-
- -[C]-

| | A | B | C | R^a | R^b |
|---|---|---|---|---|---|
| I-268 | A6 | B4 | C1 | Et | H |
| I-269 | A6 | B4 | C1 | Pr | H |
| I-270 | A6 | B4 | C1 | i-Pr | H |
| I-271 | A6 | B4 | C1 | i-Bu | H |
| I-272 | A6 | B4 | C1 | Et | Me |
| I-273 | A6 | B4 | C1 | Et | Et |
| I-274 | A6 | B4 | C1 | —(CH₂)₄— | |
| I-275 | A6 | B4 | C1 | H | H |
| I-276 | A6 | B4 | C1 | —CH₂CH(Me)(CH₂)₃— | |
| I-277 | A6 | B4 | C1 | Ph | Me |
| I-278 | A6 | B4 | C1 | COMe | H |
| I-279 | A6 | B4 | C1 | 2-thienyl | H |
| I-280 | A6 | B4 | C1 | CH₂CH=CMe₂ | H |
| I-281 | A6 | B4 | C1 | Me | Me |
| I-282 | A6 | B4 | C1 | 2-thienyl | Me |
| I-283 | A6 | B4 | C1 | COOtBu | H |
| I-284 | A6 | B4 | C2 | Me | Me |
| I-285 | A6 | B4 | C3 | i-Bu | Me |
| I-286 | A6 | B4 | C4 | Pr | H |

TABLE 12-continued

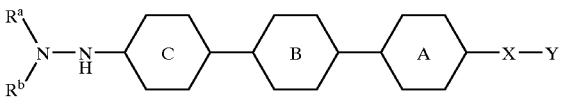

(Ic-4)

| | | | | $R^a$ | $R^b$ |
|---|---|---|---|---|---|
| I-287 | A6 | B4 | C5 | —(CH$_2$)$_4$— | |
| I-288 | A6 | B4 | C6 | Ph | Me |
| I-289 | A6 | B4 | C7 | Ph | H |
| I-290 | A6 | B4 | C8 | CH$_2$CH=CMe$_2$ | H |
| I-291 | A6 | B4 | C9 | COOEt | H |
| I-292 | A6 | B7 | C1 | Me | Me |
| I-293 | A6 | B8 | C1 | Et | H |
| I-294 | A6 | B9 | C1 | i-Pr | H |
| I-295 | A6 | B10 | C1 | COMe | H |
| I-296 | A6 | B11 | C1 | —(CH$_2$)$_2$CH(OMe)CH$_2$— | |
| I-297 | A6 | B12 | C1 | —(CH$_2$)$_5$— | |
| I-298 | A6 | B14 | C1 | Ph | Me |
| I-299 | A6 | B30 | C1 | H | H |
| I-300 | A6 | B45 | C1 | COOEt | H |
| I-301 | A6 | B46 | C1 | 2-furyl | Me |
| I-302 | A1 | B4 | C1 | —(CH$_2$)$_2$CH(NH$_2$)(CH$_2$)$_2$— | |
| I-303 | A2 | B4 | C1 | Ph | Me |
| I-304 | A3 | B4 | C1 | COOtBu | H |
| I-305 | A4 | B4 | C1 | i-Bu | H |
| I-306 | A5 | B4 | C1 | —(CH$_2$)$_4$— | |
| I-307 | A7 | B4 | C1 | COiPr | H |
| I-308 | A8 | B4 | C1 | Me | Me |
| I-309 | A9 | B4 | C1 | CH$_2$CH=CMe$_2$ | H |

A method for producing Compound (I) is described below.

Method for Producing Compound (I')

A compound represented by Formula (I') shown below (hereinafter referred to as Compound (I')) can be produced by reacting a compound represented by Formula (IIa) (hereinafter referred to as Compound (IIa)) with a bicyclic compound represented by Formula (IIIa) (hereinafter referred to as Compound (IIIa)), or reacting a compound represented by Formula (IIb) (hereinafter referred to as Compound (IIb)) with a bicyclic compound represented by Formula (IIIb) (hereinafter referred to as Compound (IIIb)):

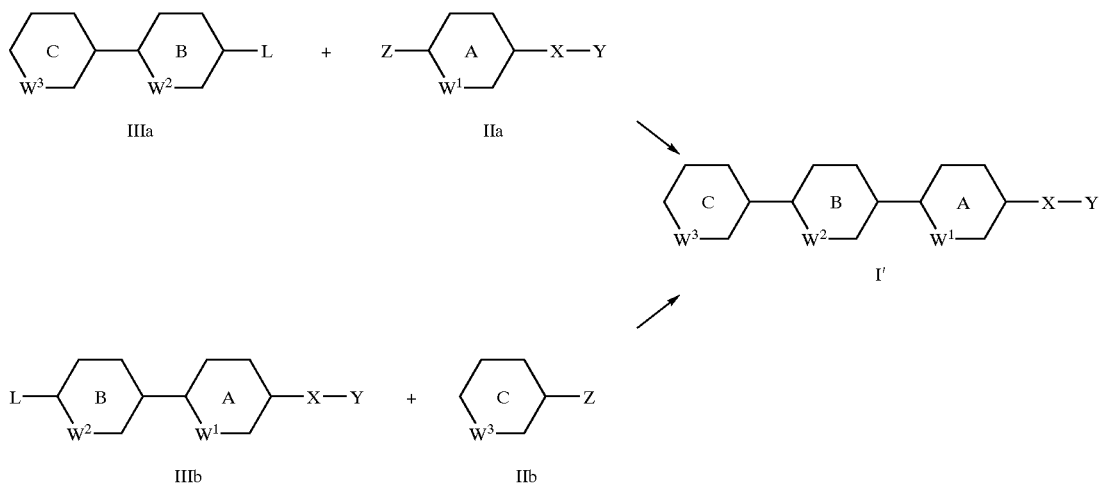

wherein one of L and Z is dihydroxyboryl, di-lower alkylboryl or di-lower alkoxyboryl, and the other is halogen or —OSO2 (C$_q$F$_{2q+1}$) (q is an integer of 0 to 4), and other symbols are defined as described above).

Compound (IIa) and Compound (IIIa) or Compound (IIb) and Compound (IIIb) are reacted in a mixture of a suitable solvent (for example, benzene, toluene, N,N-dimethylformamide, dimethoxyethane, tetrahycrofuran, dioxane, ethanol or methanol) with water or in an anhydrous system in the presence of a palladium catalyst (for example Pd(PPh$_3$)$_4$, PdCl$_2$(PPh$_3$)$_2$, PdCl$_2$, Pd(OAC)$_2$ or PdCl$_2$(CH$_3$CN)$_2$, preferably Pd(PPh$_3$)$_4$) in a basic condition (with a base such as K$_3$PO$_4$, NaOEt, NaHCO$_3$, Na$_2$CO$_3$, Et$_3$N, Ba(OH)$_2$, CS$_2$CO$_3$, CsF, NaOH or Ag$_2$CO$_3$) at room temperature or with heating for several ten minutes to several ten hours to give Compound (I').

One of substituents L and Z in compounds to be reacted with each other is any boryl group capable of being used in Suzuki reaction (Chemical Communication 1979, 866, Journal of Organic Synthesis Society, 1993, Vol. 51, NO. 11, page 91 to 100), and preferably dihydroxyboryl. The other is any leaving group applicable to Suzuki reaction, such as halogen or —OSO$_2$(C$_q$F$_{2q+1}$) wherein q is an integer of 0 to 4. Those preferred especially are halogen and trifluoromethanesulfonyloxy (hereinafter abbreviated as OTf), with bromine, iodine and OTf being most preferred.

Other substituents on ring A, ring B and ring C in Compounds (IIa), (IIa), (IIb) and (IIb) and —X—Y are any groups by which Suzuki reaction is not affected adversely, including those except for halogen and —OSO$_2$(C$_q$F$_{2q+1}$) wherein q is an integer of 0 to 4.

For example, Y may be optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or an optionally substituted 5- or 6-membered heterocyclic ring which may be fused with a benzene ring, and when X is —CH$_2$—, Y may also be optionally substituted lower alkoxy. When X is —O— or —NR$^1$—then Y may also be optionally substituted lower alkoxycarbonyl, optionally substituted lower alkylsulfonyl or optionally substituted arylsulfonyl.

Even when any of the substituents on rings A, B and C is halogen, the reaction described above can satisfactorily be advanced when the reactivity between substituents L and Z is higher relatively.

Also even when any of the substituents on rings A, B and C or —X—Y is hydroxy, the reaction described above can be effected. The reaction is preferably effected after introducing an ordinarily employed hydroxy protective group (for example, methoxymethyl, benzyl, t-butyldimethylsilyl, methanesulfonyl or p-toluenesulfonyl) which is subjected subsequently to a deprotection.

While Compound (I') is synthesized most efficiently and conveniently by employing Suzuki reaction described above, silicon, zinc or tin may also be employed instead of boryl group in the scheme shown above.

For example, when one of L and Z is —SiR$^e$$_{(3-r)}$(Hal)$_r$ (wherein each R$_e$ may be different and is lower alkyl, Hal is halogen, r is an integer of 1 to 3) and the other is halogen or —OSO$_2$(C$_q$F$_{2q+1}$) wherein q is an integer of 0 to 4, an ordinarily employed palladium catalyst is employed in a coupling reaction (Synlett, (1991) 845–853, J. Org. Chem., 1996, 61, 7232–7233). A preferred palladium catalyst may for example be (i-Pr$_3$P)$_2$PdCl$_2$, [(dcpe)PdCl$_2$](cdpe=1,2-bis (dicyclohexylphosphino)ethane), (η$^3$-C$_3$H$_5$PdCl)$_2$ and the like.

Also when one of L and Z is —SnR$^f$$_3$ (wherein each R$^f$ may be different and is lower alkyl) and the other is halogen, acetyloxy or —OSO$_2$(C$_q$F$_{2q+1}$) wherein q is an integer of 0 to 4, an ordinarily employed palladium catalyst (preferably Pd(PPh$_3$)$_4$ and the like) can be employed to obtain an intended compound (Angew. Chem. Int. Ed. Engl., 25 (1986) 508–524).

Also by reacting a compound in which one of L and Z is —Zn(Hal) wherein Hal is halogen and the other is halogen, an intended compound can be synthesized (Acc. Chem. Res. 1982, 15, 340–348). While any ordinarily employed palladium catalyst can be employed, those exemplified preferably are Pd(PPh$_3$)$_4$, PdCl$_2$(dppf)(dppf=1,1'-bis(diphenylphosphino)ferrocene), PdCl$_2$(PPh$_3$, PdCl$_2$ (P(o-Tolyl)$_3$)$_2$ and Pd(OAc)$_2$.

Any of these reactions may be conducted in a suitable solvent (for example, N, N-dimethylformamide, tetrahydrofuran) at room temperature or with heating for several ten minutes to several ten hours.

Compounds (IIIa) and (IIIb) in a scheme shown above may be those known per se, or may be derived from a compound represented by Formula (Va) (hereinafter referred to as Compound (Va)) or a compound represented by Formula (Vb) (hereinafter referred to as Compound (Vb)) which can be synthesized by a known method or a method described below:

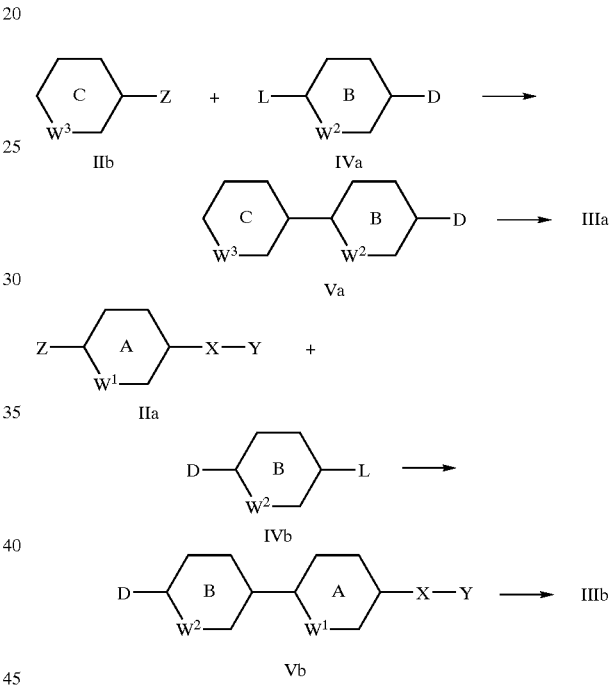

wherein D and L are groups by which Suzuki reaction of Z is not affected adversely, and when a compound represented by Formula (IVa) or (IVb) is a symmetric compound, they may be groups similar to L, and other symbols are defined as described above.

First, a step similar to that described above is employed to react Compound (IIb) with Compound (IVa) or Compound (IIa) with Compound (IVb) to give Compound (Va) or (Vb). When Compound IVa) or IVb) is not a symmetric compound, D is preferably a group which has no particular adverse effect on Suzuki reaction of L and Z and which can conveniently be converted into L. For example, hydroxy, hydrogen, formyl and nitro may be employed. L or Z may be subjected to a reaction employing silicon, zinc or tin instead of a boryl group described above.

Subsequently, D is converted into a substituent L which is applicable to Suzuki reaction.

For example when D is hydroxy, a reaction with a trifluoromethanesulfonylating agent (for example, trifluoromethanesulfonic anhydride, trifluoromethanesulfonyl chloride or N-phenyltrifluoromethanesulfonimide) is conducted in a suitable solvent (for example, dichloromethane, chloroform, tetrahydrofuran, benzene or toluene) in the presence of a base (sodium hydride, pyridine, triethylamine or potassium carbonate) at −20° C. or with heating for several minutes to several ten hours to give an intended compound in which L is OTf.

When D is hydrogen, a reaction with a halogenating agent (for example, chlorine, bromine, iodine or N-bromosuccinimide) is conducted in a suitable solvent (for example, acetic acid, dichloromethane, chloroform, carbon tetrachloride, N,N-dimethylformamide or water) at −20° C. or with heating for several minutes to several ten hours to give an intended compound in which L is halogen.

When D is formyl, it is subjected to Baeyer-Villiger oxidation by a standard method to form formyloxy which is then hydrolyzed to form hydroxy. Thereafter, a procedure similar to that described above is employed to give a compound in which L is OTf.

When D is nitro, it is reduced to amino and subjected to Sandmeyer reaction to give a compound in which L is halogen.

Method for Producing Compound (I″)

A compound represented by Formula (I″) shown below (hereinafter referred to as Compound (I″)) can be produced by Suzuki reaction between a compound represented by Formula (VI) (hereinafter referred to as Compound (VI)) and a compound represented by Formula (Ia) (hereinafter referred to as Compound (Ia)), or by a condensation between a compound represented by Formula (VII) (hereinafter referred to as Compound (VII)) and a compound represented by Formula (VIII) (hereinafter referred to as Compound (VIII)):

In the reaction of Compound (VII) and Compound (VIII), when $V^2$ in an intended compound is —O—, —NH—, —OCH$_2$—, —CH$_2$O— or —NHCH$_2$—, one of substituents M and Q is hydroxy or amino and the other is a leaving group such as halogen, lower alkylsulfonyloxy, arylsulfonyloxy, lower alkylsulfonyl or arylsulfonyl or methyl having such leaving group as a substituent. These two compounds are reacted in a suitable solvent (for example, benzene, toluene, acetone, acetonitrile, N,N-dimethylformamide, dimethylsulfoxide, pyridine, methanol or ethanol) in the presence of a base (for example, sodium hydride, pyridine, triethylamine, potassium carbonate, sodium hydroxide or potassium hydroxide) optionally with a copper catalyst (copper powder, CuCl or CuO) at 0° C. or with heating for several minutes to several tens hours to give an intended compound.

In the reaction of Compound (VII) and Compound (VIII), when $V^2$ in an intended compound is —CO— or —CH(OH)—, one of substituents M and Q is lithium or an organic metal such as Mg(Hal) wherein Hal is halogen and the other is carboxy, lower alkoxycarbonyl, carbamoyl or formyl. These two compounds are reacted in a suitable solvent (for example, diethylether, tetrahydrofuran, dimethoxyethane or dioxane) at −78° C. or with heating for several minutes to several hours to give an intended compound.

When $V^2$ in an intended compound is —CH(OR$^g$)— wherein R$^g$ is lower alkyl, a compound in which $V^2$ is —CH(OH)— is obtained and subsequently alkylated.

An intended compound in which $V^2$ is —CO— can be obtained by reacting a compound in which $V^2$ is —CH(OH)— with an oxidizing agent such as chromic anhydride

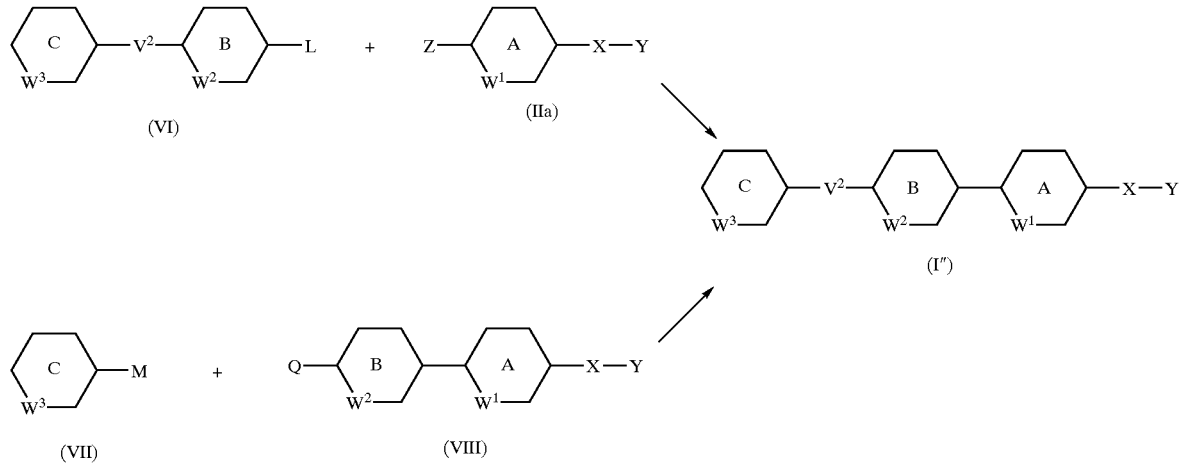

wherein one of M and Q is hydroxy or amino and the other is halogen, lower alkylsulfonyloxy, arylsulfonyloxy lower alkylsulfonyl or arylsulfonyl as itself or as a substituent on methyl, or, one is lithium or Mg(Hal) wherein Hal is halogen and the other is carboxy, lower alkoxycarbonyl, carbamoyl or formyl, or one is formyl and the other is halogenated methyl, or one is ethynyl and the other is halogen, and other symbols are defined as described above.

The conditions under which Compound (VI) and Compound (IIa) are reacted are similar to those in a method for producing Compound (I′).

or Jones reagent in a solvent suitable for the oxidizing agent such as t-butyl alcohol or acetone at 0° C. or with heating for several hours. An intended compound in which $V^2$ is —CH(OH)— can be obtained by reducing a compound in which $V^2$ is —CO— in a suitable solvent (for example diethylether, tetrahydrofuran, dimethoxyethane, dioxane, methanol and ethanol) with sodium borohydride, lithium aluminum hydride and the like.

When $V^2$ in an intended compound is —CH═CH—, one of substituents M and Q is formyl and the other is a halogenated methyl (halogen may for example be chlorine, bromine or iodine). In this case, an intended compound can be obtained by Wittig reaction (Organic Reaction, 1965, Vol. 14, page 270).

When $V^2$ in an intended compound is —CH═CH—, one of substituents M and Q is ethynyl and the other is halogen (preferably bromine or iodine), and the synthesis can be effected by a coupling reaction (for example, Synthesis (1980) 627, Tetrahedron, 1982, 38, 631) using an ordinarily employed palladium catalyst.

Other substituents on ring A, ring B and ring C in Compounds (VI), (IIa), (VII) and (VIII) and —X—Y are any groups by which Suzuki reaction of L and Z or the condensation between M and Q is not affected adversely Even when any of the substituents in the reaction of Compound (VI) and (Ia) is halogen, the reaction described above can satisfactorily be advanced when the reactivity between substituents L and Z is higher relatively. While the reaction described above is possible even when any of the substituents is hydroxy, it is preferable in such case that the reaction is effected after introducing a protective group which is subjected subsequently to an ordinary deprotection.

Compound (VI) in the reaction scheme described above may be a known compound or may be synthesized from a compound represented by Formula (X) (hereinafter refereed to as Compound (X)) which is synthesized by a method described below:

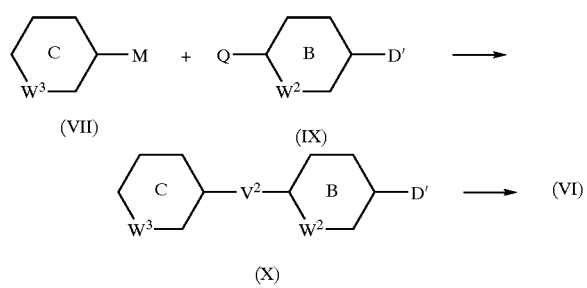

wherein D' is a group by which the condensation between M and Q is not affected adversely, and, when a compound represented by Formula (IX) is a symmetric compound, it may be a group identical to Q, and other symbols are defined as described above.

When Compound (IX) is not a symmetric compound, D' is preferably a group which has no particular adverse effect on the condensation between M and Q and which can conveniently be converted into L. For example, hydrogen, formyl or protected hydroxy or nitro is employed. A protective group for hydroxy may for example be benzyl, t-butyldimethylsilyl and methoxymethyl. A method for converting D' into L is similar to that for converting D into L described above. Other conditions are similar to those in the reaction of Compound (VII) and Compound (VIII).

Compound (VIII) may be a known compound or may be derived by a known method or a compound synthesized from Compound (Vb) described above by a standard method.

A compound represented by Formula (I'''):

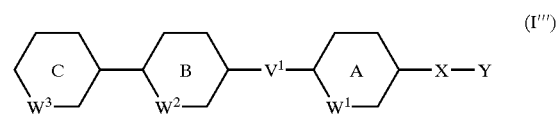

wherein each symbol is defined as described above may also be synthesized similarly to Compound (I'').

With regard to Compound (Ic), the following methods may be exemplified for obtaining intended compounds.

(Method A)

For example, a compound represented by Formula (Ic') (hereinafter referred to as Compound (Ic')) wherein each of $R^a$ and $R^b$ is independently hydrogen, optionally substituted lower alkyl, optionally substituted lower alkenyl, optionally substituted aryl, optionally substituted cycloalkyl, optionally substituted acyl or optionally substituted lower alkoxycarbonyl, or they are taken together to form —(CR$^e$R$^f$)r- can be obtained from a compound represented by Formula (XI) (hereinafter referred to as Compound XI)) and a compound represented by Formula (XII) (hereinafter referred to as Compound (XII)):

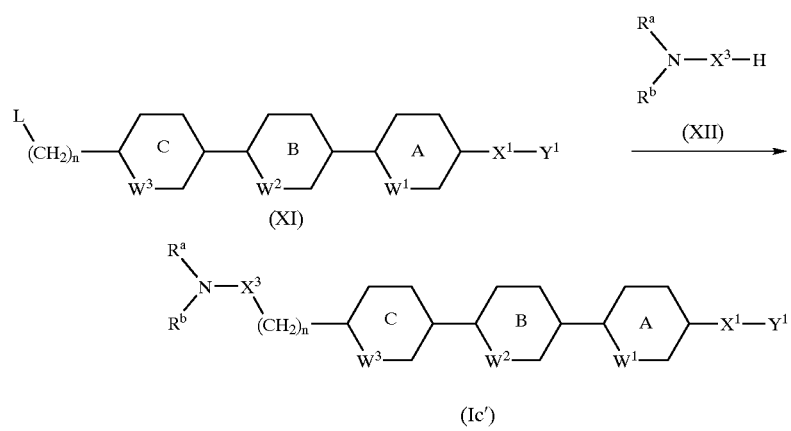

wherein substituent L is a leaving group such as halogen, lower alkylsulfonyl, arylsulfonyl, lower alkylsulfonyloxy or arylsulfonyloxy, and other symbols are defined as described above.

Compounds (X) and (XII) are reacted in a suitable solvent (for example, benzene, toluene, acetone, acetonitrile, tetrahydrofuran, N,N-dimethylformamide, dimethylsulfoxide, pyridine, methanol or ethanol) optionally in the presence of a base (for example, sodium hydride, potassium t-butoxide, pyridine, triethylamine, potassium carbonate, sodium hydroxide or potassium hydroxide) at 0° C. or with heating for several minutes to several tens hours to give intended Compound (Ic').

Compound (Ic'') wherein $R^a$ and $R^b$ are taken together to form $R^c R^d C$= is produced from $R^c R^d C$=N—$X^3$ and Compound (XI) as described above or from Compound (Ic') wherein $R^a$ and $R^b$ are hydrogens obtained from Compound (XI) and a compound represented by Formula (XIII) (hereinafter referred to as Compound (XIII)):

Compound (Ic') wherein $R^a$ and $R^b$ are hydrogens can also be synthesized from a compound represented by Formula (XI') (hereinafter referred to as Compound (XI')):

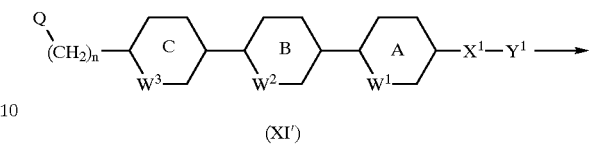

(XI')

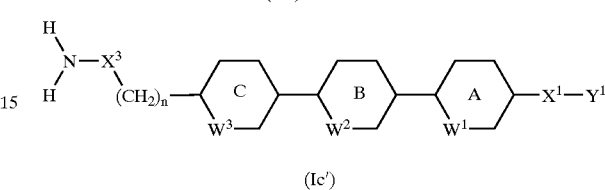

(Ic')

(XI) →

[reaction scheme showing Compound (Ic') and (Ic'') with (XIII)]

wherein each symbol is defined as described above.

First, Compound (XI) is reacted with hydrazine in a suitable solvent (for example, toluene, tetrahydrofuran, N,N-dimethylformamide, dimethylsulfoxide, pyridine, methanol or ethanol) or without using any solvent to give Compound (Ic', $X^3$=NH) or subjected to a method employing N-hydroxyphthalimide as described in Journal of Chemical Society, 1926, 2348 or a method employing benzohydroxamic acid as described in Journal of Chemical Society, 1927, 874 to give Compound (Ic', $X^3$=O). A compound thus obtained is subjected to a dehydration condensation with a carbonyl compound (XIII) such as ketone or aldehyde optionally in the presence of an acid catalyst (hydrochloric acid, acetic acid, trifluoroacetic acid, lower alkanesulfonic acid, arylsulfonic acid and the like) to give intended Compound (Ic'').

When one of $R^c$ and $R^d$ in Compound (Ic'') is lower alkoxy, a reaction with a carbonyl compound ($R^c C$(=O)$R^d$) in a suitable solvent (for example, toluene, tetrahydrofuran, dioxane or dichloromethane) in the presence of an acid (hydrochloric acid, acetic acid, perchloric acid and the like) is effected, whereby converting into an intended compound having other $R^c$ and $R^d$.

wherein Q is $NH_2$ or a group by which Suzuki reaction is not affected adversely and which can be converted into substituent L by a general method, and other symbols are defined as described above.

For example, Compound (XI', Q=OH) is converted into an alkoxide or phenoxide using a suitable base (for example, sodium hydride, potassium t-butoxide, potassium carbonate, sodium hydroxide and potassium hydroxide) and then reacted with chloramine or O-arylsulfonylhydroxylamine (Journal of Organic Chemistry, 1973 (38) 1239–1241) or Compound (XI', Q=$NH_2$) is reacted with chloramine or hydroxylamine-O-sulfonic acid (Journal of Organic Chemistry, 1949 (14) 813).

(Method B)

Compound (Ic') can be produced also by reacting a compound represented by Formula (XIV) (hereinafter referred to as Compound (XIV)) with a compound represented by Formula (XV) (hereinafter referred to as Compound (XV)):

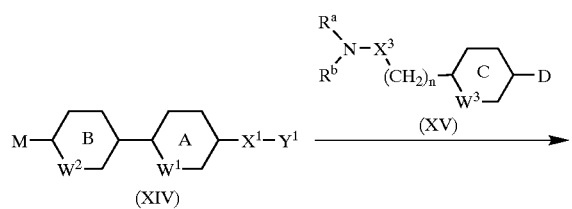

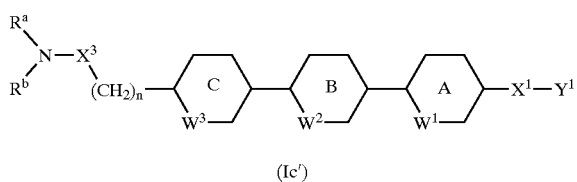

wherein one of M and D is dihydroxyboryl, di-lower alkylboryl or di-lower alkoxyboryl and the other is halogen or —OSO$_2$(C$_q$F$_{2q+1}$) wherein q is an integer of 0 to 4, and other symbols are defined as described above.

Compound (XIV) and Compound (XV) are reacted in a mixture of a suitable solvent (for example, benzene, toluene, N,N-dimethylformamide, dimethoxyethane, tetrahydrofuran, dioxane, ethanol or methanol) with water or in an anhydrous system in the presence of a palladium catalyst (for example Pd(PPh$_3$)$_4$, PdCl$_2$(PPh$_3$)$_2$, PdCl$_2$, Pd(OAc)$_2$ or PdCl$_2$(CH$_3$CN)$_2$, preferably Pd(PPh$_3$)$_4$) in a basic condition (with a base such as K$_3$PO$_4$, NaHCO$_3$, NaOEt, Na$_2$CO$_3$, Et$_3$N, Ba(OH)$_2$, Cs$_2$CO$_3$, CsF, NaOH or Ag$_2$CO$_3$) at room temperature or with heating for several tens minutes to several tens hours to give Compound (Ic').

Compound (XV) may be a known compound or may be obtained by a method for Compounds (Ic') and (IC") described above.

One of substituent M and substituent D is any boryl group capable of being used in Suzuki reaction, and preferably dihydroxyboryl. The other is any leaving group applicable to Suzuki reaction, such as halogen or —OSO$_2$(C$_q$F$_{2q+1}$) wherein q is an integer of 0 to 4. Those preferred especially are halogen and trifluoromethanesulfonyloxy (hereinafter abbreviated as OTf), with bromine, iodine and OTf being most preferred.

Other substituents on ring A, ring B and ring C in Compounds (XIV) and (XV) and —X$^1$—Y$^1$ are any groups by which Suzuki reaction is not affected adversely, including those except for halogen and —OSO$_2$(C$_q$F$_{2q+1}$) wherein q is an integer of 0 to 4, and even when any of the substituents on rings A, B and C is halogen, the reaction described above can satisfactorily be advanced when the reactivity between substituents M and D is higher relatively.

Compounds (XI) and (XI') in the reaction scheme shown above may be known compounds or can be synthesized by a known method or by the following method:

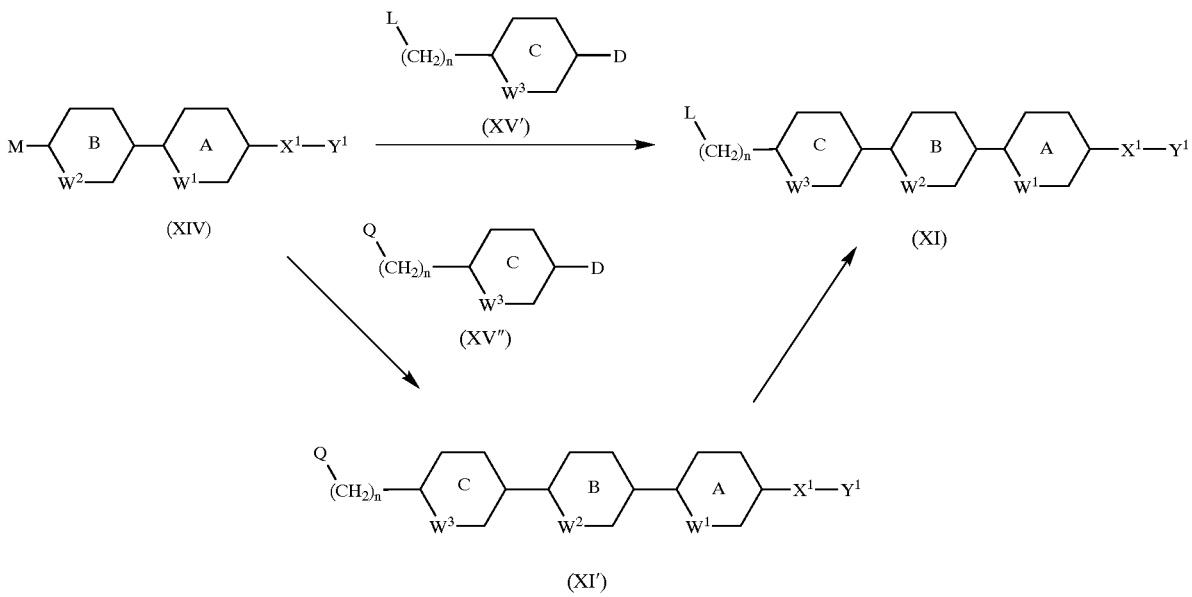

wherein substituent Q is NH$_2$ or a group by which Suzuki reaction is not affected adversely and which can be converted into substituent L by a general method, and other symbols are defined as described above.

Using Compound (XIV) which is a known compound or obtained by a method described in WO98/04508 and Compound (XV') which is a known compound or obtained from a known compound by a standard method, Compound (XI) is obtained by Suzuki reaction similarly to the steps described above. When substituent L has any adverse effect on Suzuki reaction, Compound (XV") is employed first to obtain Compound (XI") and then substituent Q is converted into substituent L.

For example, when substituent Q is hydroxy, conversion into halogen can be accomplished under a standard condition, or, an intended compound can be obtained using a suitable sulfonylating agent (for example, methanesulfonyl chloride, p-toluenesulfonyl chloride or trifluoromethane-sulfonic anhydride). Also when substituent Q is hydroxy which has previously been protected with a suitable protective group such as benzyl, t-butyldimethylsilyl or methoxymethyl, it is deprotected by a standard method into hydroxy, and subsequent procedure in accordance with the method described above results in an intended compound. Also when substituent Q is lower alkylthio or optionally substituted arylthio, each may be converted into a corresponding sulfone form using a suitable oxidizing agent (for example, hydrogen peroxide, peracetic acid, m-chloroperbenzoic acid, oxone monopersulfate compound).

Compound (XIV) employed in the reaction described above may be a known compound, or may be produced from a known compound by Suzuki reaction.

While Compound (I) is synthesized most efficiently and conveniently by employing Suzuki reaction described above, silicon, zinc or tin may also be employed instead of a boryl group in the scheme shown above as described in WO98/04508.

In the case of a compound having a substituent which interferes with a reaction described above, such group is protected first with a suitable protective group, which is then cleaved at an appropriate stage by a standard method. For example, when hydroxy interferes with a reaction, it is protected for example with methoxymethyl, methanesulfonyl, benzyl, trifluoromethanesulfonyl or t-butyldimethylsilyl, which is cleaved at an appropriate stage.

For example, when hydroxy is protected with methanesulfonyl, methanesulfonyl chloride is allowed to react in a solvent such as dichloromethane, chloroform or carbon tetrachloride in the presence of a base such as triethylamine or pyridine under cooling with ice or at room temperature for several hours. A deprotection can be effected in a solvent such as dimethylsulfoxide, N,N-dimethylformamide, tetrahydrofuran, dioxane and dimethoxyethane using 1 to 4 N sodium hydroxide, potassium hydroxide, an aqueous solution thereof, sodium methoxide or ethylmagnesium bromide at room temperature or with heating for several tens minutes to several hours.

When methoxymethyl is used to protect hydroxy, a reaction with chloromethyl methyl ether is carried out in a solvent such as tetrahydrofuran, dioxane and dimethoxyethane in the presence of sodium hydride or diisopropylethylamine, whereby forming protected hydroxy. A deprotection may ordinarily be carried out in a solvent such as methanol, tetrahydrofuran and acetic acid using hydrochloric acid or sulfuric acid.

When t-butyldimethylsilyl is used as a protective group, a reaction with t-butyldimethylsilyl chloride or t-butyldimethylsilyl triflate is carried out in a solvent such as N,N-dimethylformamide, acetonitrile, tetrahydrofuran and dichloromethane in the presence of imidazole, triethylamine or 2,6-lutidine. For a deprotection, a protective group can be cleaved by a reaction with tetrabutylammonium fluoride in a solvent such as tetrahydrofuran.

A compound according to the invention obtained as described above can further be converted into a prodrug.

The term "prodrug" is any compound that can readily be subjected to an in vivo conversion into an active compound according to the invention, and a prodrug can be obtained by any standard method. A method for selecting and producing a suitable prod rug derivative is described for example in Design of Prodrugs, Elsevier, Amsterdam, 1985. According to this reference, a group employed usually for obtaining a prodrug is introduced into carboxy, hydroxy or amino bound at any position in a compound of the invention.

For example, when hydroxy is present as a substituent on ring A or ring C, —COCH$_2$CH$_2$COOH, —COCH═CHCOOH, —COCH$_2$SO$_3$H, —PO$_3$H$_2$, —COCH$_2$NMe$_2$ and —CO—Py (Py is pyridyl) can for example be introduced.

When amino is present as a substituent on ring A or ring C, —COOCR$^h$R$^i$OCOCH$_2$R$^j$ (wherein each of R$^h$ and R$_i$ is independently hydrogen or lower alkyl, R$^j$ is H, —OH, —CONHR$^k$, —OCONHR$^k$, —(NHCOCR$^l$R$^m$)$_u$NHCOCH$_3$, —(NHCOCR$^l$R$^m$)$_u$NHCOC$_2$H$_5$, —CSNH$_2$, —(OCH$_2$CH$_2$)$_t$OH, —OCH$_3$, —(OCH$_2$CH$_2$)$_t$OCH$_3$, —COCH$_3$, —COC$_2$H$_5$, —OCOCH$_3$, —OCOC$_2$H$_5$, —NHOH, —NHCONH$_2$, —NHCSNH$_2$, —NHSO$_2$CH$_3$, —N(SO$_2$CH$_3$)$_2$, —SO$_2$NH$_2$, —SOMe, —SO$_2$CH$_3$, —OCH$_2$CONH$_2$, —OCH$_2$CON(CH$_3$)$_2$, —SO$_2$N(CH$_3$)$_2$, —PO(OCH$_3$)$_2$, —NHCSNHC$_2$H$_5$Et, —CH═NNHCONH$_2$, —CH═NNHCSNH$_2$, —CH═NNHSO$_2$CH$_3$, triazolyl, tetrazolyl and the like, each of R$^k$, R$^l$ and R$^m$ is hydrogen or lower alkyl, t is 1 or 2, u is an integer of 0 to 2), —COOCH(Me)OCOCMe$_3$, —COOCH$_2$OCO(CH$_2$)$_{14}$Me, —COOCH$_2$OCO-Pyr, —CH$_2$NHCO—C$_6$H$_4$—o—OCH$_2$OAc and the like wherein Pyr is pyridyl, Ac is acetyl can be introduced.

When introducing substituted acyloxycarbonyl (—COOCR$^h$R$^i$OCOCH$_2$R$^j$) described above into amino present at any position in a compound of the invention to form a prodrug, the amino present in any position of the compound of the invention is α-haloalkoxycarbonylated and reacted with a suitable carboxylic acid under an appropriate condition, whereby obtaining the prodrug.

A method for synthesizing such an acyloxyalkylcarbamate is described for example in WO96/18605.

Typically an amino-containing compound of the invention and α-haloalkyl chloroformate are reacted in an inert solvent (diethylether, tetrahydrofuran, 1,4-dioxane, ethyl acetate, toluene and the like) in the presence of a base (pyridine, triethylamine, N-methylmorphohne and the like) at 0° C. to room temperature to give a haloalkoxycarbamate compound. Then a compound thus obtained was reacted in a solvent (N,N-dimethylformamide, N,N-dimethylacetoamide, dimethylsulfoxide, sulfolane and the like) with a salt of a substituted carboxylic acid (for example, alkaline metal salt, alkaline earth metal salt, silver salt, mercury salt and the like) at room temperature or with heating for several hours to several days to give a prodrug compound.

A substituent interfering with the formation of a prodrug, if any, can previously be protected with an appropriate protective group and then cleaved at an appropriate stage by a standard method.

In the specification, the term "Th2 differentiation inhibitor" is a pharmaceutical composition which inhibits the differentiation from Th0 cells to Th2 cells, thus, a pharmaceutical composition for treating and/or preventing diseases induced by Th2 cells or by cytokines produced by Th2 cells.

Th2 differentiation inhibitors of the invention reduce the population of Th2 cells to give a reduction in the level of Th2 cell-derived cytokines, whereby exerting its inhibitory effects on B-cells activation and antibody production, which are associated further with the following characteristics.

An activation of B-cells while resting is believed to require a contact between Th2 cells and the B-cells as well as a stimulation of Th2 cell-derive cytokines, and Th2 differentiation inhibitors of the invention have an inhibitory effect also on the activation of the B-cells by the Th2 cells themselves. Accordingly, a more effective treatment and prevention of allergic diseases or autoimmune diseases is possible when compared with conventional anti-allergic agents.

A certain allergic diseases such as asthma and airway inflammation is known to be induced by Th2 cells themselves, and Th2 differentiation inhibitors of the invention is effective also in treating diseases against which IgE production inhibitors alone, for example, are not expected to be so effective.

Th2 differentiation inhibitors of the invention do not inhibit the differentiation from Th0 cells to Th1 cells, thus exhibiting a high Th2 selectivity. Accordingly, it shows no inhibitory effect on the protection against an infection with a virus or intracellular parasite in which Th1 cells are believed to be involved (for example, tuberculosis, leprosy, chlamydia), but inhibits advantageously the advancement of acquired immunodeficiency syndrome (AIDS), thus being an excellent pharmaceutical having less side effects.

Th2 differentiation inhibitors of the invention are effective against immune diseases classified as type-Th2 immune diseases. For example, they are used preferably as therapeutic and/or prophylactic agents against graft immune diseases (chronic GVHD), autoimmune diseases (especially organ non-specific autoimmune diseases) and type-Th2 allergic diseases. Diseases exemplified typically are ulcerative colitis, systemic lupus erythematodes, myasthenia gravis, systemic progressive scleroderma, rheumatoid arthritis, interstitial cystitis, Hashimoto's diseases, Basedow's diseases, autoimmune hemolytic anemia, idiopathic thrombocytopenic purpura, Goodpasture's syndrome, atrophic gastritis, pernicious anemia, Addison diseases, pemphigus, pemphigoid, lenticular uveitis, sympathetic ophthalmia, primary biliary cirrhosis, active chronic hepatitis, Sjogren's syndrome, multiple myositis, dermatomyositis, polyarteritis nodosa, rheumatic fever, glomerular nephritis (lupus nephritis, IgA nephtopathy, and the like), allergic encephalitis, atopic allergic diseases (for example, bronchial asthma, allergic rhinitis, allergic dermatitis, allergic conjunctivitis, pollinosis, urticaria, food allergy and the like), Omenn's syndrome, vernal conjunctivitis and hypereosinophilic syndrome. A particular effectiveness is observed especially in organ non-specific autoimmune diseases such as graft immune diseases (chronic GVHD), ulcerative colitis, systemic lupus erythematosus, myasthenia gravis, systemic progressive scleroderma, rheumatoid arthritis, lupus nephritis, interstitial cystitis and the like.

When Th2 differentiation inhibitors of the invention are administered, it can be given orally and parenterally. When administered orally, a formulation employed customarily such as tablet, granule, powder, capsule, pill, solution, syrup, buccal or sublingual formulation may be given in a standard manner. When administered parenterally, a formulation employed customarily such as intramuscular or intravenous injection formulation, suppository, percutaneous absorption and inhalation formulations can preferably be given. An oral administration is particularly preferred.

An effective amount of a compound according to the invention can be mixed if necessary with various pharmaceutical additives suitable for its particular dosage form such as excipient, binder, lubricant, disintegrant, lubricant, diluent and the like to form a pharmaceutical formulation. A formulation for injection may be prepared using a suitable vehicle to be sterilized simultaneously.

Those exemplified typically are lactose, sugar, glucose, starch, calcium carbonate or crystalline cellulose as an excipient, methyl cellulose, carboxymethyl cellulose, hydroxypropyl cellulose, gelatin or polyvinyl pyrrolidone as a binder, carboxymethyl cellulose, sodium carboxymethyl cellulose, starch, sodium alginate, agar power or sodium laurylsulfate as a disintegrant, talc, magnesium stearate or Macrogol as a lubricant. A suppository base may for example be cocoa butter, Macrogol and methylcellulose. A liquid, emulsion or suspension formulation for injection may be formulated using customarily employed solubilizing agent, suspending agent, emulsifier, stabilizer, preservative, isotonizing agent and other additives, and an oral formulation may contain sweetening agents and flavors.

Th2 differentiation inhibitors of the invention can be given alone or in combination with other anti-allergic agents if necessary. An agent which can be employed in combination may for example be a steroid, a known anti-allergic agent and a bronchodilator.

White the dose of Th2 differentiation inhibitors of the invention are adjusted preferably on the basis of patient's age, body weight, type and severity of the diseases as well as the administration route, it is usually 0.05 to 100 mg/kg/day; preferably 0.1 to 10 mg/kg/day in adults. While the dose when given parenterally varies greatly depending on the administration route, it is usually 0.0001 to 10 mg/kg/day preferably 0.001 to 1 mg/kg/day. Such dose may be divided into several portions, which are given over a day.

The present invention is further described in the following Examples, which are not intended to restrict the invention.

EXAMPLES

Reference Example 1

Synthesis of Compound (I-6)

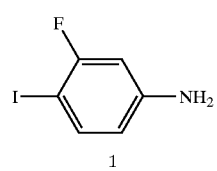

1

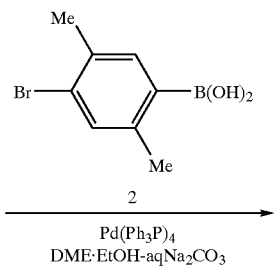

2

Pd(Ph$_3$P)$_4$
DME·EtOH-aqNa$_2$CO$_3$

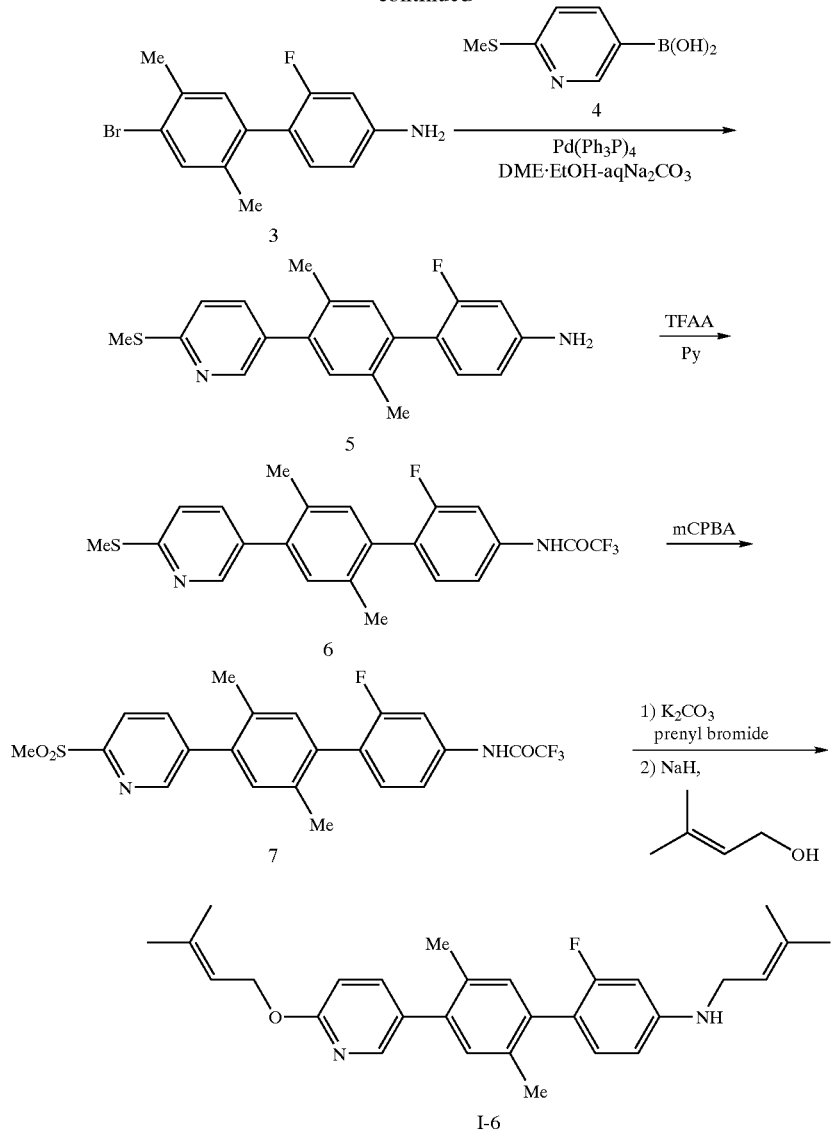

(Step 1)

To a solution of Compound (1) (23.7 g, 0.1 mol) in dimethoxyethane (300 ml)-ethanol (150 ml), an aqueous solution (150 ml) of boronic acid (2) (22.88&g, 0.1 mol) and sodium carbonate (31.8 g, 0.3 mol) was added and the reaction mixture was deaerated. Tetrakis(triphenylphosphine)palladium (3.47 g, 3 mmol) was added and the mixture was heated under reflux under nitrogen atmosphere for 2 hours, and then diluted with water and extracted with ethyl acetate. The extract was washed with saturated brine, dried, concentrated, and the resultant residue was crystallized from hexane to obtain Compound (3) (24.92g, yield: 84%).

(Step 2)

Similarly to Step 1, Compound (3) (20.0 g, 68.0 mmol) and boronic acid (4) (14.94 g, 88.3 mmol) were reacted for 18 hours and the extraction residue was purified by a chromatography on silica gel (hexane:ethyl acetate=2:1) to obtain Compound 5 (19.24 g; Yield: 84%).

(Step 3)

To a solution of Compound (5) (21.15 g, 62.5 mmol) in dichloromethane (200 ml) under cooling on ice, pyridine (6.6 ml, 81.2 mmol) and then trifluoroacetic anhydride (10.6 ml, 75.0 mmol) were added, and the mixture was stirred at room temperature for 1 hour. The reaction mixture was diluted with ethyl acetate, and then washed successively with water, 1 N hydrochloric acid and a 5% aqueous solution of sodium hydrogen carbonate, dried, concentrated to give Compound (6) (22.80 g; Yield: 84%).

(Step 4)

To a solution of Compound (6) (14.0 g, 32.2 mmol) in dichloromethane (300 ml) under cooling on ice, m-chloroperbenzoic acid (14.46 g, 83.8 mmol) was added and the mixture was stirred at room temperature for 3 hours. The reaction mixture was combined with an aqueous solution of sodium thiosulfate, extracted with ethyl acetate, washed twice with an saturated aqueous solution of sodium hydrogen carbonate, dried and concentrated. The residue was washed with hexane to obtain Compound (7) (12.97 g; Yield 86%).

(Step 5)

A solution of Compound (7) (15.0 g, 32.2 mmol) in DMF (65 ml) was combined with potassium carbonate (6.67 g, 48.2 mmol) followed by prenyl bromide (4.81 ml, 41.8 mmol), and then stirred for 18 hours at room temperature. The reaction mixture was diluted with ethyl acetate, washed successively with water and saturated brine, dried and concentrated to obtain a residue, which was then dissolved in tetrahydrofuran (150 ml). A reaction mixture prepared by adding sodium hydride (60% in mineral oil, 3.85 g, 96.5 mmol) to a solution of prenol (9.8 ml, 96.5 mmol) in tetrahydrofuran (150 ml) was added under cooling on ice, and the mixture was stirred further for 2 hours at the same temperature. The reaction mixture was diluted with ethyl acetate, washed successively with water and saturated brine, dried and concentrated. The residue was purified by a chromatography on silica gel (hexane:ethyl acetate=7:1) to obtain Compound (a-6) (12.5 g; Yield: 87%).

mp 87 to 88° C.

$^1$H NMR (CDCl$_3$) δH1.74 (s, 3H), 1.78 (s, 3H), 1.79 (s, 3H), 1.80 (s, 3H), 2.22 (s, 3H), 2.26 (s, 3H), 3.71 (d, J=6.9 Hz, 2H), 4.87 (d, J=7.2 Hz, 2H), 5.32–5.37 (m, 1H), 5.55–5.60 (m, 1H), 6.35–6.47 (m, 2H), 6.81 (dd, J=0.6, 8.4 Hz, 1H), 7.02–7.13 (m, 3H), 7.59 (dd, J=2.4, 8.4 Hz, 1H), 8.16 (dd, J=0.9, 5.7 Hz, 1H) ppm.

IR (Nujol): 3330, 2923, 2853, 1627, 1606, 1564, 1527, 1481, 1471, 1395, 1376, 1357, 1337, 1284, 1240, 1178, 1116, 990 cm$^{-1}$ Reference Example 2 Synthesis of Compound (I-134)

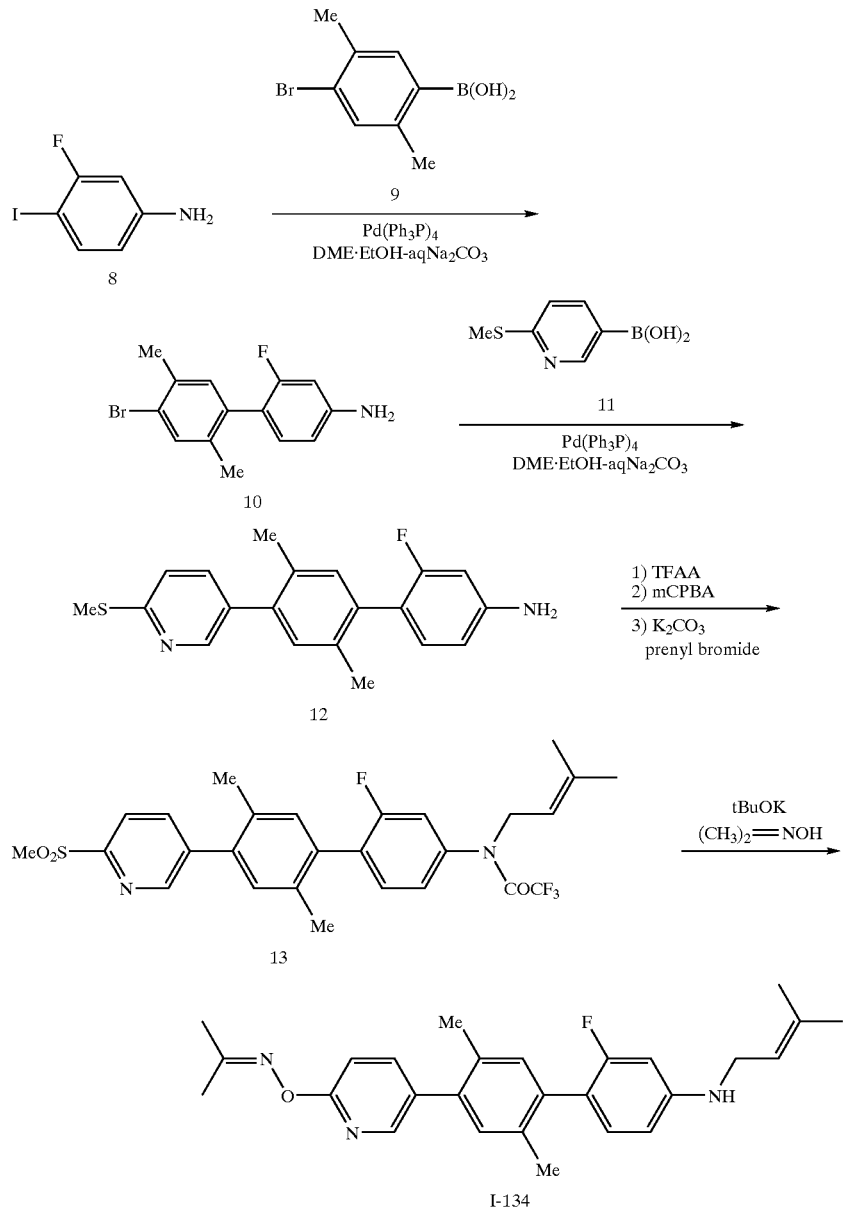

I-134

(Step 1)

To a solution of Compound (8) (23.7 g, 0.1 mol, Journal of Organic Chemistry, 1961 (26) 3351–3356) in dimethoxyethane (300 ml)—ethanol (150 ml), boronic acid (9) (22.88 g, 0.1 mol) and an aqueous solution (150 ml) of sodium carbonate (31.8 g, 0.3 mol) was added and the reaction mixture was deaerated. Tetrakis (triphenylphosphine) palladium (3.47 g, 3 mmol) was added and the mixture was heated under reflux under nitrogen atmosphere for 2 hours, and then diluted with water and extracted with ethyl acetate. The extract was washed with saturated brine, dried and concentrated, and the resultant residue was crystallized from hexane to obtain Compound (10) (24.92g, yield: 84%).

(Step 2)

Similarly to Step 1, Compound (12) (1.56 g; Yield: 92%) was obtained from Compound (10) (1.47 g, 5 mmol) and boronic acid (11) (1.01 g, 6 mmol).

(Step 3)

To a solution of Compound (12) (1.56 g, 4.62 mmol) in dichloromethane (5 ml) under cooling on ice, pyridine (0.56 ml, 6.92 mmol) and then trifluoroacetic anhydride (0.78 ml, 5.54 mmol) were added, and the mixture was stirred at room temperature for 1 hour. The reaction mixture was diluted with ethyl acetate, and then washed successively with water, a 5% aqueous solution of sodium hydrogen carbonate and saturated brine, and then dried and concentrated. The residue dissolved in dichloromethane (16 ml) was treated under cooling on ice with m-chloroperbenzoic acid (2.0 g, 11.6 mmol) and stirred at room temperature for 3 hours. The reaction mixture was treated with an aqueous solution of sodium thiosulfate and extracted with chloroform, washed twice with a 5% aqueous solution of sodium hydrogen carbonate, dried and then concentrated. The residue was dissolved in N,N-dimethylformamide (8 ml), combined with potassium carbonate (720 mg, 5.21 mmol) followed by prenyl bromide (0.52 ml, 4.34 mmol), and stirred at room temperature for 14 hours. The reaction mixture was diluted with ethyl acetate, washed successively with water and saturated brine, dried and concentrated. The residue was purified by a chromatography on silica gel (hexane:ethyl acetate=2:1) to obtain Compound (13) (1.71 g; Yield: 69%).

(Step 4)

To a solution of acetoxime (137 mg, 1.87 mmol) in N,N-dimethylformamide (3 ml), sodium hydride (60% in mineral oil, 137 mg, 1.87 mmol) was added, and the mixture was stirred at room temperature for 1 hour, and then Compound (13) (250 mg, 0.468 mmol) was further added. The mixture was stirred at room temperature for 14 hours, diluted with ethyl acetate, washed successively with a 5% aqueous solution of citric acid and saturated brine, dried and concentrated. The residue was purified by a chromatography on silica gel (hexane:ethyl acetate=7:3) to obtain Compound (I-134) (126 mg; Yield: 62%).

mp 135 to 137° C.; $^1$H NMR (CDCl$_3$) δ 1.74 (s, 3H), 1.78 (s, 3H), 2.09 (s, 3H), 2.16 (s, 3H), 2.22 (s, 3H), 2.26 (s, 3H), 3.72 (d, J=6.6 Hz, 2H), 3.90 (br s, 1H), 5.35 (m, 1H), 6.39 (dd, J=2.4, 12.3 Hz, 1H), 6.46 (dd, J=2.4, 8.4 Hz, 1H), 7.06 (t, J=8.4 Hz, 1H), 7.12 (s, 1H), 7.13 (s, 1H), 7.23 (dd, J=0.6, 8.7 Hz, 1H), 7.70 (dd, J=2.4, 8.7 Hz, 1H), 8.28 (dd, J=0.6, 2.4 Hz, 1H) ppm.

Reference Example 3

Synthesis of Compound (9)

A suspension of 1,4-dibromo-2,5-dimethylbenzene (154 g, 583 mmol) in tetrahydrofuran (1.3 L) was cooled to −78° C., and a 1.53 M solution of butyllithium hexane (400 ml, 612 mmol) was added dropwise over 30 minutes. After stirring the reaction mixture at the same temperature further for 1 hour, triisopropyl borate (170 ml, 734 mmol) was added at once and the cooling medium was removed to allow the mixture to warm with stirring for 1 hour. After adding water (300 ml) and 1 N hydrochloric acid (650 ml), the mixture was extracted with ethyl acetate, and the extract was washed with water and saturated brine, dried and concentrated. A crystalline residue was washed with hexane and filtered to give Compound (9) (115 g; Yield 86%).

Reference Example 4

Synthesis of Compound (11)

A solution of a 1.53 M solution of butyllithium—hexane (500 ml, 765 mmol) in tetrahydrofuran (1.28 L) was cooled to −78° C., and a solution of 5-bromo-2-methylchiopyridine (142 g, 695 mmol) in tetrahydrofuran (400 ml) was added dropwise over 40 minutes. After stirring the reaction mixture at the same temperature further for 30 minutes, triisopropyl borate (195 ml, 834 mmol) was added dropwise over 30 minutes. The cooling medium was removed, and the mixture was allowed to warm with stirring for 30 minutes. After adding water (320 ml), the mixture was concentrated under reduced pressure and the residue was diluted again with water (710 ml) and isopropylether (210 ml). The reaction mixture was stirred at room temperature with a dropwise addition of 3 N hydrochloric acid (675 ml), and the precipitating crystal was filtered, washed with water and isopropylether and dried to obtain Compound (11) (111 g; Yield: 95%).

mp 151 to 154° C.

Anal Calcd for C$_6$H$_8$BNO$_2$S: C, 42.64; H, 4.77; N, 8.29; S, 18.97.

Found: C, 42.56; H, 4.88; N, 8.14; S, 18.79.

$^1$H-NMR(DMSO-d$_6$) δ 2.51 (s, 3H), 7.25 (dd, J=0.9, 8.1 Hz, 1H), 7.93 (dd, J=2.1, 8.1 Hz, 1H), 8.73 (dd, J=0.9, 2.1 Hz, 1H) ppm.

Reference Example 5

Synthesis of Compound (I-179)

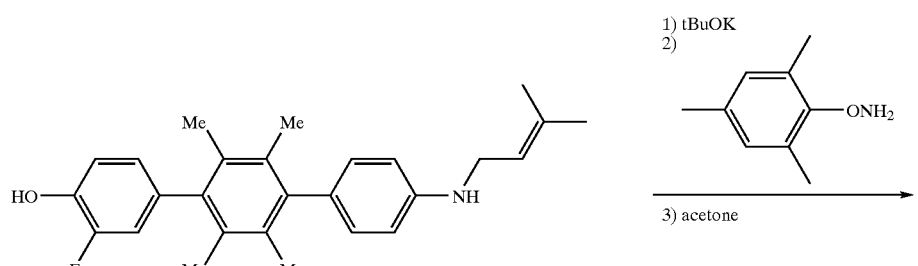

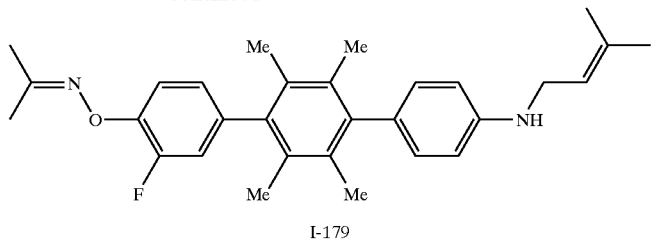

I-179

A solution of Compound (14) (261 mg, 0.65 mmol), which was obtained by a method described in WO98/04508, in methanol (4 ml) was cooled to 0° C., treated with potassium t-butoxide (75 mg, 0.65 mmol) and stirred for 15 minutes. After distilling the solvent off under reduced pressure followed by drying, the residue was dissolved in N,N-dimethylformamide (2.5 ml). O-Mesithylene sulfonyl hydroxylamine (Journal of Organic Chemistry, 1973 (38) 1239–1241) (251 mg, 1.16 mmol) was added, and the reaction mixture was stirred for 1 hour, poured into water, and extracted with ethylether:ethyl acetate (1:1). The extract was washed with water and saturated brine, dried, concentrated to obtain a residue, which was dissolved in methanol (3 ml), combined with acetone (0.48 ml, 6.5 mmol) and stirred at room temperature for 1 hour. The reaction mixture was concentrated, and the residue was purified by a chromatography on silica gel (hexane:ethyl acetate=10:1) to obtain Compound (I-179) (118 mg; Yield: 40%).

mp 129 to 130° C.; $^1$H NMR (CDCl$_3$) δ 1.74 (s, 3H), 1.78 (s, 3H), 1.96 (s, 6H), 1.98 (s, 6H), 2.06 (s, 3H), 2.15 (s, 3H), 3.60 (br s, 1H), 3.74 (d, J=6.6 Hz, 2H), 5.40 (m, 1H), 6.69 (d, J=8.7 Hz, 2H), 6.87–6.98 (m, 4H), 7.48 (t, J=8.4 Hz, 1H) ppm.

Reference Example 6

Synthesis of Compound (I-235)

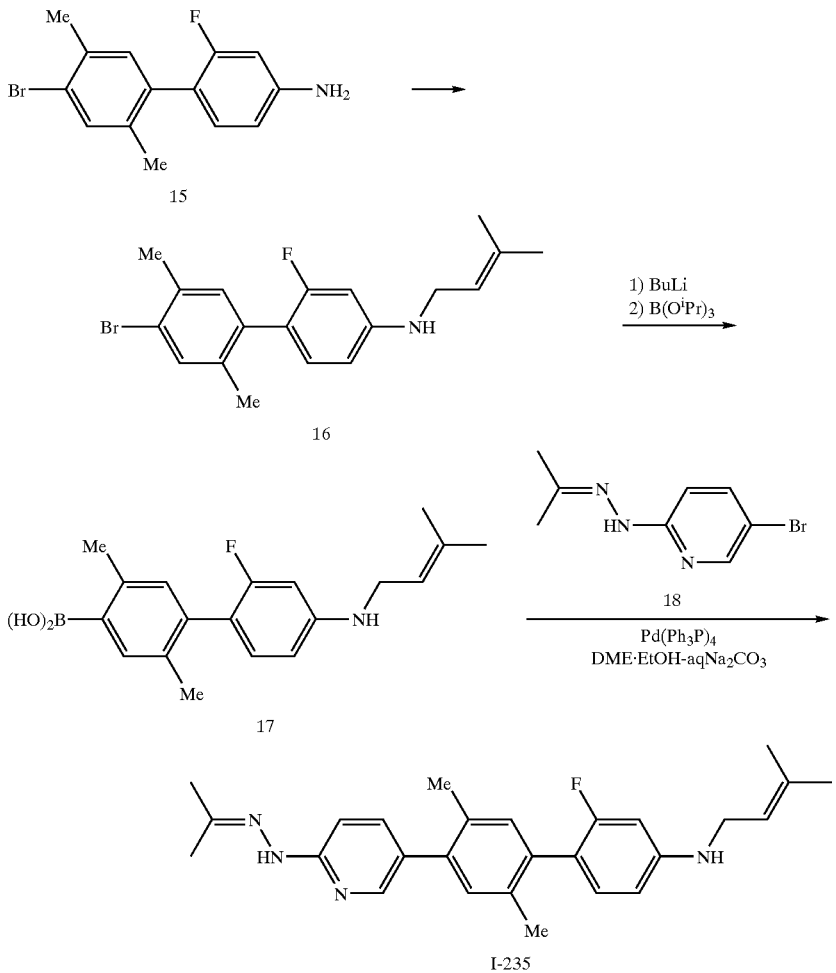

(Step 1) Synthesis of Compound (16)

To a solution of Compound (15) (4.41 g, 15.0 mmol) in dichloromethane (45 ml), 3-methyl-2-butenal (1.74 ml, 18.0 mmol), acetic acid (1.8 g, 30.0 mmol) and sodium triacetoxyborohydride (6.36 g, 30.0 mmol) were added successively, and the reaction mixture was stirred for 15 hours. The reaction mixture was poured into water, extracted with ethyl acetate, and the extract was washed with an aqueous solution of sodium hydrogen carbonate and saturated brine, dried and concentrated. The residue was purified by a chromatography on silica gel (hexane:ethyl acetate=9:1) to obtain Compound (16) (4.09 g; Yield: 75%).

(Step 2) Synthesis of Compound (17)

A solution of Compound (16) (2.4 g, 6.62 mmol) in tetrahydrofuran (24 ml) was cooled to −78° C., and treated dropwise with 1.53 M butyllithium (10.4 ml, 15.9 mmol) over 30 minutes. After stirring the reaction mixture for further 2 hours followed by adding triisopropyl borate (5.5 ml, 23.8 mmol), the cooling medium was removed and the mixture was allowed to warm to room temperature with stirring for 30 minutes the reaction mixture was poured into water, which was then extracted with ethyl acetate, and the extract was washed with an aqueous solution of ammonium chloride and saturated brine, dried and concentrated. The crystalline residue was washed with hexane and filtered to obtain Compound (17) (1.82 g; Yield: 87%).

$^1$H-NMR(DMSO-$d_6$) δ 1.70 (s, 3H), 1.72 (s, 3H), 2.12 (s, 3H), 2.63 (s, 3H), 3.63 (br t, 2H), 5.28 (br t, 1H), 6.01 (br t, 1H), 6.37 (dd, J=2.1, 13.2 Hz, 1H), 6.46 (dd, J=2.1, 8.4 Hz, 1H), 6.92(s, 1H), 6.97 (t, J=8.4 Hz, 1H), 7.77 (s, 1H) ppm.

(Step 3) Synthesis of Compound (I-235)

Similarly to Step 1 in Reference Example 2, Compound (I-235) (268 mg; Yield: 83%) was obtained from Compound (18) (175 mg, 0.75 mmol) and boronic acid (17) (245 mg, 0.75 mmol).

foam; $^1$H NMR (CDCl$_3$) δ 1.74 (s, 3H), 1.78 (s, 3H), 1.93 (s, 3H), 2.08 (s, 3H), 2.22 (s, 3H), 2.27 (s, 3H), 3.72 (br d, J=5.4 Hz, 2H), 3.77 (br s, 1H), 5.35 (m, 1H), 6.38 (dd, J=2.4 Hz, 12.3, 1H), 6.45 (dd, J=2.4, 8.4 Hz, 1H), 7.06 (t, J=8.4 Hz, 1H), 7.12 (s, 1H), 7.13 (s, 1H), 7.27 (d, J=8.4 Hz, 1H), 7.61 (dd, J=2.1, 8.4 Hz, 1H), 7.68 (br s, 1H), 8.13 (d, J=2.1 Hz, 1H) ppm.

Reference Example 7

Synthesis of Compound (18)

5-Bromo-2-hydrazinopyridine (Journal of Heterocyclic Chemistry, 1986 (23) 1071) (376 mg, 2.0 mmol) was heated under reflux for 15 minutes in acetone (1 ml) and ethanol (4 ml). The reaction mixture was concentrated to obtain Compound (18) as a crystaline residue (456 mg, quantitative yield).

Reference Example 8

Synthesis of Compound (I-189)

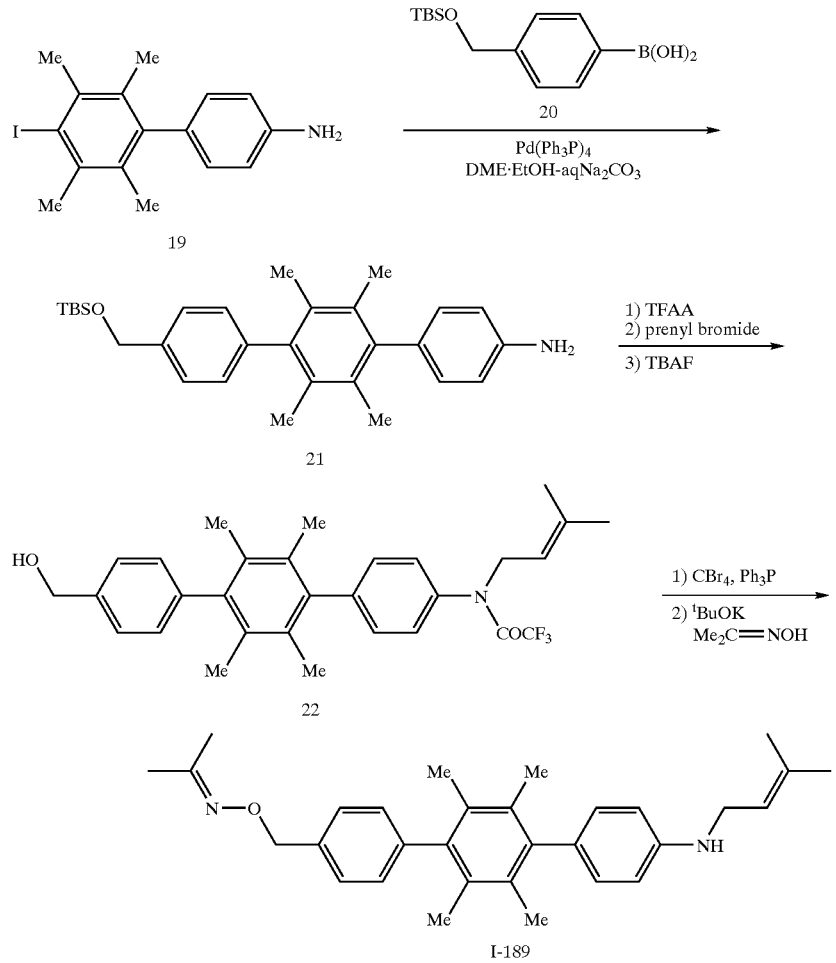

(Step 1) Synthesis of Compound (21)

To a solution of Compound (19) (500 mg, 1.42 mmol) in dimethoxyethane (6 ml)—ethanol (1.5 ml), boronic acid (20) (624 mg, 1.57 mmol) and a 2 M aqueous solution of sodium carbonate (3 ml) were added, and the reaction mixture was deaerated. Tetrakis(triphenylphosphine)palladium (49 mg, 0.04 mmol) was added, and the mixture was heated under reflux under nitrogen atmosphere for 18 hours, cooled, diluted with water, and then extracted with ethyl acetate. The extract was washed with saturated brine, dried, concentrated to obtain a residue, which was purified by a chromatography on silica gel (hexane:ethyl acetate=4:1) to obtain Compound (21) (604 mg; Yield: 95%).

(Step 2) Synthesis of Compound (22)

To a solution of Compound (21) (604 mg, 1.36 mmol) in tetrahydrofuran (6 ml) under cooling on ice, triethylamine (0.28 ml, 2.03 mmol) and then trifluoroacetic anhydride (0.23 ml, 1.63 mmol) were added and the mixture was stirred for 15 minutes. The reaction mixture was diluted with ethyl acetate, and then washed successively with water and saturated brine, dried and concentrated.

A solution of a crude product in N,N-dimethylformamide (4 ml) was combined with potassium carbonate (375 mg, 2.71 mmol) followed by prenyl bromide (0.31 ml, 2.71 mmol) and stirred at room temperature for 3 hours. The reaction mixture was poured into water, extracted with ethyl acetate—ethylether (1:1), and the extract was washed successively with water and saturated brine, dried and concentrated. The residue was purified by a chromatography on silica gel (hexane:ethyl acetate=19:1) and dissolved in tetrahydrofuran (8 ml). Under cooling on ice, a 1 M tetrabutylammonium fluoride solution in tetrahydrofuran(0.15 ml, 1.5 mmol) was added, and the mixture was stirred for 1 hour. The reaction mixture was poured into water, extracted with ethyl acetate, and the extract was washed with saturated brine, dried and concentrated. The residue was purified by a chromatography on silica gel (hexane:ethyl acetate=3:1) to obtain Compound (22) (543 mg; Yield: 81%).

(Step 3) Synthesis of Compound (I-189)

A solution of Compound (22) (236 mg, 0.48 mmol) in dichloromethane (4 ml) under cooling on ice was treated with triphenylphosphine (162 mg, 0.62 mmol) followed by carbon tetrabromide (205 mg, 0.62 mmol) and stirred for 30 minutes. The reaction mixture was diluted with ethyl acetate, washed successively with water and saturated brine, dried and concentrated. The residue was purified by a chromatography on silica gel (hexane:ethyl acetate=9:1) and dissolved in N,N-dimethylformamide (3 ml).

To a solution of acetoxime (139 mg, 1.9 mmol) in N,N-dimethylformamide (2 ml), potassium t-butoxide (187 mg, 1.67 mmol) was added and the mixture was stirred at room temperature for 30 minutes and then cooled to 0° C. This reaction mixture was combined with a solution of the bromide in N,N-dimethylformamide, and stirred at room temperature for 3 hours. The reaction mixture was poured into water, extracted with ethylether:ethyl acetate (1:1), and the extract was washed with saturated brine, dried and concentrated. The residue was purified by a chromatography on silica gel (hexane:ethyl acetate=10:1) and crystallized from ethylether—hexane to obtain Compound (I-189) (117 mg; Yield: 54%).

mp 127.5–128.5° C.; $^1$H NMR (CDCl$_3$)™ 1.73 (s, 3H), 1.78 (s, 3H), 1.92 (s, 3H), 1.95 (s, 9H), 1.99 (s, 6H), 3.76 (d, J=6.6 Hz, 2H), 5.15 (s, 2H), 5.41 (m, 1H), 6.74 (d, J=8.1 Hz, 2H), 7.00 (d, J=8.1 Hz, 2H), 7.16 (d, J=8.1 Hz, 2M), 7.41 (d, J=8.1 Hz, 2H) ppm Reference Example 9

Synthesis of Compound (I-80)

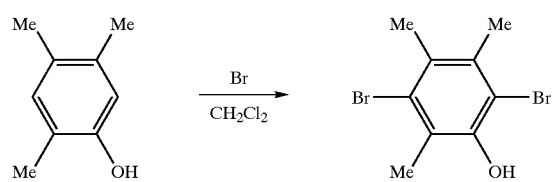
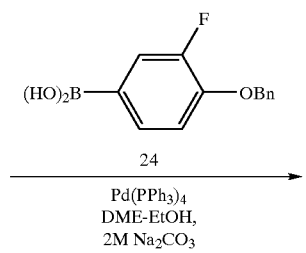
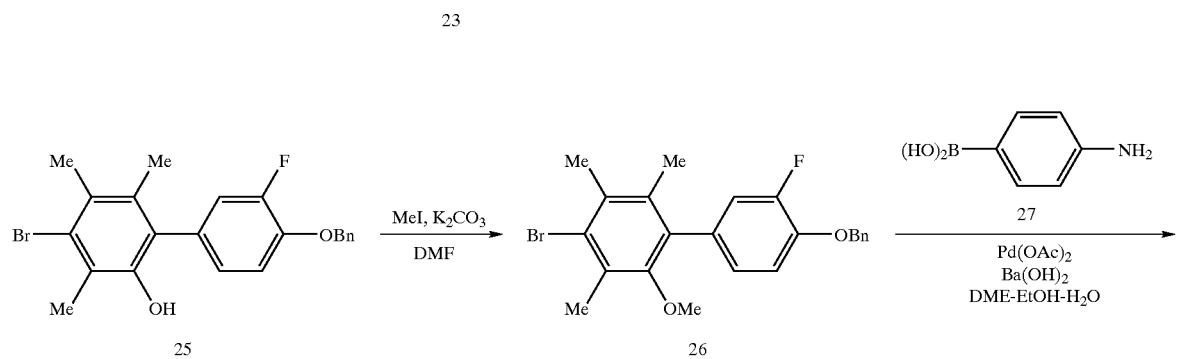

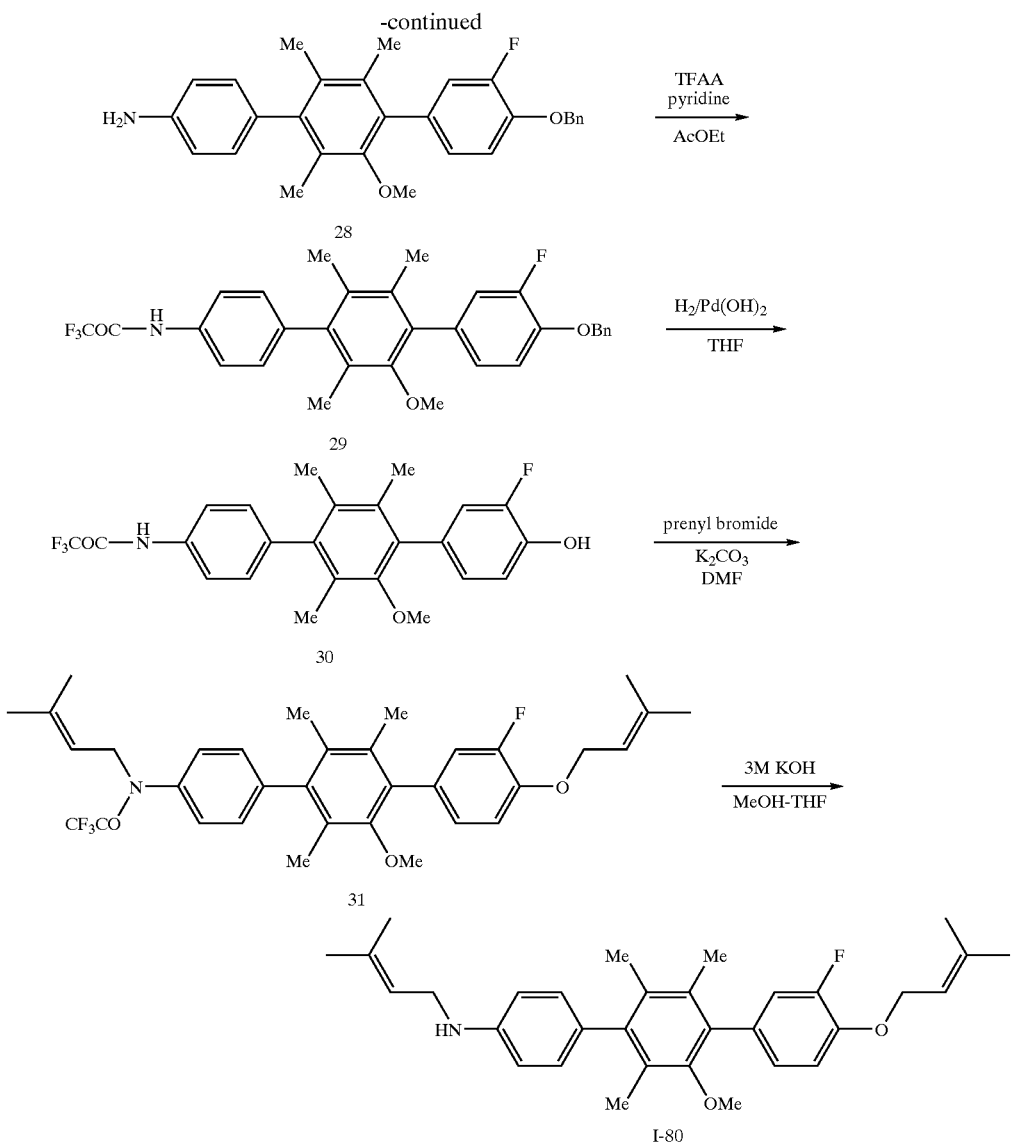

(Step 1)

TO a solution of 2,4,5-trimethylphenol (68.0, 0.5 mol) in dichloromethane (450 ml), a solution of bromine (52.8 ml, 1.03 mol) in dichloromethane (150 ml) was added dropwise under cooling on ice over a period of 1 hour and 23 minutes. After the dropwise addition, the mixture was stirred further for 2 hours and 40 minutes. To a mixture of sodium hydrogen carbonate (100 g), sodium thiosulfate pentahydrate (60 g) and water (1 L), the reaction mixture was added with stirring vigorously. The reaction mixture was extracted twice with dichloromethane, and the extract was dried over anhydrous magnesium sulfate and concentrated under reduced pressure. The residue was crystallized from hexane to obtain Compound (23) (117 g; Yield: 80%).

mp 138 to 142° C.

(Step 2)

To a solution of Compound (23) (88.2 g, 0.3 mol) in dimehtoxyethane (600 ml) ethanol (300 ml), an aqueous solution (600 mL) of boronic acid (24) (73.8 g, 0.3 mol) and sodium carbonate (127 g, 1.2 mol) was added and the reaction mixture was deaerated. Tetrakis(triphenylphosphine)palladium (17.3 g, 15 mmol) was added and the mixture was heated under reflux under nitrogen atmosphere for 3 hours. The reaction mixture was combined with 4 N hydrochloric acid (600 ml) and extracted with ethyl acetate. The extract was washed with water, a saturated aqueous solution of sodium hydrogen carbonate and saturated brine, dried and concentrated to obtain a residue, which was crystallized from methanol to obtain Compound (25) (92.9 g; Yield: 75%).

mp 148 to 150° C.

(Step 3)

To a solution of Compound (25) (83.0 g, 0.2 mol) in N,N-dimethylformamide (500 ml), potassium carbonate (30.4 g, 0.22 mol) and methyl iodide (13.7 ml, 0.22 mol) were added and the mixture was stirred at room temperature for 24 hours. The reaction mixture was combined with 1 N hydrochloric acid (220 ml) and water (300 ml) and extracted with ethyl acetate. The extract was washed with water and saturated brine, dried and concentrated to obtain a residue, which was crystallized from methanol to obtain Compound (26) (78.5 g; Yield 92%).

mp 112 to 114° C.

(Step 4)

To a solution of Compound (26) (73.0 g, 170 mmol) in dimethoxyethane (500 ml)—ethanol (100 ml), boronic acid (27) (27.4 g, 200 mmol), barium hydroxide octahydrate (126 mg, 400 mmol) and water (100 ml) were added, and the reaction mixture was deaerated. Palladium acetate (0.4 g, 1.78 mmol) was added, and the mixture was heated under reflux under nitrogen atmosphere for 1 hour, palladium acetate (0.4 g, 1.78 mmol) was further added, and the mixture was heated under reflux for further 7 hours. To the reaction mixture, activated charcoal (10 g) was added, and the mixture was filtered through celite and concentrated. The residue was dissolved in ethyl acetate (1 L), washed with water, dried and concentrated. Under cooling on ice, the residue was combined with 4 N hydrogen chloride—ethyl acetate solution (85 ml) was added, and the precipitated hydrochloride was recovered by filtration. The hydrochloride was combined with a 1 N aqueous solution of sodium hydroxide (170 ml), and extracted with ethyl acetate. The extract was washed with water, saturated brine, a saturated aqueous solution of sodium hydrogen carbonate and saturated brine, dried, concentrated, and crystallized from methanol to obtain Compound (28) (47.8 g; Yield: 64%).

mp 151 to 153° C.

(Step 5)

To a solution of Compound (28) (40.0 g, 90.6 mmol) in ethyl acetate (300 ml) under cooling on ice, pyridine (8.9 ml, 110 mmol) and then trifluoroacetic anhydride (14.1 ml, 100 mmol) were added and the mixture was stirred for 20 minutes. The reaction mixture was washed successively with an aqueous solution of ammonium chloride, water, an aqueous solution of sodium hydrogen carbonate and saturated brine, dried, concentrated and crystallized from ethyl acetate—hexane to obtain Compound (29) (47.5 g; Yield: 98%).

mp 167 to 169° C.

(Step 6)

To a solution of Compound (29) (45.0 g, 83.7 mmol) in tetrahydrofuran (300 ml), 20% palladium hydroxide/carbon (3.0 g) was added, and the mixture was stirred under hydrogen atmosphere at room temperature for 3 hours. The catalyst was filtered off, and the reaction mixture was concentrated and crystallized from ethyl acetate—hexane to obtain Compound (30) (37.1 g; Yield: 99%).

mp 242 to 244° C.

(Step 7)

To a solution of Compound (30) (36.0 g, 80.5 mmol) in DM (400 ml), potassium carbonate (25.0 g, 181 mmol) was added and then prenyl bromide (19.9 ml, 173 mmol) was added dropwise under cooling on ice over 5 minutes. After stirring at room temperature for 18 hours, potassium carbonate (5.5 g, 40 mmol) and prenyl bromide (4.6 ml, 40 mmol) were added and the mixture was stirred further for 1 hour. The reaction mixture was combined with 1 N hydrochloric acid (250 ml) and water (250 ml), and extracted with ethyl acetate. The extract was washed with water and saturated brine, dried, and concentrated to obtain a crude product of Compound (31) as an oil. This product was used in the next reaction without further purification.

(Step 8)

The crude product of Compound (31) obtained as described above was dissolved in tetrahydrofuran (100 ml)—methanol (500 ml) and treated under cooling on ice with a 3 N aqueous solution of potassium hydroxide (80 ml) and stirred for 2 hours. The precipitated crystal was recovered by filtration and then washed with water and methanol. The resultant crystal was purified by a chromatography on silica gel (hexane:ethyl acetate=10:1) and crystallized from ethanol (250 ml) to obtain Compound (I-80) (31.3 g; Yield: 80%).

mp 106 to 108° C. (EtOH);

$^1$H NMR (CDCl$_3$) δ 1.74 (s, 3H), 1.77 (s, 3H), 1.78 (s, 3H), 1.82 (s, 3H), 1.988 (s, 3H), 1.992 (s, 3H), 2.03 (s, 3H), 3.34 (s, 3H), 3.70 (brs, 1H), 3.74 (d, J=6.7 Hz, 2H), 4.64 (d, J=7.0 Hz, 2H), 5.36–5.42 (m, 1H), 5.54–5.60 (m, 1H), 6.69 (d, J=8.9 Hz, 2H), 6.96 (d, J=8.5 Hz, 2H), 6.98–7.25 (m,, 3H) ppm;

IR (nujor): 3438, 2927, 2854, 1612, 1518, 1466, 1292, 991, 816 cm$^{-1}$;

Anal Calcd for C$_{32}$H$_{38}$FNO$_2$: C, 78.82; H, 7.85; N, 2.87, F, 3.90.

Found: C, 78.92; H, 7.67; N, 2.96, F, 3.82.

Reference Example 10

Synthesis of other Compounds (I)

The following Compounds (I) were synthesized similarly to Reference Example 9.

(I-89)

mp 93 to 94.5° C.;

$^1$H NMR (CDCl$_3$, 300 MHz) δ 1.74 (s, 3H), 1.77 (s, 6H), 1.82 (s, 3H), 1.57 (s, 3H), 1.96 (s, 3H), 2.06 (s, 3H), 3.32 (s, 3H), 3.75 (d, J=6.9 Hz, 2H), 4.64 (d, J=6.9 Hz, 2H), 5.37–5.42 (m, 1H), 5.54–5.60 (m, 1H), 6.71 (d, J=7.8 Hz, 2H), 6.85 (dq, J=8.3, 1.1 Hz, 1H), 6.92 (dd, J=12.0, 1.8 Hz, 1H), 7.04 (t, J=8.6 Hz, 1H), 7.13 (d, J=8.7 Hz, 2H) ppm;

IR (Nujol) 3437, 1610, 1576, 1518, 1292, 1242, 1115, 991, 814 cm-1;

Anal Calcd for C$_{32}$H$_{38}$FNO$_2$: C, 78.82; H, 7.85; F, 3.90; N, 2.87.

Found: C, 78.90; H, 7.92; F, 3.78; N, 3.11.

(I-102)

mp 143 to 144° C.; $^1$H NMR (300 MHz, CDCl$_3$) δ 1.75 (s, 3H), 1.79 (s, 3H), 2.06 (s, 3H), 2.09 (s, 3H), 3.35 (s, 3H), 3.36 (s, 3), 3.78 (t, J=6.0 Hz, 2H), 3.83–3.94 (m, 3H), 4.53 (br s, 1H), 5.34–5.44 (m, 2H), 6.48 (dd, J=8.4, 0.9 Hz, 1H), 6.73–6.79 (m, 1), 6.92–6.98 (m, 2), 7.43 (dd, J=8.4, 2.4 Hz, 1H), 8.05 (dd, J=2.4, 0.6 Hz, 1H) ppm.

(I-108)

mp 96 to 97° C.; $^1$H NMR (CDCl$_3$) δ 1.74 (s, 3H), 1.79 (s, 6H), 1.82 (s, 3H), 2.05 (s, 6), 2.18 (s, 3H), 3.74 (d, J=6.6 Hz, 2H), 4.87 (d, J=7.2 Hz, 2H), 5.39 (t, J=6.9 Hz, 1H), 5.58 (t, J=7.2 Hz, 1H), 6.70 (d, J=8.4 Hz, 2H), 6.81 (d, J=8.4 Hz, 1), 6.96–6.99 (m, 3H), 7.57 (dd, J=0.9, 8.7 Hz, 1H), 8.16 (d, J=2.1 Hz, 1H) ppm; IR (KBr): 3345, 2972, 2913, 1613, 1560, 1522, 1490, 1466, 1281, 1240, 982, 827 cm$^{-1}$ (I-55)

mp 84 to 86° C.; $^1$H NMR (CDCl$_3$) δ 1.74 (s, 3H), 1.77 (s, 3H), 1.79 (s, 3H), 2.23 (s, 3), 2.28 (s, 3H), 3.71 (d, J=6.9 Hz, 2), 4.93 (d, J=6.9 Hz, 2H), 5.32–5.61 (m, 2H), 6.36–6.48 (m, 2), 7.05 (t, J=8.4 Hz, 1H), 7.09(s, 1H), 7.15(s, 1H), 8.53 (s, 2H) ppm, IR (KBr): 3224, 3315, 2970, 2923, 1628, 1592, 1534, 1474, 1438, 1377, 1341, 1317, 1249, 1173, 1110, 993 cm-1.

(I-81)

¹H NMR (300 MHz, CDCl₃) δ 1.74 (s, 3H), 1.78 (s, 3), 1.80 (s, 3), 1.83 (s, 3H), 1.98 (s, 3), 2.07 (s, 3H), 3.33 (s, 3H), 3.75 (d, J=6.6 Hz, 2H), 4.88 (d, J=6.9 Hz, 2H), 5.36–5.43 (m, 1H), 5.55–5.62 (m, 1H), 6.71 (d, J=8.0 Hz, 2H), 6.84 (dd, J=2.4, 0.8 Hz, 1H), 7.30 (d, J=8.0 Hz, 2H), 7.40 (dd, J=8.6, 2.4 Hz, 1H), 7.98 (dd, J=2.4, 0.8 Hz, 1H) ppm.

(I-90)

mp 111 to 112° C.; ¹H NMR (CDCl₃) δ 1.75 (s, 3H), 1.78 (s, 3H), 2.00 (s, 6H), 2.05 (s, 3H), 3.32 (s, 3H), 3.75 (d, J=6.9 Hz, 2H), 4.82 (dq, J=1.4, 8.6 Hz, 2), 5.39 (m, 1H), 6.70 (d, J=8.7 Hz, 2H), 6.93–6.97 (m, 3H), 7.64 (dd, J=2.4, 8.4 Hz, 1H), 8.10 (dd, J=0.3, 2.1 Hz, 1H) ppm, IR (KBr): 3407, 2931, 2860, 1613, 1521, 1292, 1274, 1259, 1240, 1164, 1070, 823 cm⁻¹

(I-114)

mp 91 to 91° C.; ¹H NMR (CDCl₃) δ 1.73 (s, 6H), 1.77 (s, 6H), 2.03 (s, 3H), 2.05 (s, 6H), 2.7 (s, 3H), 3.73 (d, J=6.6 Hz, 4H), 5.39 (t, J=6.9 Hz, 2H), 6.52–6.57 (m, 4H), 6.95–7.01(m, 4H) ppm (I-120)

mp 79 to 81° C.; ¹H NMR (CDCl₃) δ 1.73 (s, 3H), 1.74 (s, 3H), 1.77 (s, 6H), 2.06 (s, 3H), 2.07 (s, 3H), 2.27 (s, 3H), 3.72 (d, J=6.9 Hz, 2H), 3.89 (m, 2H), 4.47 (m, 1H), 5.37 (m, 2H), 6.43–6.53 (m, 3H), 6.95 (d, J=8.1 Hz, 1H), 7.01 (s, 1H), 7.07 (s, 1H), 7.48 (dd, J=2.1, 8.4 Hz, 1H), 8.14 (d, J=2.1 Hz, 1H) ppm (I-121)

mp 180 to 182° C.; ¹H NMR (CDCl₃) δ 1.26 (d, J=6.3 Hz, 12H), 1.99 (s, 12H), 3.47 (s, 2H), 3.68 (sept, J=6.3 Hz, 2H), 6.65 (d, J=8.6 Hz, 4H), 6.97 (d, J=8.6 Hz, 4H) ppm; IR (KBr): 3392, 1612, 1520, 1313, 1290, 1182, 810 cm⁻¹.

(I-122)

mp 151 to 153° C.; ¹H NMR (CDCl₃) δ 1.27 (d, J=6.0 Hz, 12H), 1.96 (s, 3H), 1.97 (s, 3H), 2.01 (s, 3H), 3.68 (m, 2H), 3.20–3.78 (bs, 2H), 4.90 (s, 1H), 6.67 (bd, J=6.9 Hz, 2H), 6.71 (d, J=8.4 Hz, 2H), 6.97 (d, J=7.8 Hz, 2H), 7.11 (d, J=8.4 Hz, 2H) ppm, IR (KBr): 3504, 3397, 2965, 2923, 2869, 1610, 1519, 1461, 1413, 1382, 1317, 1292, 1245, 1180, 1126, 1074, 815 cm⁻¹

(I-123)

mp 165 to 167° C.; ¹H NMR (CDCl₃) δ 1.27 (d, J=6.0 Hz, 12H), 2.06 (s, 6H), 3.32 (s, 6H), 3.69 (sept, J=6.0 Hz, 2H), 6.75 (br s, 4H), 7.14 (br d, J=8.4 Hz, 4H) ppm.

(I-124)

mp 192 to 194° C.; ¹H NMR (CDCl₃) δ 1.26 (d, J=6.6 Hz, 12H), 1.99 (s, 6H), 2.06 (s, 3H), 3.32 (s, 3H), 3.48 (br s, 2H), 3.68 (sept, J=6.6 Hz, 2H), 6.66 (d, J=8.4 Hz, 4H), 6.96 (d, J=8.4 Hz, 2H), 7.12 (br d, J=8.4 Hz, 21) ppm.

(I-125)

mp 102 to 104° C.; ¹H NMR (CDCl₃) δ 1.25 (d, J=6.3 Hz, 6H), 1.26 (d, J=6.0 Hz, 6H), 2.04 (s, 6H), 2.21 (s, 3H), 3.50 (brs, 2H), 3.63–3.72 (m, 2H), 6.62–6.67 (m, 4H), 6.96 (d, J=8.7 Hz, 2H), 7.01 (s, 1H), 7.17 (d, J=8.4 Hz, 2H) ppm, IR (KBr): 3377, 2964, 2921, 1612, 1521, 1482, 1463, 1382, 1315, 1290, 1245, 1184, 825 cm⁻¹

(I-126)

mp 113 to 115° C.; ¹H NMR (CDCl₃) δ 1.73 (s, 6H), 1.77 (s, 6H), 2.20 (s, 61), 3.72 (d, 4H, J=6.6 Hz), 4.07 (br s, 2H), 5.36 (t, J=6.6 Hz, 2H), 6.40 (dd, J=12.3, 2.3 Hz, 2H), 6.46 (dd, J=8.1, 2.3 Hz, 2H), 7.05–7.10 (m, 4H) ppm.

(I-132)

mp 72 to 73° C.; ¹H NMR (CDCl₃) δ 1.74 (s, 3H), 1.77 (s, 3H), 1.80 (s, 6H), 2.05 (s, 3H), 2.09 (s, 3H), 2.26 (s, 3H), 3.72 (d, J=6.6 Hz, 2H), 4.94 (d, J=6.9 Hz, 2H), 5.35–5.39 (m, 1H), 5.57–5.62 (m, 1H), 6.50–6.54 (m, 2H), 6.93 (d, J=7.8 Hz, 1H), 7.05 (s, 1H), 7.07 (s, 1H), 8.54 (s, 2H) ppm.

(I-133)

mp 111 to 112° C. ¹H-NMR: δ (CDCl₃): 1.07 (3H, s) 1.09 (3H, s) 1.73 (3H, s) 1.77 (3H, s) 1.97 (3H, s) 198 (3H, s) 2.06 (3H, s) 2.18 (1H, m) 3.32 (3H, s) 3.76 (2H, d, J=6.9 Hz) 3.87 (2H, d, J=6.9 Hz),5.40 (1H, m),5.69 (1H, brs), 6.63 (1H, dd, J=2.1, J=8.1) 6.73 (2H, d, J=8.1 Hz) 6.77 (1H, d, J=2.1 Hz) 6,90 (1H, d, J=8.4 Hz) 7.14 (2H, d, J=7.5 Hz) ppm.

Reference Example 11

Synthesis of Prodrug of Compounds (I-6)

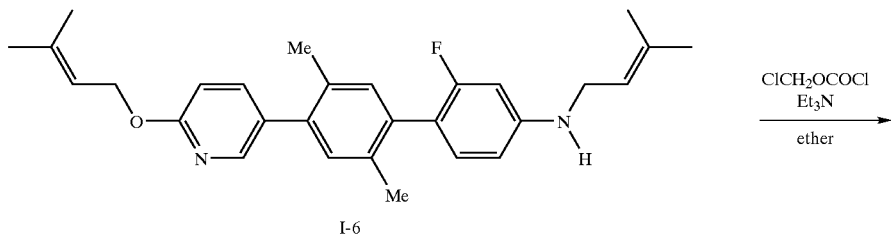

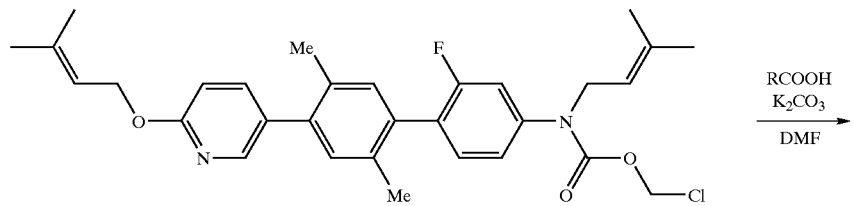

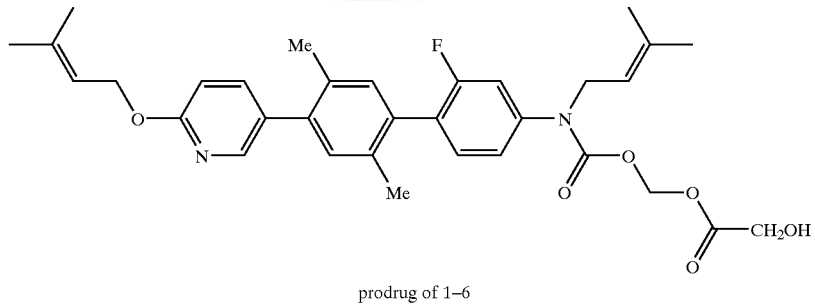

prodrug of 1-6

(Step 1) Synthesis of Compound (32)

Compound (I-6) obtained in Reference Example 1 (444 mg, 1 mmol) was dissolved in anhydrous ether (40 ml) and cooled on ice, stirred under nitrogen flow while being treated successively with chloromethyl chloroformate (194 mg, 1 mmol) and triethylamine (210 ml, 1 mmol), and then the ice bath was removed and the mixture was stirred further for 4 hours. The precipitate in the reaction mixture was filtered off, and the mixture was washed with water and dried over anhydrous sodium sulfate, and the solvent was distilled off under reduced pressure, whereby obtaining 540 mg of Compound (32) as an oil.

Anal Calcd for $C_{31}H_{34}N_2O_3FCl$: C, 69.33; H, 6.38; N, 5.22; F, 3.54; Cl, 6.60.

Found: C, 68.85; H, 6.42; N, 5.21; F, 3.58; Cl, 7.06.

(Step 2) Synthesis of Prodrug of Compounds (I-6)

A mixture of glycolic acid (38 mg, 0.5 mmol), potassium carbonate (35 mg, 0.25 mmol) and N,N-dimethylformamide (1 mL) was stirred under reduced pressure at room temperature for 10 minutes, and then treated with a solution of Compound (32) (54 mg, 0.1 mmol) in N,N-dimethylformamide (0.5 ml) followed by potassium bromide (12 mg, 0.1 mmol) and then stirred vigorously under argon atmosphere for 20 hours. The reaction mixture was diluted with ether (5 ml), and the solid was filtered off, and the mixture was washed with water and dried over anhydrous sodium sulfate, and then the solvent was distilled off under reduced pressure to obtain a crude product, which was purified by a chromatography on silica gel (eluent: hexane:ethyl acetate=2:1) to obtain 27 mg of a prodrug of Compound (I-6) as an oil.

$^1$HNMR (CDCl$_3$): δ 1.58 (3H, s), 1.73 (3H, s), 1.80 (3H, s), 1.82 (3H, s), 2.20 (3H, s), 2.28 (3H, s), 2.33 (1H, bs), 4.25 (2H, bs), 4.30 (2H, d, J=6.9 Hz), 4.88 (2H, d, J=6.9 Hz), 5.30 (1H, bt, J=6.9 Hz), 5.58 (2H, bt, J=6.9 Hz), 5.90 (2H, bs), 6.83 (1H, d, J=8.4 Hz), 6.95–7.30 (3H), 7.13 (2H, bs), 7.60 (1H, dd, J=8.4 Hz, 2.4 Hz), 8.18 (1H, d, J=2.4 Hz) ppm.

Anal Calcd for $C_{33}H_{37}N_2O_6F$: C, 68.73; H, 6.47; N, 4.86; F. 3.29.

Found: C, 68.59; H, 6.68; N, 4.98; F. 3.25.

Experiment 1 Inhibitory Effect on Induction of Differentiation from Th0 Cells to Th2 Cells 1. Animals In an experiment to induce the differentiation from Th0 cells to Th2 cells, 9 to 11 week-old female mice of BALB/cCrSlc purchased from Japan SLC, Inc. or of BALB/cAnNCrj purchased from Charles River Japan, Inc. were used.

In an experiment to induce the differentiation from Th0 cells to Th1 cells, 8 week-old female mice of C57BL/6NCrj purchased from Charles River Japan, Inc. were used.

2. Immunization and Administration of Inventive Compounds

In an experiment to induce the differentiation from Th0 cells to Th2 cells, a DNP-As (dinitrophenylated *Ascaris* protein (porcine ascarid extract protein)) was used as an antigen, 10 μg of which and 250 μg of Alum (aluminum hydroxide adjuvant) in physiological saline in the final volume of 50 μl was injected into the soles of the both hind legs of each mouse, whereby effecting immunization. In a negative control group, each animal was treated similarly by an injection of 50 μl of physiological saline. 6 Days after injection, two popliteal lymph nodes were removed from right and left knees, and passed through a metal mesh (200 mesh size) in Hanks' balanced salt solution (HBSS) to prepare a cell suspension. In the group treated with physiological saline, preparations from two animals were combined and subjected to the experiment because of a small cell number. A compound according to the invention was suspended in 0.5% methylcellulose (MC) and 0.1 ml per 20 g mouse was given orally every day over a period from the day of immunization through the 5th day. The immunized vehicle control group and the negative control group were treated with the same volume of 0.5% MC.

On the other hand, in an experiment to induce the differentiation from Th0 cells to Th1 cells, a non-viable *Mycobacterium tuberculosis* H37RA (DIFCO) was suspended in physiological saline, and 125 μg/50 μl was used for immunization as described above. In the group treated with physiological saline, the preparations from 4 animals were combined and subjected to the experiment.

3. Intracellular Cytokines Detection by FACS Method

Cells prepared from popliteal lymph nodes of these mice were suspended at 1–2×10$^6$ cells/ml (1–2 ml) in an RPMI 1640 medium (containing 10% fetal bovine serum—FBS and 50 μM 2-mercaptoethanol) and supplemented with PMA (Phorbol 12-Myristate 13-Acetate) at the final concentration of 50 ng/ml and 250 ng/ml A23187 (Ca ionophore) and then incubated at 37° C. in the presence of 5% CO$_2$. After incubating for 4 hours, Brefeldin A was added at the final concentration of 10 μg/ml and the mixture was incubated further for 2 hours. The cells were recovered and washed twice with a staining buffer (PBS containing 1% FBS and 0.1% sodium azide) and suspended in 100 μl of the staining buffer containing 5 μg/ml of Fc Block (rat anti-mouse CD 16/CD32 purified monoclonal antibody, Pharmingen) and incubated on ice for 5 minutes to block the non-specific adsorption of the labeled antibody, and then combined with an equal volume of a Cy-Chrome-labelled rat anti-mouse CD4 monoclonal antibody (Pharmingen) which had been 200-fold diluted with the staining buffer and incubated on ice for 30 minutes. After washing three times with the staining buffer, the cells were suspended in PBS and combined with an equal volume of a fixation solution (4% p-formaldehyde) and incubated at 4° C. overnight, whereby effecting the fixation. The fixed cells thus obtained were washed twice with the staining buffer and suspended in a permeabilazation buffer (PBS containing 1% FBS, 0.5% saponin and 0.1% sodium azide) and incubated on ice for 10 minutes, and then each cell sample was recovered as being divided into two equal portions. Each portion was suspended in 100 µl of the permeabilazation buffer containing 5 µg/ml Fc Block and incubated on ice for 5 minutes to block the non-specific adsorption of the labeled antibody into the cells. One portion was combined with each 100 µl of an FITC-labelled rat anti-mouse IFNγ monoclonal antibody (Pharmingen) and a PE-labeled rat anti-mouse IL-4 monoclonal antibody (Pharmingen) each had been 50-fold diluted with the permeabilazation buffer and incubated on ice for 30 minutes. The other portion, serving as a control representing the non-specific adsorption of the labeled antibody, was combined with each 100 µl of each control antibody at the same concentration, i.e., an FITC-labelled rat IgG1κ purified antibody (Pharmingen) and a PE-labeled rat IgG1κ purified antibody (Pharmingen) to effect the similar staining. After washing three times with the cell membrane permeation buffer and twice with the staining buffer, the cells were suspended in 500 µl of the staining buffer and transferred through a nylon mesh into a FACS analysis tube.

FACScan (Nippon Becton Dickinson Company Ltd.) was used to determine the percentage of IFNγ positive cells (Th1) and the percentage of IL-4 positive cells (Th2) in CD4 positive T cells, from each of which the percentage of non-specific positive cells stained by a control antibody was subtracted to obtain % Th1 and % Th2, while in the Th2 differentiation experiment a Th2/Th1 cell ratio was determined, and then based on these data the effect of a compound according to the invention of the differentiation from Th0 to Th1 or Th2 was investigated. The significant difference was analyzed by Dunnett multiple comparison test and Student t test. The results are shown in Tables 13 and 14.

TABLE 14

Effect of compounds on change in % Th1 and % Th2 in popliteal lymph node 6 days after immunization of C57BL/6N mice with non-viable *Mycobacterium tuberculosis*

| Immunization method | Compound | Dose (mg/kg) | % Th1 | % Th2 |
|---|---|---|---|---|
| Physiological saline | | | 0.28 ± 0.09## | −0.20 ± 0.19 |
| *M. tuberculosis* | Control | | 1.22 ± 0.10 | 0.13 ± 0.11 |
| | I-6 | 40 | 1.03 ± 0.10 | 0.03 ± 0.02 |
| | I-80 | 40 | 0.93 ± 0.11 | 0.02 ± 0.04 |
| | I-89 | 10 | 0.70 ± 0.20 | 0.02 ± 0.06 |
| | I-102 | 40 | 0.82 ± 0.16 | 0.07 ± 0.04 |

% Th1 and % Th2 are the values after subtracting the percentage positive for the negative control antibody (n = 3).
P < 0.01 vs control group (Student's t-test)

Results

As shown in Table 13, the CD4 positive T cells in the popliteal lymph node of BALB/c mice immunized with DNP-As exhibited an increase in the % Th2 and in the Th2/Th1 ratio when compared with the non-immunized group received the injection only of physiological saline, thus validating the induction of the Th2-dominant differentiation. Against such induction, each of Compounds I-55, I-80, I-90, I-102, I-132 and I-133 at 40 mg/kg and I-89 at 10 mg/kg significantly inhibited the increase in the % Th2 and in the Th2/Th1 ratio when given orally for consecutive 6 days after immunization, resulting in the correction from the Th2-dominant condition. Compound I-6 significantly inhibited the increase in the % Th2 and in the Th2/Th1 ratio at a concentration of 10 mg/kg or higher, resulting in the correction from the Th2-dominant condition.

On the other hand, as shown in Table 4, the CD4 positive T cells in the popliteal lymph node of C57BL/6 mice

TABLE 13

Effect of compounds on change in % Th1, % Th2 and Th2/Th1 in popliteal lymph node 6 days after immunization of BALB/c mice with DNP-As

| Immunization method | Compound | Dose (mg/kg) | % Th2 | % Th1 | Th2/Th1 |
|---|---|---|---|---|---|
| Physiological saline | | | 0.05 ± 0.01## | 0.36 ± 0.06 | 0.14 ± 0.02## |
| DNP-As/Alum | Control | | 1.37 ± 0.17 | 0.37 ± 0.01 | 3.75 ± 0.52 |
| | I-80 | 40 | 0.07 ± 0.03** | 0.29 ± 0.03 | 0.27 ± 0.12** |
| | I-89 | 10 | −0.04 ± 0.00** | 0.23 ± 0.02 | −0.19 ± 0.01** |
| | I-102 | 40 | −0.01 ± 0.01** | 0.34 ± 0.09 | −0.05 ± 0.06** |
| Physiological saline | | | 0.00 ± 0.00# | 0.27 ± 0.07# | −0.01 ± 0.01## |
| DNP-As/Alum | Control | | 0.99 ± 0.29 | 0.60 ± 0.08 | 1.58 ± 0.28 |
| | I-6 | 2.5 | 1.41 ± 0.10 | 0.70 ± 0.02 | 2.03 ± 0.20 |
| | | 10 | 0.15 ± 0.01* | 0.54 ± 0.05 | 0.29 ± 0.02** |
| | | 40 | 0.03 ± 0.03** | 0.66 ± 0.02 | 0.04 ± 0.05** |
| Physiological saline | | | 0.04 ± 0.01## | 0.33 ± 0.02## | 0.13 ± 0.02## |
| DNP-As/Alum | Control | | 1.34 ± 0.19 | 0.56 ± 0.04 | 2.35 ± 0.16 |
| | I-55 | 40 | 0.05 ± 0.02** | 0.53 ± 0.05 | 0.09 ± 0.03** |
| | I-90 | 40 | 0.08 ± 0.03** | 0.40 ± 0.02 | 0.22 ± 0.09** |
| | I-132 | 40 | 0.05 ± 0.02** | 0.46 ± 0.07 | 0.12 ± 0.04** |
| | I-133 | 40 | 0.20 ± 0.05** | 0.45 ± 0.03 | 0.45 ± 0.09** |

% Th1 and % Th2 are the values after subtracting the percentage positive for the negative control antibody (n = 3).
*p < 0.05, **p < 0.01 vs control group (Dunnett's test), #p < 0.05, ##P < 0.01 vs control group (Student's t-test).

immunized with non-viable *Mycobacterium tuberculosis* exhibited a selective increase in the % Th1 when compared with the non-immunized group received the injection only of physiological saline, thus validating the induction of the Th1-dominant differentiation. Against such induction, any of Compounds I-6, I-80, I-89 and I-102 showed no effect on the increase in the % Th1.

Accordingly, the compounds according to the invention were revealed to have the selective inhibitory effect on the differentiation from Th0 to Th2.

Example 1

Tablet

| | |
|---|---|
| Compound (I-6) | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

The components other than calcium stearate were mixed uniformly, pulverized and dried to form a granule of an appropriate particle size. Subsequently, calcium stearate was added and the mixture was compressed into a tablet.

Example 2

Granule

| | |
|---|---|
| Compound (I-80) | 30 g |
| Lactose | 265 g |
| Magnesium stearate | 6 g |

The components were mixed well and compressed and then pulverized, sized and sieved to obtain a granule of an appropriate particle size.

Example 3

Capsule

| | |
|---|---|
| Compound (I-89) | 10 g |
| Heavy magnesium oxide | 20 g |
| Lactose | 70 g |

The components shown above were mixed well into a particulate or fine particulate powder, and filled in a capsule.

INDUSTRIAL APPLICABILITY

As evident from Experiments described above, any of the compounds according to the invention exhibited an inhibitory effect on the differentiation from Th0 cells to Th2 cells, and thus is extremely useful as Th2 cell differentiation inhibitors and as therapeutic agents against autoimmune diseases.

What is claimed is:

1. A method for treating graft immune diseases (chronic GVHD), ulcerative colitis, systemic lupus erythematodes, myasthenia gravis, systemic progressive scleroderma, rheumatoid arthritis, interstitial cystitis, Hashimoto's diseases, Basedow's diseases, autoimmune hemolytic anemia, idiopathic thrombocytopenic purpura, Goodpasture's syndrome, atrophic gastritis, pernicious anemia, Addison diseases, pemphigus, pemphigoid, lenticular uveitis, sympathetic ophthalmia, primary biliary cirrhosis, active chronic hepatitis, Sjogren's syndrome, multiple myositis, dermatomyositis, polyarteritis nodosa, rheumatic fever, glomerular nephritis, lupus nephritis, IgA nephtopathy, allergic encephalitis, atopic allergic diseases, bronchial asthma, airway inflammation, allergic rhinitis, allergic dermatitis, allergic conjunctivitis, pollinosis, urticaria, food allergy, Omenn's syndrome, vernal conjunctivitis or hypereosinophilic syndrome comprising inhibiting the differentiation from Th0 cells to Th2 cells by administering to a patient in need thereof a compound represented by Formula (I):

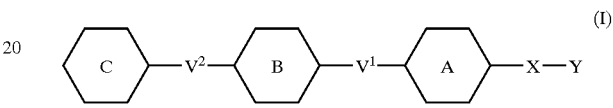

wherein each of ring A and ring B is independently an optionally substituted benzene ring;

ring C is an optionally substituted pyridine ring wherein the substituent is halogen; hydroxy; lower alkyl which may be substituted by hydroxy or acyloxy; lower alkoxy which may be substituted by halogen, aryl or a 5- or 6-membered heterocyclic group; lower alkenyl; lower alkenyloxy; lower alkynyl; lower alkynyloxy; acyloxy; carboxy; lower alkoxycarbonyl; mercapto; lower alkylthio; lower alkenylthio; amino which may be mono- or di-substituted by halogen, optionally substituted lower alkyl (a substituent is cycloalkyl or a 5- or 6-membered heterocyclic group), optionally halogen-substituted acyl, lower alkenyl, cycloalkyl or lower alkylsulfonyl; imino which may be substituted by lower alkylsulfonyl; hydrazino which may be substituted by lower alkyl, lower alkenyl, optionally substituted lower alkylidene or cycloalkylidene; aminooxy which may be substituted by lower alkyl, lower alkenyl, optionally substituted lower alkylidene or cycloalkylidene; nitro; lower alkylsulfonyl; aryl; a 5- or 6-membered heterocyclic group; oxo; or oxide;

X is —O—, —NR$^1$— (wherein R$^1$ is hydrogen, optionally substituted lower alkyl, lower alkenyl or lower alkylcarbonyl) or —S(O)-p-wherein p is an integer of 0 to 2;

Y is hydrogen, optionally substituted lower alkyl, optionally substituted lower alkoxy, optionally substituted lower alkenyl, optionally substituted lower alkynyl, optionally substituted acyl, optionally substituted cycloalkyl, optionally substituted cycloalkenyl, optionally substituted lower alkoxycarbonyl, optionally substituted sulfamoyl, optionally substituted amino, optionally substituted aryl, pyrrole, imidazole, pyrazole, pyridine, pyridazine, pyrimidine, pyrazine, triazole, triazine, isoxazole, oxazole, oxadiazole, isothiazole, thiazole, thiadiazole, furan, thiophene, tetrahydropyran, dihydropyridine, dihydropyridazine, dihydropyrazine, dioxane, oxathiolane, thiane, pyrrolidine, pyrroline, imidazolidine, imidazoline, pyrazolidine, pyrazoline, piperidine, or morpholine;

R1 and Y taken together may form —(CH$_2$)$_m$—, —(CH$_2$)$_2$—T—(CH$_2$)$_2$— wherein T is O, S or NR', —CR'=CH—CH=CR'—, —CH=N—CH=CH—, —N=CH—N=CH—, —C(=O)—O—(CH$_2$)r-, —C(=O)—NR'—(CH$_2$)r- or —C(=O)—NR'—N=CH— wherein m is 4 or 5, r is 2 or 3 and R' is hydrogen, lower alkyl or lower alkenyl;

Y may be halogen when X is —NR$^1$— and

Y may be optionally substituted lower alkylsulfonyl or optionally substituted arylsulfonyl when X is —O— or —NR$^1$—;

both V$^1$ and V$^2$ are single bonds or one of V$^1$ and V$^2$ is a single bond and the other is —O—, —NH—, —OCH$_2$—, —CH$_2$O—, —CH=CH—, —C≡C—, CH(OR$^2$)— wherein R$^2$ is hydrogen or lower alkyl, —CO—, —NHCHR$^3$— or CHR$^3$NH— wherein R$^3$ is hydrogen or hydroxy, or a prodrug, pharmaceutically acceptable salt or solvate thereof.

2. The method as claimed in claim 1 wherein X is —O— or —NR$^1$—, wherein R$^1$ is hydrogen, lower alkyl or lower alkenyl.

3. The method as claimed in claim 1 wherein Y is optionally substituted lower alkyl or optionally substituted lower alkenyl.

4. The method as claimed in claim 1 wherein both of V$^1$ and V$^2$ are single bonds.

5. The method as claimed in claim 1, wherein the disease is selected from the group consisting of ulcerative colitis, systemic lupus erythematodes, lupus nephritis and rheumatoid arthritis.

6. A method for treating graft immune diseases (chronic GVHD), ulcerative colitis, systemic lupus erythematodes, myasthenia gravis, systemic progressive scleroderma, rheumatoid arthritis, interstitial cystitis, Hashimoto's diseases, Basedow's diseases, autoimmune hemolytic anemia, idiopathic thrombocytopenic purpura, Goodpasture's syndrome, atrophic gastritis, pernicious anemia, Addison diseases, pemphigus, pemphigoid, lenticular uveitis, sympathetic ophthalmia, primary biliary cirrhosis, active chronic hepatitis, Sjogren's syndrome, multiple myositis, dermatomyositis, polyarteritis nodosa, rheumatic fever, glomerular nephritis, lupus nephritis, IgA nephtopathy, allergic encephalitis, atopic allergic diseases, bronchial asthma, airway inflammation, allergic rhinitis, allergic dermatitis, allergic conjunctivitis, pollinosis, urticaria, food allergy, Omenn's syndrome, vernal conjunctivitis or hypereosinophilic syndrome comprising inhibiting the differentiation from Th0 cells to Th2 cells by administering to a patient in need thereof a compound represented by Formula (Ib):

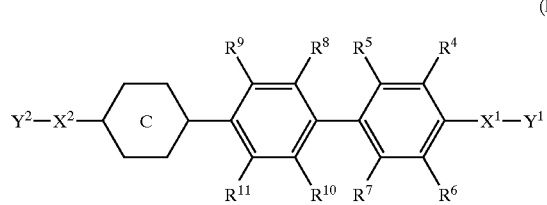

(Ib)

wherein ring C is

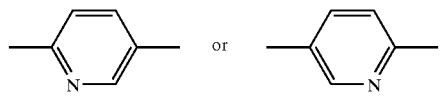

and the pyridine ring may be optionally substituted, each of R$^4$, R$^5$, R$^6$, R$^7$, R$^8$, R$^9$, R$^{10}$, and R$^{11}$ is independently hydrogen, halogen, hydroxy, optionally substituted lower alkyl, optionally substituted lower alkoxy, carboxy or lower alkoxycarbonyl;

each of X$^1$ and X$^2$ is independently —O—, —CH$_2$— or —NH—;

each of Y$^1$ and Y$^2$ is independently optionally substituted lower alkyl, optionally substituted arylalkyl or optionally substituted lower alkenyl, or a prodrug, pharmaceutically acceptable salt or solvate thereof.

7. The method as claimed in claim 6 wherein one of R$^4$ and R$^5$ is hydrogen, hydroxy or lower alkyl and the other is hydrogen or halogen, and both of R$^6$ and R$^7$ are hydrogens.

8. The method as claimed in claim 6 wherein each of R$^8$ and R$^{11}$ is independently hydrogen, hydroxy, lower alkyl or lower alkoxycarbonyl, and each of R$^9$ and R$^{10}$ is independently hydroxy, lower alkyl, lower alkoxy or lower alkoxycarbonyl.

9. The method as claimed in claim 6 wherein one of X$^1$ and X$^2$ is —O— and the other is —NH—.

10. The method as claimed in claim 6 wherein each of Y$^1$ and Y$^2$ is independently optionally halogen-substituted lower alkyl or optionally halogen-substituted lower alkenyl.

11. The method as claimed in claim 6 wherein one of —X$^1$—Y$^1$ and —X$^2$—Y$^2$ is prenylamino and the other is prenyloxy.

12. A method for treating graft immune diseases (chronic GVHD), ulcerative colitis, systemic lupus erythematodes, myasthenia gravis, systemic progressive scleroderma, rheumatoid arthritis, interstitial cystitis, Hashimoto's diseases, Basedow's diseases, autoimmune hemolytic anemia, idiopathic thrombocytopenic purpura, Goodpasture's syndrome, atrophic gastritis, pernicious anemia, Addison diseases, pemphigus, pemphigoid, lenticular uveitis, sympathetic ophthalmia, primary biliary cirrhosis, active chronic hepatitis, Sjogren's syndrome, multiple myositis, dermatomyositis, polyarteritis nodosa, rheumatic fever, glomerular nephritis, lupus nephritis, IgA nephtopathy, allergic encephalitis, atopic allergic diseases, bronchial asthma, airway inflammation, allergic rhinitis, allergic dermatitis, allergic conjunctivitis, pollinosis, urticaria, food allergy, Omenn's syndrome, vernal conjunctivitis or hypereosinophilic syndrome comprising inhibiting the differentiation from Th0 cells to Th2 cells by administering to a patient in need thereof a compound represented by Formula (Ic):

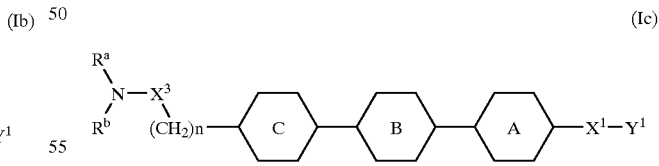

(Ic)

wherein each of ring A and ring B is independently an optionally substituted benzene ring;

ring C is an optionally substituted pyridine ring;

X$^1$ is —O—, —CH$_2$—, or —NH— and Y$^1$ is optionally substituted lower alkyl, optionally substituted arylalkyl or optionally substituted lower alkenyl;

X$^3$ is —O— or —NH—;

each of R$^a$ and R$^b$ is independently hydrogen, optionally substituted lower alkyl, optionally substituted lower alkenyl, optionally substituted aryl, optionally substituted cycloalkyl, optionally substituted acyl, optionally substituted lower alkoxycarbonyl or optionally substituted lower alkylsulfonyl, or they are taken together to form $R^cR^dC=$ or $—(CR^eR^f)s-$;

each of $R^c$ and $R^d$ is independently hydrogen, optionally substituted lower alkyl, optionally substituted lower alkenyl, optionally substituted lower alkynyl, optionally substituted lower alkoxy, optionally substituted lower alkylthio, optionally substituted lower alkenyloxy, optionally substituted lower alkynyloxy, optionally substituted cycloalkyl, optionally substituted aryl or optionally substituted 5- or 6-membered heterocyclyl or they are taken together with a carbon atom to which they are attached to form optionally substituted cycloalkylidene;

each $R^e$ is independently hydrogen, lower alkyl, lower alkoxy or amino, and each $R^f$ is independently hydrogen, lower alkyl, lower alkoxy or amino;

n is an integer of 0 to 2 and s is an integer of 2 to 6, or a prodrug, pharmaceutically acceptable salt or solvate thereof.

13. A method for inhibiting the differentiation from Th0 cells to Th2 cells comprising administering to a patient in need thereof a compound represented by Formula (I):

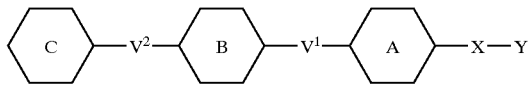

(I)

wherein each of ring A and ring B is independently an optionally substituted benzene ring;

ring C is an optionally substituted pyridine ring wherein the substituent is halogen; hydroxy; lower alkyl which may be substituted by hydroxy or acyloxy; lower alkoxy which may be substituted by halogen, aryl or a 5- or 6-membered heterocyclic group; lower alkenyl; lower alkenyloxy; lower alkynyl; lower alkynyloxy; acyloxy; carboxy; lower alkoxycarbonyl; mercapto; lower alkylthio; lower alkenylthio; amino which may be mono- or di-substituted by halogen, optionally substituted lower alkyl (a substituent is cycloalkyl or a 5- or 6-membered heterocyclic group), optionally halogen-substituted acyl, lower alkenyl, cycloalkyl or lower alkylsulfonyl; imino which may be substituted by lower alkylsulfonyl; hydrazino which may be substituted by lower alkyl, lower alkenyl, optionally substituted lower alkylidene or cycloalkylidene; aminooxy which may be substituted by lower alkyl, lower alkenyl, optionally substituted lower alkylidene or cycloalkylidene; nitro; lower alkylsulfonyl; aryl; a 5- or 6-membered heterocyclic group; oxo; or oxide;

X is $—O—$, $—NR^1—$ (wherein $R^1$ is hydrogen, optionally substituted lower alkyl, lower alkenyl or lower alkylcarbonyl) or $—S(O)-p-$wherein p is an integer of 0 to 2;

Y is hydrogen, optionally substituted lower alkyl, optionally substituted lower alkoxy, optionally substituted lower alkenyl, optionally substituted lower alkynyl, optionally substituted acyl, optionally substituted cycloalkyl, optionally substituted cycloalkenyl, optionally substituted lower alkoxycarbonyl, optionally substituted sulfamoyl, optionally substituted amino, optionally substituted aryl, pyrrole, imidazole, pyrazole, pyridine, pyridazine, pyrimidine, pyrazine, triazole, triazine, isoxazole, oxazole, oxadiazole, isothiazole, thiazole, thiadiazole, furan, thiophene, tetrahydropyran, dihydropyridine, dihydropyridazine, dihydropyrazine, dioxane, oxathiolane, thiane, pyrrolidine, pyrroline, imidazolidine, imidazoline, pyrazolidine, pyrazoline, piperidine, or morpholine;

$R^1$ and Y taken together may form $—(CH_2)_m—$, $—(CH_2)_2—T—(CH_2)_2—$ wherein T is O, S or NR', $—CR'=CH—CH=CR'—$, $—CH=N—CH=CH—$, $—N=CH—N=CH—$, $C(=O)—(CH_2)r-$, $—C(=O)—NR'—(CH_2)r-$ or $—C(=O)—NR'—N=CH—$ wherein m is 4 or 5, r is 2 or 3 and R' is hydrogen, lower alkyl or lower alkenyl;

Y may be halogen when X is $—NR^1—$ and

Y may be optionally substituted lower alkylsulfonyl or optionally substituted arylsulfonyl when X is $—O—$ or $—NR^1—$;

both $V^1$ and $V^2$ are single bonds or one of $V^1$ and $V^2$ is a single bond and the other is $—O—$, $—NH—$, $—OCH_2—$, $—CH_2O—$, $—CH=CH—$, $—C\equiv C—$, $—CH(OR^2)—$ wherein $R^2$ is hydrogen or lower alkyl, $—CO—$, $—NHCHR—$ or $—CHR^3NH—$ wherein $R^3$ is hydrogen or hydroxy, or a prodrug, pharmaceutically acceptable salt or solvate thereof.

14. A method for inhibiting the differentiation from Th0 cells to Th2 cells comprising administering to a patient in need thereof a compound represented by Formula (Ib):

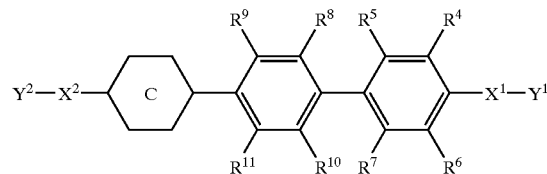

(Ib)

wherein ring C is an optionally substituted

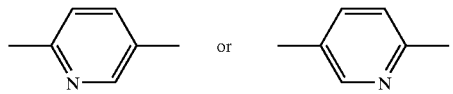

and the pyridine ring may be optionally substituted, each of $R^4$, $R^5$, $R^6$, $R^7$, $R^8$, $R^9$, $R^{10}$, and $R^{11}$ is independently hydrogen, halogen, hydroxy, optionally substituted lower alkyl, optionally substituted lower alkoxy, carboxy or lower alkoxycarbonyl;

each of $X^1$ and $X^2$ is independently $—O—$, $—CH_2—$ or $—NH—$;

each of $Y^1$ and $Y^2$ is independently optionally substituted lower alkyl, optionally substituted arylalkyl or optionally substituted lower alkenyl, or a prodrug, pharmaceutically acceptable salt or solvate thereof.

15. A method for treating graft immune diseases (chronic GVHD), ulcerative colitis, systemic lupus erythematodes, myasthenia gravis, systemic progressive scleroderma, rheumatoid arthritis, interstitial cystitis, Hashimoto's diseases, Basedow's diseases, autoimmune hemolytic anemia, idiopathic thrombocytopenic purpura, Goodpasture's syndrome, atrophic gastritis, pernicious anemia, Addison diseases, pemphigus, pemphigoid, lenticular uveitis, sympathetic ophthalmia, primary biliary cirrhosis, active chronic hepatitis, Sjogren's syndrome, multiple myositis, dermatomyositis, polyarteritis nodosa, rheumatic fever, glomerular nephritis, lupus nephritis, IgA nephtopathy, allergic encephalitis, atopic allergic diseases, bronchial asthma, airway inflammation, allergic rhinitis, allergic dermatitis, allergic conjunctivitis, pollinosis, urticaria, food allergy, Omenn's syndrome, vernal conjunctivitis or hypereosinophilic syndrome comprising inhibiting the differentiation from Th0 cells to Th2 cells by administering to a patient in need thereof a compound represented by Formula (Ib)

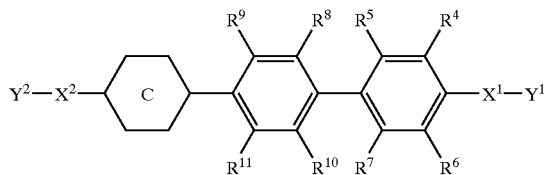

(Ib)

wherein ring C is an optionally substituted pyridine ring, each of $R^4$, $R^5$, $R^6$, $R^7$, $R^8$, $R^9$, $R^{10}$, and $R^{11}$ is independently hydrogen, halogen, hydroxy, optionally substituted lower alkyl, optionally substituted lower alkoxy, carboxy or lower alkoxycarbonyl;

each of $X^1$ and $X^2$ is independently —O— or —NH—;

each of $Y^1$ and $Y^2$ is independently optionally substituted lower alkyl, optionally substituted arylalkyl or optionally substituted lower alkenyl, or a prodrug, pharmaceutically acceptable salt or solvate thereof.

16. A method for inhibiting the differentiation from Th0 cells to Th2 cells comprising administering to a patient in need thereof a compound represented by Formula (Ib):

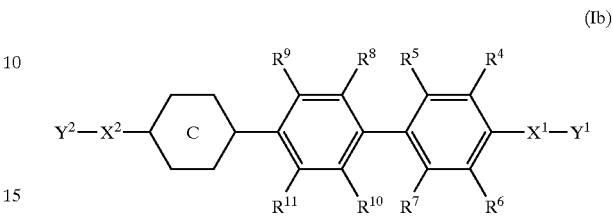

(Ib)

wherein ring C is an optionally substituted pyridine ring, each of $R^4$, $R^5$, $R^6$, $R^7$, $R^8$, $R^9$, $R^{10}$, $R^{11}$, and $R^{11}$ is independently hydrogen, halogen, hydroxy, optionally substituted lower alkyl, optionally substituted lower alkoxy, carboxy or lower alkoxycarbonyl;

each of $X^1$ and $X^2$ is independently —O— or —NH—;

each of $Y^1$ and $Y^2$ is independently optionally substituted lower alkyl, optionally substituted arylalkyl or optionally substituted lower alkenyl, or a prodrug, pharmaceutically acceptable salt or solvate thereof.

* * * * *